(12) United States Patent
Elliott et al.

(10) Patent No.: US 9,289,381 B2
(45) Date of Patent: Mar. 22, 2016

(54) STABILIZATION AND STORAGE OF BIOLOGICAL PHARMACEUTICAL COMPOSITIONS

(75) Inventors: Gloria Elliott, Midland, NC (US);
Douglas MacFarlane, Brighton (AU);
David M. Foureau, Charlotte, NC (US);
Iain McKillop, Charlotte, NC (US)

(73) Assignees: The University of North Carolina at Charlotte, Charlotte, NC (US); The Charlotte-Mecklenburg Hospital Authority, Charlotte, NC (US); Monash University, Clayton VIC (AU)

( * ) Notice: Subject to any disclaimer, the term of this patent is extended or adjusted under 35 U.S.C. 154(b) by 0 days.

(21) Appl. No.: 13/392,784

(22) PCT Filed: Dec. 3, 2010

(86) PCT No.: PCT/US2010/058842
§ 371 (c)(1),
(2), (4) Date: Apr. 5, 2012

(87) PCT Pub. No.: WO2011/069037
PCT Pub. Date: Jun. 9, 2011

(65) Prior Publication Data
US 2012/0230944 A1    Sep. 13, 2012

Related U.S. Application Data

(60) Provisional application No. 61/266,197, filed on Dec. 3, 2009, provisional application No. 61/286,048, filed on Dec. 14, 2009, provisional application No. 61/388,682, filed on Oct. 1, 2010, provisional application No. 61/412,428, filed on Nov. 11, 2010.

(51) Int. Cl.
| | |
|---|---|
| *A61K 38/20* | (2006.01) |
| *A61K 38/24* | (2006.01) |
| *A61K 39/395* | (2006.01) |
| *A61K 38/02* | (2006.01) |
| *A61K 38/21* | (2006.01) |
| *A61K 38/27* | (2006.01) |
| *A61K 9/00* | (2006.01) |
| *A61K 38/47* | (2006.01) |
| *A61K 47/24* | (2006.01) |

(52) U.S. Cl.
CPC ............ *A61K 9/0019* (2013.01); *A61K 38/2013* (2013.01); *A61K 38/47* (2013.01); *A61K 47/24* (2013.01)

(58) Field of Classification Search
None
See application file for complete search history.

(56) References Cited

U.S. PATENT DOCUMENTS

| | | | |
|---|---|---|---|
| 2005/0020814 A1* | 1/2005 | Rudolph et al. | 530/350 |
| 2007/0093462 A1 | 4/2007 | Rogers et al. | |
| 2009/0226530 A1* | 9/2009 | Lassner et al. | 424/497 |

FOREIGN PATENT DOCUMENTS

WO    WO 2009/015367 A2    1/2009

OTHER PUBLICATIONS

National Cancer Institute Cancer Drug Information for Aldesleukin.*
Chang, B.S. and Hershenson, S. 2002. Practical approaches to protein formulation development in "Rationale Design of stable protein formulations-theory and practice" (J.F. Carpenter and M.C. Manning eds.) Kluwer Academic/Plenum publishers, New York. pp. 1-25.*
Osmolyte effects on protein stability and solubility: a balancing act between backbone and side-chains. Auton M, Rösgen J, Sinev M, Holthauzen LM, Bolen DW. Biophys Chem. Nov. 2011;159(1):90-9. doi: 10.1016/j.bpc.2011.05.012. Epub May 19, 2011.*
CDHP MW. Molecular weight of choline dihydrogen phosphate as shown on ChemSpider.*
Water MW. Molecular weight of water as shown on ChemSpider.*
NIH Daily Med Proleukin. Molecular weight of Interleukin-2 as shown by NIH Daily Med.*
Development of a New Formulation to Enable Sustained IL-2 Release In Vivo. David M. Foureau, Chase P. Jones, Katherine Weaver, Regina M. Vrikkis, Douglas R. MacFarlane, Iain H. Mckillop, Jonathan C. Salo, Gloria D. Elliott. Journal of Immunotherapy: Oct. 2010—vol. 33—Issue 8—pp. 859-920. (Foureau abstract p. 896).*
Vrikkis RM et al. Biocompatible ionic liquids: a new approach for stabilizing proteins in liquid formulation. Journal of Biomechanical Engineering. Jul. 2009; 131: 074514-1-074514-4.
Fujita K et al. Solubility and stability of cytochrome c in hydrated ionic liquids: effect of oxo acid residues and kosmotropicity. Biomacromolecules. 2007; 8: 2080-2086.
International Search Report and Written Opinion, PCT/US2010/058842, mailed Jan. 31, 2012.
Fujita K et al. Choline dihydrogen phosphate. Acta Crystallographica Section E. 2009; E65; o709 and supplementary materials.
Fujita K et al. Protein solubilising and stabilising ionic liquids. The Royal Society of Chemistry. Chem Comm. 2005; 4804-4806.
Fujita K et al. Unexpected improvement in stability and utility of cytochrome c by solution in biocompatible ionic liquids. Biotechnology and Bioengineering. Aug. 20, 2006; 94(6): 1209-1213.
Proleukin Pharmacology and Indications. Novartis product information. 2009: 5 pp, retrieved Nov. 30, 2009.
Fujita et al., "Protein solubilising and stabilizing ionic liquids," Chem. Commun. 4804-4806 2005.
Fujita et al., "Enzymatic Activity and Thermal Stability of Metallo Proteins in Hydrated Ionic Liquids," Biopolymers 93:1093-1099 (2010).
Creighton TE. Proteins: Structures and Molecular Properties, 2nd Ed. Section 7.1.1 Aqueous Solubility, pp. 262-263. Section 7.4.4. Physical Basis for Protein Denaturation, pp. 292-294. W.H. Freeman and Company. New York. 1992.
Constatinescu D et al. Patterns of protein unfolding and protein aggregation in ionic liquids. Physical Chemistry Chemical Physics. Jan. 6, 2010; 12: 1756-1763.
MacFarlane DG et al. Ionic liquid "buffers"—pH control in ionic liquid systems. Chem. Commun. Sep. 27, 2010; 46: 7703-7705.

* cited by examiner

*Primary Examiner* — Brian J Gangle
*Assistant Examiner* — Andrea McCollum
(74) *Attorney, Agent, or Firm* — Myers Bigel & Sibley, P.A.

(57) ABSTRACT

The present invention relates to compositions and methods for the preparation, stabilization, and/or storage of active agents, particularly therapeutic proteins and polypeptides such as Interleukin-2.

23 Claims, 16 Drawing Sheets

(a)

(b)

STABILIZATION AND STORAGE OF BIOLOGICAL PHARMACEUTICAL COMPOSITIONS

RELATED APPLICATION DATA

This application is a 35 U.S.C. §371 national phase entry of PCT Application PCT/US2010/058842, filed Dec. 3, 2010, and published in English on Jun. 9, 2011, as International Publication No. WO 2011/069037, and which claims the benefit of U.S. Provisional Patent Application Ser. No. 61/266,197, filed Dec. 3, 2009, U.S. Provisional Patent Application Ser. No. 61/286,048, filed Dec. 14, 2009, U.S. Provisional Patent Application Ser. No. 61/388,682, filed Oct. 1, 2010, and U.S. Provisional Patent Application Ser. No. 61/412,428, filed Nov. 11, 2010, the disclosures of all of which are incorporated herein by reference in their entirety.

STATEMENT OF GOVERNMENT SUPPORT

This invention was made with government support under award number SBE0548401 by the National Science Foundation and award number 1R21EB00740401A2 by the National Institutes of Health. The United States government has certain rights to this invention.

FIELD OF THE INVENTION

The present invention relates to compositions and methods for the preparation, stabilization, and/or storage of polypeptides, particularly therapeutic polypeptides.

BACKGROUND OF THE INVENTION

The use of biological therapeutics to treat a range of medical conditions is becoming increasingly popular in modern medicine. These pharmaceutical compositions may contain an active ingredient such as a protein and a pharmaceutically acceptable carrier or solvent. Proteins are biological molecules that elicit a specific response in the human body, thus the pharmaceutical industry has an interest in using these biomolecules as drugs to cure and manage disease. Protein drugs tend to be unstable as a result of their complex three dimensional structures. The interaction within, and the complexity of this structure means more components can be broken down or denatured, and as protein function depends on this structure integrity, protein drugs are difficult to store and maintain. The formulation of protein based drugs present the challenge of keeping the protein folded during isolation, manufacture, and patient use.

Protein drugs, which can be quickly digested and left useless if taken orally, generally must be given by injection. Proteins are very unstable in the gastrointestinal tract, being hydrolyzed and broken down by its acids and enzymes. The oral bioavailability can be as low as <1% due to the effect that their large size and hydrophillicity has on membrane permeability (MacNally & Park, 1990; Lee, Dodda-Kashi, Grass, & Rubas, 1990). Parenteral administration, which has 100% bioavailability, is usually the preferred method for delivering protein therapeutics.

Also, minimization of manufacturing costs while maintaining protein integrity is of paramount importance. Proteins in pharmaceutical compositions are typically packaged and stored in a lyophilized state to maintain their biological activity. Inherent physical instabilities of the polypeptides including denaturing, deamination, and the formation of soluble and insoluble aggregates have become a problem for the storage and handling of these therapeutics in liquid formulations. Factors such as pH, temperature, ionic strength, physical agitations, and cycles of freeze-thaw often result in the destabilization and loss of biological activity of the proteins. Lyophilization provides the protein in a dried form and involves freezing the protein at atmospheric pressure, removing the water in a low pressure chamber, and collecting the sublimed frozen water on a condenser. However, lyophilization requires more handling, increased processing time, a non-reactive and completely air-tight storage container, a sterile solvent during reconstitution, possibly a separate container for the sterile reconstitution solvent, and complex equipment including a drying chamber, condenser, vacuum pump, refrigeration system, and controller devices. It also must be reconstituted prior to injection, which requires a trained individual and time for the protein to go into solution completely. All of these factors increase the cost of manufacture and difficulty of parentaral administration of protein therapeutics in the powdered form.

Liquid formulation can eliminate the long, expensive lyophilization process in favor of a product that is much simpler for the end user to employ. Liquid formulations can be cheaper to manufacture and preferred by physicians. Unfortunately, any water molecules present tend to foster degradation of proteins. If the tendency towards protein degradation in liquid formulation can be overcome, the cost of protein therapeutics can be substantially reduced.

Accordingly, there is a need in the industry for novel formulations and compositions containing therapeutic proteins which promote the stability and maintain the biological activity of the proteins before administration to a patient.

The present invention addresses previous shortcomings in the art by providing compositions and methods for the preparation, stabilization, and/or storage of polypeptides, particularly therapeutic polypeptides.

SUMMARY OF THE INVENTION

A first aspect of the present invention is a parenterally injectable pharmaceutical composition comprising, consisting of or consisting essentially of:

(a) from 0.01 to 50 weight percent choline dihydrogen phosphate (CDHP);

(b) from 0 to 50 weight percent of a base (e.g., choline hydroxide, sodium hydroxide, etc.);

(c) at least 50 weight percent water;

(d) from 0.01 to 10 weight percent active compound (e.g. a protein or polypeptide active compound) selected from the group consisting of Interleukin-2, gelsolin, antibodies (e.g. monoclonal antibodies such as humanized monoclonal antibodies and including non-glycosylated antibodies); erythropoietin, interferon, human growth hormone, folicle stimulating hormone, and granulocyte colony stimulating factor; and (e) from 0, 0.01 or 0.1 to 30, 40 or 50 weight percent of at least one compatible osmolyte.

In some embodiments of the foregoing, the composition preferably has a pH of from 6 or 6.5 up to 7.5 or 8.

In some embodiments of the foregoing, the water is included in an amount of at least 60, 70 or 80 weight percent up to 95 or 99 percent.

In some embodiments of the foregoing, the base is included in an amount of not more than 20, 30 or 40 weight percent.

In some embodiments of the foregoing, the choline dihydrogen phosphate is included in an amount of not more than 20, 30 or 40 weight percent.

In some embodiments of the foregoing, the base and the choline dihydrogen phosphate are included together in a combined amount not more than 20, 30, 40 or 50 weight percent.

In some embodiments of the foregoing, the composition is a single phase solution.

In some embodiments of the foregoing, the composition has an osmolality of 100 to 700 milliOsmoles or 3,000 milliOsmoles.

In some embodiments of the foregoing, the active agent is Interleukin-2, such as human Interleukin-2 and particularly aldesleukin; in other embodiments, the active agent is gelsolin such as human gelsolin.

In some embodiments of the foregoing, the active agent is recombinant (e.g., a recombinant protein or peptide) and/or is non-glycosylated.

A further aspect of the invention is a composition as described herein packaged in a sterile container.

A further aspect of the invention is a method of treating a disorder in a subject in need thereof, comprising administering said subject a treatment effective amount of a composition as described herein.

A further aspect of the invention is a composition as described herein for use in treating a disorder in a subject in need thereof.

The foregoing and other aspects of the present invention will now be described in more detail with respect to other embodiments described herein. It should be appreciated that the invention can be embodied in different forms and should not be construed as limited to the embodiments set forth herein. Rather, these embodiments are provided so that this disclosure will be thorough and complete, and will fully convey the scope of the invention to those skilled in the art.

BRIEF DESCRIPTION OF THE DRAWINGS

FIG. 1 shows that freshly isolated splenocytes remain viable when exposed to 30 mM or less CDHP, $5 \times 10^5$ splenocytes were incubated 24 hours in complete medium containing increasing concentrations of CDHP. Cell viability was then measured by trypan blue (squares) or resazurin assays (triangle) and normalized with control splenocytes viability (CDHP viability/no CDHP viability*100). N=15 from 5 independent experiments.

FIG. 2 illustrates CDHP increases lysozyme stability. Thermal analysis was performed on 100 mg/ml lysozyme formulations, containing sodium acetate (FIG. 2a) or CDHP (FIG. 2b), stored at room temperature for one to three months.

DETAILED DESCRIPTION OF THE INVENTION

Figure 1:
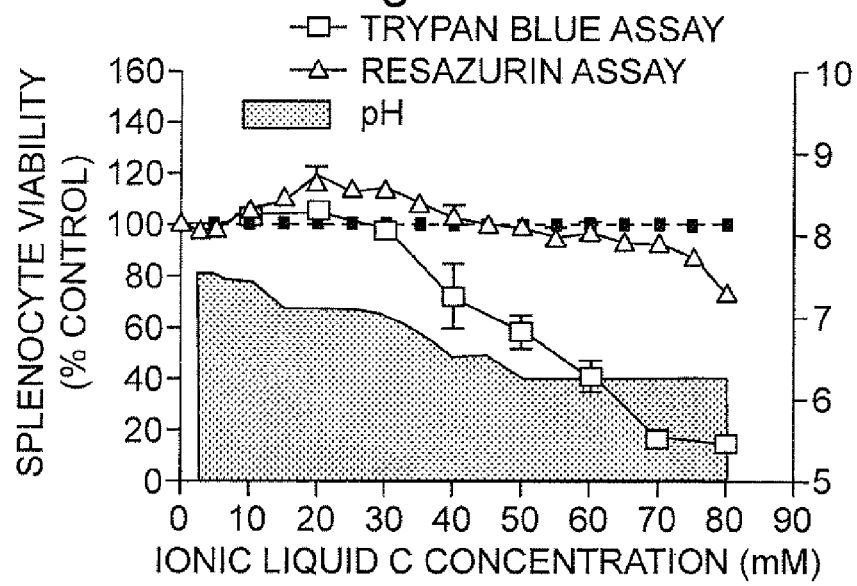
FIG. 1.

The present invention will now be described more fully hereinafter. This invention may, however, be embodied in different forms and should not be construed as limited to the embodiments set forth herein. Rather, these embodiments are provided so that this disclosure will be thorough and complete, and will fully convey the scope of the invention to those skilled in the art.

The terminology used in the description of the invention herein is for the purpose of describing particular embodiments only and is not intended to be limiting of the invention. As used in the description of the invention and the appended claims, the singular farms "a", "an" and "the" are intended to include the plural forms as well, unless the context clearly indicates otherwise.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the present application and relevant art and should not be interpreted in an idealized or overly formal sense unless expressly so defined herein. The terminology used in the description of the invention herein is for the purpose of describing particular embodiments only and is not intended to be limiting of the invention. All publications, patent applications, patents and other references mentioned herein are incorporated by reference in their entirety.

Also as used herein, "and/or" refers to and encompasses any and all possible combinations of one or more of the associated listed items, as well as the lack of combinations when interpreted in the alternative ("or").

Unless the context indicates otherwise, it is specifically intended that the various features of the invention described herein can be used in any combination.

Moreover, the present invention also contemplates that in some embodiments of the invention, any feature or combination of features set forth herein can be excluded or omitted. To illustrate, if the specification states that a complex comprises components A, B and C, it is specifically intended that any of A, B or C, or a combination thereof, can be omitted and disclaimed.

As used herein, the transitional phrase "consisting essentially of" (and grammatical variants) is to be interpreted as encompassing the recited materials or steps "and those that do not materially affect the basic and novel characteristic(s)" of the claimed invention. See, In re Herz, 537 F.2d 549, 551-52, 190 U.S.P.Q. 461, 463 (CCPA 1976) (emphasis in the original); see also MPEP §2111.03. Thus, the term "consisting essentially of" as used herein should not be interpreted as equivalent to "comprising."

The term "about," as used herein when referring to a measurable value such as an amount or concentration (e.g., the weight percent of the active compound in the composition) and the like, is meant to encompass variations of 20%, 10%, 5%, 1%, 0.5%, or even 0.1% of the specified amount.

In describing the invention, it will be understood that a number of techniques and steps are disclosed. Each of these has individual benefit and each can also be used in conjunction with one or more, or in some cases all, of the other disclosed techniques. Accordingly, for the sake of clarity, this description will refrain from repeating every possible combination of the individual steps in an unnecessary fashion. Nevertheless, the specification and claims should be read with the understanding that such combinations are entirely within the scope of the invention and the claims.

I. Definitions

"Polypeptide," "protein," and "peptide" as used herein refer to a chain of covalently linked amino acids. Unless otherwise indicated, the term "polypeptide" encompasses both peptides and proteins. In general, the term "peptide" can refer to shorter chains of amino acids (e.g., 2-50 amino acids); however, all three terms overlap with respect to the length of the amino acid chain. Polypeptides may comprise naturally occurring amino acids, non-naturally occurring amino acids, or a combination of both. The polypeptides may be isolated from sources (e.g., cells or tissues) in which they naturally occur, produced recombinantly in cells in vivo or in vitro or in a test tube in vitro, or synthesized chemically. Such techniques are known to those skilled in the art. See, e.g., Sambrook et al., Molecular Cloning: A Laboratory Manual 2nd Ed. (Cold Spring Harbor, N.Y., 1989); Ausubel et al. Current Protocols in Molecular Biology (Green Publishing Associates, Inc. and John Wiley & Sons, Inc., New York). Accordingly, "polypeptide," "protein," and "peptide" as used herein encompass all naturally occurring, synthetic, and recombinant polypeptides and biologically active variants thereof.

"Therapeutic protein", "therapeutically active polypeptide," "therapeutic polypeptide," and "therapeutic peptide" (and grammatical variations thereof) as used herein refer to polypeptides, proteins, peptides, or biologically active variants thereof which bring about a desired therapeutic response in a patient such as, for example, the prevention, treatment, or diagnosis of a disease or medical condition.

By the term "treat," "treating" or "treatment of" (and grammatical variations thereof) it is meant that the severity of the subject's condition is reduced, at least partially improved or ameliorated and/or that some alleviation, mitigation or decrease in at least one clinical symptom is achieved and/or there is a delay in the progression of the disease, disorder, or medical condition.

A "treatment effective" amount as used herein is an amount that is sufficient to treat (as defined herein) the subject, Those skilled in the art will appreciate that the therapeutic effects need not be complete or curative, as long as some benefit is provided to the subject.

"Acid" as used herein refers to various water-soluble compounds with a pH less than 7 that can be reacted with a base to form a salt. Exemplary acids can be monoprotic or polyprotic and can comprise one, two, three, or multiple acid functional groups.

"Organic acid" as used herein refers to an organic compound that is an acid, as defined herein. Exemplary organic acids include, but are not limited to carboxylic acids, sulfonic acids, alkanoic acids, and halogenoalkanoic acids. Organic acids suitable for use according to certain non-limiting embodiments may include, but are not limited to, lactic acid, citric acid, formic acid, acetic acid, propionic acid, butanoic acid, uric acid, ascorbic acid, triflic acid, oxalic acid, malic acid, succinic acid, fumaric acid, ascorbic acid, tartaric acid, glucono delta-lactone, and combinations thereof.

"Base" as used herein refers to a compound with a pH more than 7 that can be reacted with an acid to form a salt. Exemplary bases include, but are not limited to: (i) oxides, such as metal oxides, (ii) hydroxides, such as organic and inorganic (e.g., metal) hydroxides, (iii) amines or amine functionalized molecules, (iv) salts of organic acids (eg metal salts of carboxylic acids), (v) amino acids, etc.

"Compatible osmolyte" as used herein refers to a compound such as an amino acid (including derivatives thereof), polyols, and methyl amines. Particular examples include, but are not limited to, sarcosine, betaine, glycine-betaine, myo-inositol, glycine, proline, glycerol, glucose, dissacharides such as trehalose, mannitol, etc. A compatible osmolyte may be used individually or in combination with others "Organic salt" as used herein refers to an ionic compound that is a salt and comprises an organic ion. Exemplary organic salts include, but are not limited to, carboxylates, such as formate, lactate, acetate, propanoate and benzoate and sulphonates, such as mesylate, triflate, tosylate, and besylate. Organic salts suitable for use according to certain non-limiting embodiments may include, but are not limited to, ethylammonium nitrate (hereinafter referred to as "BAN"), dimethylammonium hydrogen sulfate (DMAHSO4), dimethylammonium triflate (TEATf), triethylammonium methane sulfonate (TEAMs), choline dihydrogen phosphate (CDHP), and related compounds.

"Ionic liquid" as used herein refers to a substance composed only of ions that remains in the liquid state below the boiling point of water and more preferably at room temperature. Ionic liquids are low melting point (typically less than about 100° C.) compounds made of a cation and an anion. These non-aqueous polar solvents have a very low vapor pressure, can solvate a wide variety of compounds, and are thermally, electrically, and chemically stable. They are organic salts, as defined herein, which are larger and more complex than common salts, such as sodium chloride. A delocalization of charge on the anion limits their ability to form a crystal lattice easily, resulting in a low melting point. At room temperature, their ions are organized in a less compact manner and are free to interact with any solutes present. Ionic liquids can thus replace water and other solvents in a range of applications, such as, but not limited to protein-based pharmaceutical formulations intended for parenteral injection.

The anion and cation choice of the ionic liquid can be tailored to provide desired solvent characteristics, such as polarity, viscosity, hydrogen bonding capacity, miscibility, and conductivity. Ionic liquid properties (polarity, miscibility, hydrophobicity, etc.) can be tailored by varying the properties of the cation and anion, such as, but not limited to, varying the side chain length of the cation and the type of anion (Fujita, MacFarlane, & Forsyth, 2005) (Fujita, Forsyth, MacFarlane, Reid, & Elliott, 2006). In some embodiments of the present invention, the ionic liquid can be tailored to interfere positively with hydrogen bonding as well as electrostatic and hydrophobic interactions that govern the protein function.

Non-limiting examples of ionic liquids which are included as aspects of the present invention include ethylammonium nitrate (hereinafter referred to as "EAN"), dimethylammonium hydrogen sulfate (DMAHSO4), dimethylammonium triflate (TEATf), triethylammonium methane sulfonate (TEAMs), and related compounds.

"Hydrated ionic liquid" as used herein refers to a mixture of water and an organic salt, as defined herein, that is liquid at room temperature.

II. Compositions

The present invention describes compositions and methods relating to the preparation, stabilization, and/or storage of polypeptides, such as, but not limited to, therapeutic polypeptides. In certain embodiments of the present invention, the composition provides for the preservation and sustained activity of therapeutic polypeptides. In particular embodiments, the composition is suitable for parenteral injection.

In some embodiments of the present invention, the composition comprises, consists of, or consists essentially of an organic salt (which may or may not be liquid at room temperature) and water. In other embodiments of the present invention, the composition comprises, consists of, or consists essentially of an organic acid, an organic salt (which may or may not be liquid at room temperature), and water. Preferably the organic acid and organic salt are a conjugate acid base pair, but this need not necessarily be the case. Any suitable biocompatible acid and salt can be mixed to form the medium of utility in this invention. Mixing of the organic acid and organic salt can provide the optimal proton activity in the medium for the purposes of stabilization of the dissolved protein. Each protein has a different response to proton activity (related to its isoelectric point). In certain embodiments of the present invention, the composition provides an adjustable medium that can be tuned to the optimum proton activity for each protein by varying the acid/salt ratio. In other embodiments, the pH of the composition can be adjusted to reduce pain and injury at the injection site for parenteral injections of the composition.

The compositions of the present invention can comprise an organic salt and/or an organic acid in an amount of about 0 to about 50 weight percent of the composition. In particular embodiments of the present invention the organic salt is choline dihydrogen phosphate.

In some aspects of the invention a base can be present in an amount of about 0 to about 50 weight percent of the composition. In particular embodiments of the present invention the base is choline hydroxide.

The composition can comprise water in an amount of about 7 percent to about 100 percent, about 20 percent to about 100 percent, or about 50 percent to about 100 weight percent of the composition. The water content of the mixture can be independently varied to provide the optimal combination of stabilization versus solubility. Water is not actually homogenous on a nanoscopic level, but consists of clusters of water molecules in low and high density arrangements. It is more likely to form hydrogen bonds with other water molecules than hydrophobic substances. When hydrophobic substances come in contact with water molecules, the water molecules form low density water (LDW) clathrate, or cage-like water molecule structures around them. These highly ordered water structures serve to decrease the entropy of the system.

In terms of a biological molecule, one can view entropy as a measure of molecular disorder or a measure of how many ways the molecule can arrange itself in order to absorb heat energy as its temperature is raised to a certain temperature. Entropy, $\Delta S$, is defined as the differential amount of heat transfer during an internal reversible process, $\delta Q$, divided by the temperature, T, of the boundary at which the heat transfer occurs.

Hydrophobic groups of a protein tend to pack together in the protein core when in an aqueous solvent, allowing solvent water molecules more freedom of motion. This increases the entropy of the water, and thus of the whole protein-solvent system. Therefore, this hydrophobic effect is governed by the second law of thermodynamics wherein the entropy of the system increases during folding. It should be noted however, that internal water does exist, creating hydrogen bonds between charged interior, hydrophilic groups. This allows a certain amount of necessary internal motion.

Protein stability is influenced not only by its interaction with water, but by how any other co-solvent molecules present interact with the water molecules around the protein. Salts are ionic compounds that can be used as co-solvents in aqueous protein liquid formulations. Ionic co-solvents may be classified as kosmotropic or chaotropic, depending on whether they encourage the formation of LDW or high density water (HDW). "Kosmotropes" are compounds that interact strongly with water molecules, and organize water molecules in a typically favorable manner around protein molecules. "Chaotropes" are compounds that interact weakly with water molecules and disrupt the water molecule hydrogen bonded network around protein molecules.

High density water, HDW, describes the organization of water molecules when they interact more strongly with another hydrophilic molecule than with each other. Water molecules arrange themselves in such a way as to maximize the amount of interaction with the hydrophilic substance, leading to weaker, bent or broken hydrogen bonding between each other. HDW is encouraged by the presence of ionic kosmotropes. Compounds labeled as ionic kosmotropes are small, multiple charged ions with a high charge density that interact very strongly with water molecules. Kosmotropes are typically anions, because anions are more strongly hydrated than similarly charged, bulkier, larger cations. It is generally accepted that kosmotropes stabilize proteins by organizing water molecules a preferential manner.

By comparison, ionic chaotropes do not interfere with hydrogen bonding between water molecules, because they are large, singly charged, and have a low charge density. Their weak interaction with water encourages the formation of LDW. The ionic chaotrope is free to interact with the protein, whether positively or negatively. It has been shown that a combination of kosmotropic anions and chaotropic cations tend to stabilize proteins, so a stabilizing medium should have a balance of the two.

Choice of ionic liquid should be made with consideration of the individual protein-medium-substrate relationship. Although some ionic liquids stabilize proteins at higher temperatures as shown by an increased transition temperature and enthalpy of unfolding, some do not. Many ionic liquids must be hydrated to some extent in order to stabilize proteins. They must partition the essential amount of water in the correct, organized fashion around the protein in order to maintain activity. A certain amount of water is typically needed for protein function and structure, but more water beyond the solvation layer at the surface may lead to destabilization. The role of hydration has been explored in a study of imidazolium based ionic liquids, which reveals an optimal 7.5% hydration to reduce thermal denaturation, while 0% hydration lead to an un-dissolved, kinetically trapped protein. Without wishing to be bound to a particular theory, ionic liquids may stabilize proteins by stripping off most of the water from the protein surface, leaving only the essential water arranged in small clusters.

As stated before, proteins are generally stabilized by a combination of kosmotropic anions and chaotropic cations. Without wishing to be bound to a particular theory, the anion choice appears to have a stronger effect on the ability of an ionic liquid to stabilize a protein. Table 1 ranks different ions based on their B-coefficients. A higher B-coefficient indicates a higher kosmotropicity. The ability of the anion to stabilize proteins is closely related to the Hoffmeister series (Micaelo & Soares, 2008).

TABLE 1

B-coefficients of various ions used in ionic liquids (Kosmotropicity increasing with increasingly positive B-coefficient).

| Anion | B-coef. | Cation | B-coef. |
|---|---|---|---|
| $PO_4^{3-}$ | 0.495 | $(CH_3)_4N^+$ | 0.123 |
| $H_2PO_4^-$ | 0.34 | $K^+$ | 0.009 |
| $CH_3COO^-$ | 0.246 | $Na^+$ | 0.085 |
| $SO_4^{2-}$ | 0.206 | $MePy^+$ | 0.144 |
| $Br^-$ | 0.033 | $Li^+$ | 0.146 |
| $Cl^-$ | 0.005 | $EtPy^+$ | 0.228 |
| $OTs^-$ | −0.073 | $Ca^{2+}$ | 0.284 |
| $BF_4^-$ | −0.093 | $Mg^{2+}$ | 0.385 |
| $PF_6^-$ | −0.21 | $BuPy^+$ | 0.396 |
| | | $Al^{3+}$ | 0.744 |

Other aspects of the present invention provide compositions that comprise polypeptides. In some embodiments, the composition comprises, consists of, or consists essentially of a therapeutically active polypeptide, an acid, an organic salt of the conjugate anion, and water. In other embodiments, the composition comprises, consists of, or consists essentially of a therapeutically active polypeptide, an organic salt and water. A base can, in some embodiments, be added to the composition. In particular embodiments of the present invention, the acid/salt ratio of the composition is such that proton activity is optimal for the therapeutic protein and/or parenteral delivery.

Exemplary therapeutic polypeptides include, but are not limited to, enzymes and antibodies, such as monoclonal antibodies, polyclonal antibodies, humanized monoclonal antibodies, and non-glycosylated antibodies. Specific examples of therapeutic polypeptides include, but are not limited to, interleukin-2 and gelsolin.

In certain embodiments of the present invention, the composition comprises, consists of, or consists essentially of ionic liquids, such as, but not limited to, ethylammonium nitrate and a therapeutic polypeptide.

In other embodiments of the present invention, the composition comprises, consists of, or consists essentially of choline dihydrogen phosphate ("CDHP") and a therapeutic polypeptide. Choline dihydrogen phosphate (CDHP) is a hydrophilic combination of a biocompatible and kosmotropic anion, dihydrogen phosphate (dhp), and a cation, choline, which occurs naturally in biological systems (Scheme 1).

Scheme 1: Structures of choline and dihydrogen phosphate (dhp).

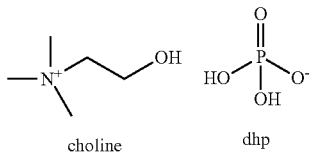

CDHP is not technically an ionic liquid, having a melting temperature slightly above 100° C., but is an organic salt. Thermal gravimetric analysis shows it to be stable up to 200° C. (Yoshizawa-Fujita, Fujita, MacFarlane, & Forsyth, 2007). CDHP is liquid at room temperature when hydrated to an optimal concentration of 80% w/w CDHP (that is, 80 parts CDHP to 20 parts water by weight). Because of its large size, choline is usually considered to be quite a chaotropic cation, but the hydroxyl group increases its ability to hydrogen-bond with water. The kosmotropicity of dhp is influenced by the presence of free electrons on the oxygen atom, which increases its ability to form hydrogen bonds with water molecules. Kosmotropic effects are typically in reference to solutes dissolved in water, but it is assumed to be applicable or at least correlated, when water is acting as the solute and an ionic liquid is acting as the solvent (Fujita K., et al., 2007).

III. Methods of Preparation

Methods of preparing the compositions of the present invention are known in the art and described herein. In preparing the compositions of the present invention, the following factors or components can be considered, adjusted, and/or added to the composition.

Buffering the pH.

As a protein interacts with its environment, it will release or accept hydrogen atoms depending on the nature of the solution. To protect against a detrimental pH change, a suitable buffer will accept or donate hydrogen atoms in order to keep the pH stable. Its maximum buffering capacity should be at the pH at which the protein is structurally stable, should not act as a substrate, and should not be temperature dependent (Branchu, 1999) (Ugwu & Apte, 2004).

Sugars.

In nature, sugars have been found to preserve proteins in a glassy state, and this principle has been transferred to protein cryopreservation. Trehalose, a disaccharide, stabilizes proteins during freeze drying and high temperature exposure, and acts as a protectant in temperature extreme resistant organisms. For example, addition of trehalose to a protein solution increases the temperature at which the first stage of hen egg white lysozyme (HEWL) heat denatures (Hedoux, et al., 2006).

Polyols.

Polyols (sugar alcohols), such as mannitol, glycerol, and propylene glycol have also been determined to stabilize proteins, such as HEWL, as shown by a higher thermal transition midpoint temperature and enthalpy of unfolding (Cioci & al., 1996) (Singh & Singh, 2003). Two theories are proposed for this occurrence. Without being bound to either theory, the first suggests that unfolding is less favorable when polyols are present. Mannitol, for example, is superior for preventing aggregation. The second suggests that polyols form hydrogen bonds with protein surface groups, restricting conformational changes and protecting buried hydrophobic groups from exposure to denaturation. (Singh & Singh, 2003)

Amino Acids and Polyamines.

Amino acids have been used as additives to stabilize proteins in many studies (Cioci & al., 1996). For example, histidine protects proteins by acting as an antioxidant. Polyamines, organic compounds having two or more amino groups, have also had considerable stabilizing success. When spermine, a low molecular weight polyamine, binds to HEWL both thermal stability and enzyme activity is increased (Powroznik, 2004).

De-Stabilizers.

Urea and guanine hydrochloride are well known protein denaturants. Interestingly, at concentrations that are low enough not to lead to denaturation, these, unlike the non-denaturant additives covered above, can enhance solubility through increased hydrogen bonding between the denaturant and the protein (Cioci & al., 1996) (Hirano, Hamada, Okubo, Noguchi, Higashibata, & Shiraki, 2007).

Concentration Effects.

While it is of interest to find a highly concentrated liquid protein formulation to increase the ease and convenience of protein based drug administration, the effects of concentration on protein stability must be acknowledged. These effects are not well understood, because most stability studies have typically been carried out on dilute (<1 mg/ml) concentrations. Certainly proteins in physiological conditions are stable in high concentrations. Hemoglogin, for example, exists in human blood at 300 g/L (Guo, Ham, Robbins, & Doug, 2006).

It is known that crowding of inert macromolecules, which do not directly interact with the protein, may have a stabilizing effect on proteins. Excluded volume theory explains this as the result of the preference for a more compact, native protein conformation in a crowded environment. It is not clear whether this theory translates for high protein concentrations as opposed to high inert macromolecule concentrations (Guo, Ham, Robbins, & Doug, 2006). Dilute protein solutions are stabilized primarily through intra-molecular interactions and hydration effects, while concentrated protein solutions may be stabilized through protein-protein interactions. Intra-molecular interactions in concentrated solutions may be affected by changes in hydration, van der Waals forces, and covalent alterations (peptide and disulfide bonds, deamidation, oxidation). Guo, et al tested the stability of high concentrations (on the order of 350 mg/ml) of lysozyme, hemoglogin, bovine serum albumin, and bovine fibrinogen in comparison to dilute concentrations of 1 mg/ml. Spectroscopic and calorimetric measurements revealed a protein specific relationship between stability and concentration. For example, the thermal transition midpoint temperature of lysozyme and BSA decreased at the higher concentration (~5° C. and 23° C., respectively), while the transition temperature of hemoglobin and fibrinogen increased (8° C. and 3° C., respectively) (Guo, Ham, Robbins, & Doug, 2006). It should be noted, however, that these proteins were dissolved in an aqueous solvent. Clearly, the protein concentration-stability relationship is not completely characterized and requires continued investigation.

IV. Subjects and Administration

The present invention is primarily concerned with the treatment of human subjects, but the invention may also be carried out on animal subjects, particularly mammalian subjects such as dogs, cats, livestock and horses for veterinary purposes. While subjects may be of any suitable age, the subjects are in some embodiments neonatal, infant, juvenile, adolescent, adult or geriatric subjects.

The compositions of the invention include those suitable for oral, parenteral (e.g., subcutaneous, intramuscular, intradermal, or intravenous), topical (i.e., both skin and mucosal surfaces, including airway surfaces) and transdermal administration, although the most suitable route in any given case will depend on the nature and severity of the condition being treated and on the nature of the particular active compound which is being used.

In general, the composition, including the active agent, may be packaged in sterile form in a sterile container such as a vial, syringe (for injection) etc. Depending upon the particular active agent (for example, IL-2 tends to have shorter shelf lives in liquid form), the composition preferably has a shelf life in packaged form of at least 2, 3 or 4 days, up to 1, 2 or 3 weeks or one month, or in some embodiments (particularly for more stable active agents) a shelf life in packaged form of at least one or two months up to 6 months or one to two years, or more, at a temperature of 37° C. "Shelf life" has its conventional meaning in the art and refers to the time period during which the active agent retains sufficient activity for accurate and effective administration thereof, and the formulation retains sufficient stability (e.g., a single phase solution remains as a single phase solution) for accurate and effective administration thereof at the recited temperature conditions.

Disorders for which the compositions of the invention are useful for treating are determined by the active agent contained therein. For example: Interleukin-2 (e.g., human Interleukin-2) is useful for treating conditions including, but not limited to, cancer, viral infection, and as a vaccine booster or adjuvant. Gelsolin (e.g., human Gelsolin) is useful for treating conditions such as cystic fibrosis (and particularly as an aerosol-delivered mucolytic therein). Antibodies (particularly monoclonal antibodies) are useful in treating or preventing conditions including cancer and autoimmune disease. Insulin, (e.g., human insulin) is useful for treating diabetes (including both type I and type II diabetes). Erythropoietin (e.g., human recombinant erythropoietin) is useful for treating anemia. Growth hormone (e.g., human growth hormone) is useful for treating and/or preventing conditions including, but not limited to, Turner syndrome, chronic renal failure, Prader-Willi syndrome, intrauterine growth retardation, severe idiopathic short stature, maintaining muscle mass in wasting due to AIDS, hort bowel syndrome multiple sclerosis, obesity, fibromyalgia, heart failure, Crohn's disease and ulcerative colitis, burns, etc. Folicle stimulating hormone (e.g. human folicle stimulating hormone) is useful for stimulating the development of germ cells in both males and females. Granulocyte-colony stimulating factor or G-CSF (particularly human G-CSF) is useful for stimulating the development of white blood cells (e.g., for treating neutropenia after chemotherapy in cancer patients).

The therapeutically effective dose or treatment effective amount of any specific compound, the use of which is in the scope of present invention, will vary from compound to compound and patient to patient, and will depend upon the disorder being treated, condition of the patient and the route of delivery. As a general proposition, a dose of the active agent of from about 0.05 or 0.1 up to about 50 or 100 mg/kg subject body weight is used.

The present invention is explained in greater detail in the following non-limiting Examples.

Example 1

By way of example, hydrated IL CDHP+water 80/20 has a proton activity equivalent to pH=~5.2 when present in dilute aqueous solution. By addition of choline monohydrogen phosphate, or choline hydroxide or any other slightly basic salt such as choline tartarate, the proton activity of this can be adjusted to around neutral. A mixture of 4:1 CDHP+ Choline hydroxide (with 20% water) molar ratio provides the equivalent of pH ~7.2.

Methods of measurement of proton activity in concentrated acid/salt mixtures are not routinely available and we refer here to the equivalent dilute aqueous pH values obtained by diluting the medium with excess water and then performing a traditional glass electrode measurement of pH.

Stabilization of IL-2 Using Choline Dihydrogen Phosphate (CDHP).

Recombinant interleukin-2 (rIL-2) therapy has been demonstrated to elicit remission of several human tumors, including metastatic renal cell cancer (RCC) and malignant melanoma. High-dose, bolus rIL-2 (i.v.) is approved in the US for these two indications, based on evidence of rIL-2-induced durable cancer remission in a significant number of patients (5-10%) (Sparano, Fisher et al. 1993). The biological functions of IL-2 on anti-tumor effector cells have been extensively investigated. IL-2 activates numerous critical cells in the immune system, acting as an autocrine factor to drive the expansion of tumor-specific helper and cytotoxic T cells (Th, CTLs), and as a paracrine factor acting on other immune cells (e.g., B cells, Natural killers, lymphokine associated killer cells) involved in killing tumorigenic cells (Bamford, Grant et al. 1994; Waldmann, Dubois et al, 2001). More recently, IL-2 has been reported to be critical in maintaining "peripheral tolerance" by enhancing T cell (Treg) survival and function. One mechanism by which Treg cells contribute to the maintenance of homeostasis is by limiting IL-2 availability via constitutive, high affinity IL-2 receptor expression (Viguier, Lemaitre et al. 2004; Fontenot, Dooley et al. 2005).

IL-2 is a single 133 amino acid polypeptide of molecular weight 15.5 kDa containing two sets of α-helical domains required for receptor binding/activation (Korner, Dettmer et al. 1986; Bazan 1992). Storage of IL-2 in aqueous solution makes it susceptible to deamination of an asparagine residue at position 88. At temperatures in excess of 44° C. IL-2 undergoes irreversible denaturation and aggregation in solution (Sasaoki, Hiroshima et al. 1992). These physicochemical properties necessitate IL-2 to be freshly prepared prior to clinical use. In addition, IL-2 activity is decreased in acidic conditions (Ricci, Sarkar et al. 2003). Therefore bolus intravenous (i.v.) injections are commonly used. Following i.v. administration, the pharmacokinetic profile of rIL-2 is characterized by a high plasma concentration that declines in a bi-modal exponential form. The initial elimination phase of IL-2, due to extracellular distribution and renal elimination, was reported to have a plasma half-life of 7-14 minutes. The second phase of elimination, which is attributed solely to renal excretion, is slower with an estimated terminal plasma half-life of 85 minutes (Konrad, Hemstreet et al. 1990). To compensate for rapid IL-2 elimination, high IL-2 doses (600,000 U/kg) are repeatedly injected into patients (up to 6 injections at 8 hour intervals) undergoing IL-2 immunotherapy.

Ionic liquids are materials that have ionic characteristics, yet are liquid at room temperature. Depending on the specific combinations of anions and cations in the mixture, the hydrogen bonding and water miscibility can effectively be "tuned" to the requirements of the solution (Yang 2009). In recent years several studies have reported the preservation and sustained activity of biological enzymes and proteins in these ionic liquids (Feher, Major et al. 2007). In hydrophilic ionic liquids, cations and anions play an important role in protein and enzyme stabilization in the presence of water. A combination of chaotropic (weakly hydrated) cations and kosmotropic (strongly hydrated) anions represent the best stabilizing solution studied to date (Zhao 2005). Ionic liquids are traditionally synthesized from imidazolium-based cations and highly fluorinated anions. More recent developments have demonstrated that ionic liquids can also be formulated from salts, sugars, amino acids and "biomolecules" that already have approval for use as pharmaceutical excipients (Fujita, Forsyth et al. 2006). Salts of the dihydrogen phosphate anion mixed with small quantities of water have demonstrated capabilities to dissolve moderate quantities of cytochrome c, lysozyme, RNase A, and cellobiose dehydrogenase (Fujita, MacFarlane et al. 2005; Constantinescu, D. et al., 2007). Furthermore the proteins were shown to retain structural integrity and biological activity under these conditions. In addition, these proteins retained their structure at much higher temperatures than are observed when formulated in standard aqueous solutions.

A panel of choline compounds was initially screened for biocompatibility using a resazurin fluorometric assay with mouse macrophages (J774) as the cell line. These data demonstrated that choline dihydrogen phosphate "CDHP" had the highest $EC_{50}$. This compound was then tested for cytotoxicity towards primary splenocyte cultures. Cell viability was then measured at 24 h by trypan blue exclusion or with a resazurin fluorometric assay. Splenocyte viability was not significantly altered at concentrations below 30 mM (FIG. 1). Interestingly, at doses >30 mM Choline-DHP cytotoxicity markedly increased and was associated with a drop in culture medium pH below 7. To confirm the data parallel experiments were performed using non-hematopoietic (B16-F10 melanocytes) cell lines from which similar results were obtained.

Figure 2:
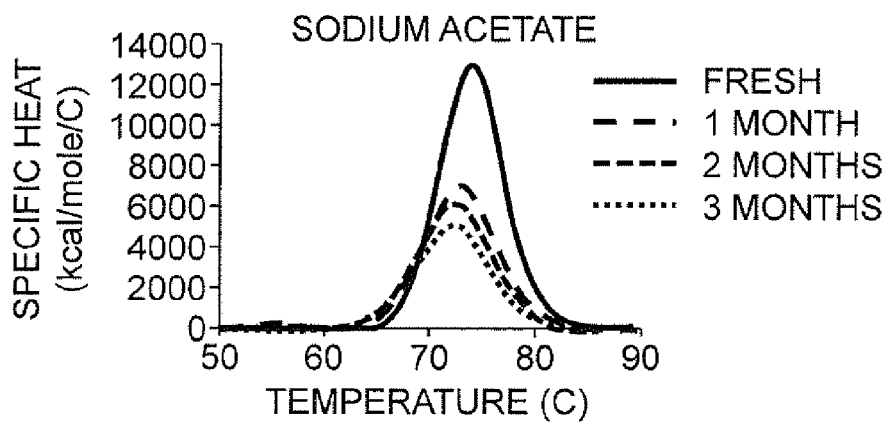
FIG. 2.
Figure 2:
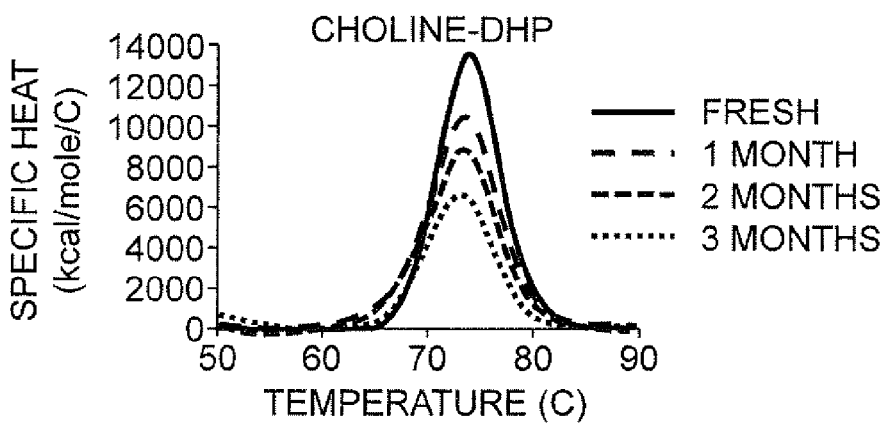

Proteins are generally active in the native, folded state and lose function when they unfold. Exposing a protein system to an increase in temperature perturbs the thermodynamic equilibrium between these two states. The denaturation temperature (or melting temperature) $T_m$ of a protein indicates the point at which half the protein sample is folded and half is denatured or unfolded. An increase in the $T_m$ is generally indicative of an increase in thermal stability. The area under the curve in a thermal scan can be integrated to determine the enthalpy of unfolding, DH. We have observed an increase in both Tm and ΔH of lysozyme solutions as the protein is formulated with increasing amounts of CDHP consistent with increased thermal stability of the protein in the presence of this compound. We have also performed shelf-life studies of lysozyme formulated in CDHP/water mixtures (80% CDHP wt/wt) and compared the activity to formulations stored in 0.1M sodium acetate, pH 4.0 (control) for 1-3 months at room temperature. In these studies, the samples were diluted back into buffer prior to analysis to determine if the protein was still in its native functional state. As observed in FIG. 2, the CDHP samples yielded a superior shelf-life as evidenced by retention of a higher fraction of folded protein (shown by a higher Cp signal) at equivalent time points Enzymatic assays of functionality confirmed these observations.

Figure 3:
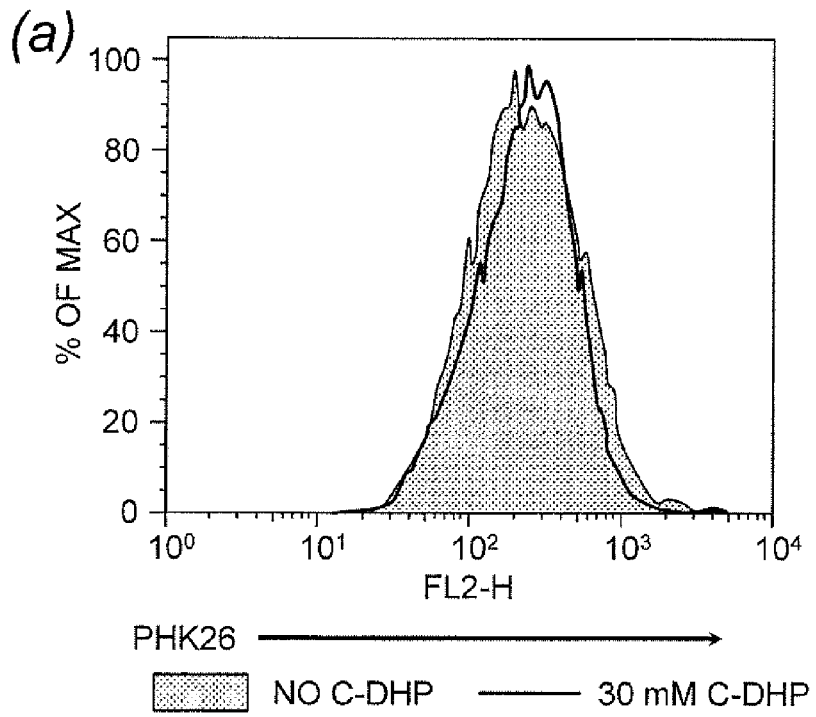
FIG. 3. CDHP does not impact interleukin-2 (IL-2) thermo-stability but increases IL-2-dependant HT-2 cell viability under buffered conditions in vitro. A and B. HT-2 cells were stained with PKH26 and incubated with IL-2 (100U) in complete RPMI 1640 buffered medium containing 0 or 30 mM CDHP. At T+72 h, cell proliferation was quantified by flow cytometry and cell viability measured based on morphological criteria. CDHP did not significantly affect IL-2-induced HT-2 lymphocyte proliferation under buffered conditions but significantly improved cell viability. n=9 from 3 independent experiments.
Figure 3:
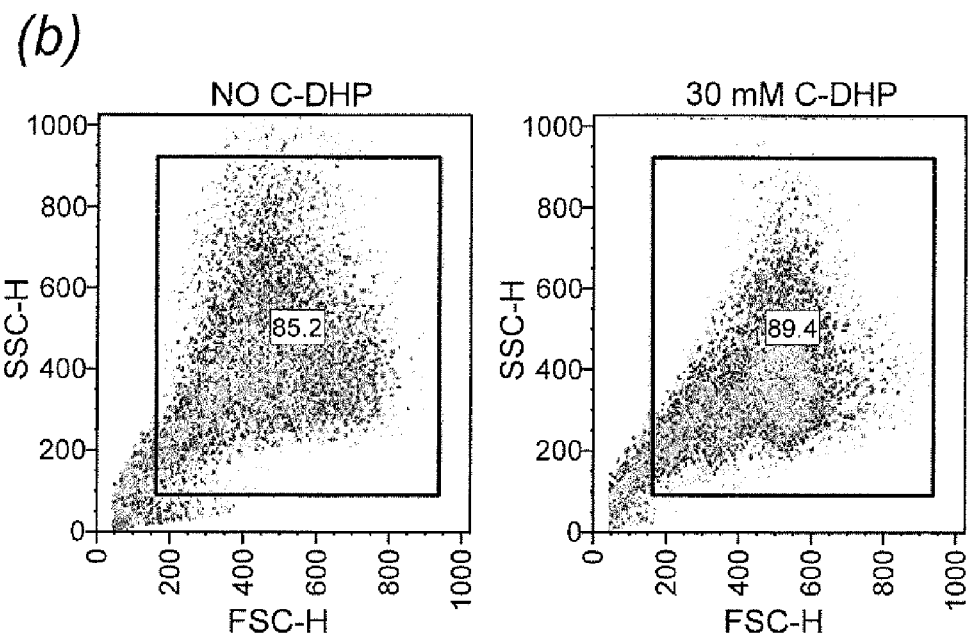

To determine if CDHP alters inherent IL-2 activity, we performed a series of cell proliferation assays using the HT-2 cell line (a mouse T helper cell line which requires exogenous IL-2 to survive and proliferate). Preliminary analysis confirmed that CDHP (0-30 mM) was not cytotoxic in this cell line (data not shown). Subsequently, HT-2 cell proliferation was stimulated using rIL-2 (10 or 100 U/ml) in the absence or presence of CDHP (15 or 30 mM). To perform proliferation analysis HT-2 cells were stained with PKH26 (a red fluorescent dye that coats the cell membrane) prior to cell culture. As the cells undergo division, the fluorescence detected (FACS) decreases logarithmically. Using this approach we demonstrated that HT-2 cell proliferation increased in a dose dependant manner with increasing exposure to r-IL-2 (FIG. 3). The addition of CDHP to the culture medium did not significantly reduce rIL-2-induced HT-2 proliferation (FIG. 3), but actually increased it.

REFERENCES

1. Angell et al. International Patent Application Serial No. PCT/US2008/071254, published as WO 2009/015367 A2 on Jan. 29, 2009.
2. Baker, S. N., McCleskey, T. M., Pandey, S., and Baker, G. A., 2004, "Fluorescence Studies of Protein Thermostability in Ionic Liquids," Chem. Commun. (Cambridge), 8, pp. 940-941. [MEDLINE] first citation in article
3. Fujita, K., MacFarlane, D. R., and Forsyth, M., 2005, "Protein Solubilising and Stabilizing Ionic Liquids," Chem. Commun. (Cambridge), 38, pp. 4804-4806. [MEDLINE] first citation in article
4. Fujita, K., Forsyth, M., MacFarlane, D. R., Reid, R, W., and Elliott, G. D., 2006, "Unexpected Improvement in Stability and Utility of Cytochrome C by Solution in Biocompatible Ionic Liquids," Biotechnol, Bioeng., 94(6), pp. 1209-1213. [MEDLINE] first citation in article
5. Byrne, N., Wang, L.-M., Belieres, J.-P., and Angell, C. A., 2007, "Reversible Folding-Unfolding, Aggregation Protection, and Multi-Year Stabilization, in High Concentration Protein Solutions, Using Ionic Liquids," Chem. Commun. (Cambridge), 26, pp. 2714-2716. [MEDLINE] first citation in article
6. Cooper, A., Nutley, M. A., and Wadood, A., 2000, "Differential Scanning Microcalorimetry," Protein-Ligand Interactions: Hydrodynamics and calorimetry, B. Z. Chowdhry and S. E. Harding, eds., Oxford University Press, Oxford, N.Y., pp. 287-318. first citation in article
7. Spinozzi, F., Ortore, M. G., Sinibaldi, R., Mariani, P., Esposito, A., Cinelli, S., and Onori, G., 2008, "Microcalorimetric Study of Thermal Unfolding of Lysozyme in Water/Glycerol Mixtures: An Analysis by Solvent Exchange Model," J. Chem. Phys., 129, p. 035101, [MEDLINE] first citation in article
8. Fraser, K. J., Izgordina, E. I., Forsyth, M., Scott, J. L., and MacFarlane, D. R., 2007, "Liquids Intermediate Between 'Molecular' and 'Ionic' Liquids: Liquid Ion Pairs?" Chem. Commun. (Cambridge), 37, pp. 3817-3819. [MEDLINE] first citation in article
9. Ranke, J., Molter, K., Stock, F., Bottin-Weber, U., Poczobutt, J., Hoffmann, J., Ondruschka, B., Filser, J., and Jastorff, B., 2004, "Biological Effects of Imidazolium Ionic Liquids With Varying Chain Lengths in Acute *Vibrio Fischeri* and WST-1 Cell Viability Assays," Ecotoxicol, Environ. Saf., 58, pp. 396-404. [MEDLINE] first citation in article
10. Brown, D. M., Donaldson, K., and Stone, V., 2004, "Effects of PM10 in Human Peripheral Blood Monocytes and J774 Macrophages," Respir. Res., 5(9), pp. 5-29. first citation in article
11. Wright, E. L., Quenell, D. C., Suling, W. J., and Barrow, W. W., 1996, "Use of Mono Mac 6 Human Monocytic Line and J774 Murine Macrophage Cell Line in Parallel Antimycobacterial Drug Studies," Antimicrob. Agents Chemother., 40(9), pp. 2206-2208. [MEDLINE] first citation in article
12. Jiang, G., Woo, B. H., Kang, F., Singh, J., and DeLuca, P. P., 2002, "Assessment of Protein Release Kinetics, Stability and Protein Polymer Interaction of Lysozyme Encapsulated Poly(D,L-lactide-co-glycolide) Microspheres," J. Controlled Release, 79, pp. 137-145. [MEDLINE] first citation in article
13. Bradford, M., 1976, "A Rapid and Sensitive Method for the Quantitation of Microgram Quantities of Protein Utilizing the Principle of Protein-Dye Binding," Anal. Biochem., 72, pp. 248-254. [ISI] [MEDLINE] first citation in article
14. Shugar, D., 1952, "The Measurement of Lysozyme Activity and the Ultra-Violet Inactivation of Lysozyme," Biochim. Biophys. Acta, 8, pp. 302-309. [MEDLINE] first citation in article
15. Stolte, S., Arning, J., Boffin-Weber, U., Matzke, M., Stock, F., Thiele, K., Uerdingen, M., Welz-Bierman, U., Jastorff, B., and Ranke, J., 2006, "Anion Effects on the Cytotoxicity of Ionic Liquids," Green Chem., 8, pp. 621-629. first citation in article
16. Nockemann, P., Thijs, B., Driesen, K., Janssen, C. R., Van Hecke, K., Van Meervelt, L., Kossmann, S., Kirchner, B., and Binnemans, K., 2007, "Choline Saccharinate and Choline Acesulfamate: Ionic Liquids With Low Toxicities," J. Phys. Chem. B, 111, pp. 5254-5263. first citation in article
17. Micaelo, N. M., and Soares, C. M., 2008, "Protein Structure and Dynamics in Ionic Liquids. Insights from Molecular Simulation Studies," J. Phys. Chem. B, 112, pp. 2566-2572.
18. Fujita et al. Choline dihydrogen phosphate. Acta Crystallographica Section E Structure Reports Online ISSN 1600-5368. 2009. P709.

Example 2

The objective of this study is to evaluate the stabilizing effect of choline dihydrogen phosphate (CDHP), a biocompatible organic salt, on the long term thermal stability of hen egg white lysozyme (HEWL), a well characterized protein. Microcalorimetry was implemented to determine the dependence of specific heat ($C_p$) on temperature for a range of formulations. Integration and analysis of this data enabled a determination of the change in enthalpy ($\Delta H$), entropy ($\Delta S$), and Gibbs free energy ($\Delta G$) of protein unfolding. Enzyme activity/protein functionality was assessed using a bacterial lysis turbidimetric assay. This study revealed that 80% w/w CDHP hydrated with water improved shelf life of 10 and 100 mg/ml formulations of HEWL when compared to the best known aqueous buffer as evidenced a higher folded fraction of protein in DSC scans and retention of enzyme activity over 5 months. There is also positive correlation between the percentage of CDHP in solution up to 40% w/w and the thermal stability of HEWL. The $\Delta H$ and $\Delta G$ of unfolding all increased as the fraction of CDHP in solution was increased. These results have positive implications for liquid formulation of protein based therapeutics where a small increase in shelf life of hours to days and retention of stability upon dilution in vivo would significantly impact the cost and complications of this category of drugs.

HEWL was chosen as a protein in these experiments because it is a well characterized protein which is widely available. While 80% w/w CDHP was able to dissolve cyt C at 37 mg/ml, HEWL displayed limited solubility in this solution (Fujita, MacFarlane, & Forsyth, 2005) (Fujita, Forsyth, MacFarlane, Reid, & Elliott, 2006). This was shown by a spectrophotometric analysis performed in our lab by Dr. Katherine Weaver, seen in FIGS. 4, 5, and 6. A spectrophotometer, a Thermo Fisher Scientific Nanoprop 1000, was used to detect the presence of aggregates in HEWL formulated at 1, 10, and 25 mg/ml in 80% w/w CDHP. Aggregation is evidence that the protein is not in solution. In the Weaver experiment, a wide range of wavelengths from 220 nm to 750 nm were passed through the optimized column length and an absorbance was recorded for each. An increased absorbance from the baseline measurement was interpreted as hydrolysis or aggregate formation. No absorbance was expected beyond normal peptide bond and aromatic amino acid absorbance ranges (190-230 nm and 280 nm respectively), thus an increase in absorbance at wavelengths above this was taken as an indication of protein aggregation. The results from the Weaver experiment are shown in FIGS. 4, 5, and 6.

Figure 4:
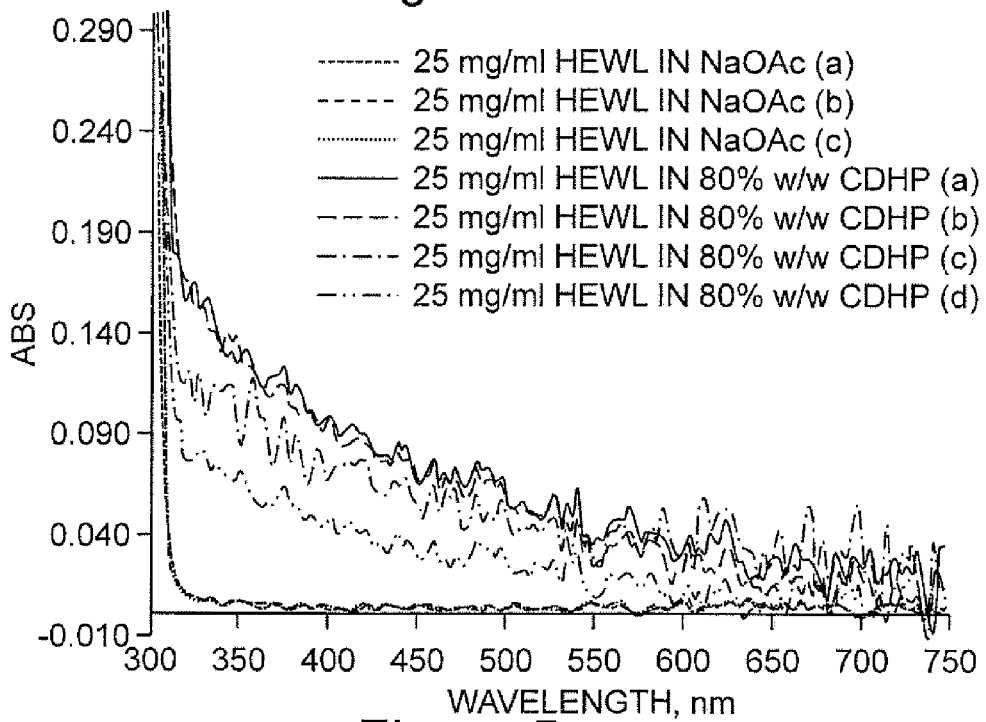
FIG. 4. Absorbance at various wavelengths in 25 mg/ml hen egg white lysozyme (HEWL) formulated in 80% w/w CDHP or 0.1M sodium acetate (NaOAc).

FIG. 4 shows the Nano Drop results for 25 mg/ml HEWL formulations in 80% w/w CDHP or 0.1M NaOAc. Four 25 mg/ml formulations in 80% w/w CDHP are shown in solid medium or light grey lines and triplicate 25 mg/ml formulations in a control buffer are shown in black dashed or dotted lines. There is a definite absorbance increase in the 25 mg/ml samples formulated in 80% w/w CDHP from that of the control samples. This is indicative of a HEWL solubility limit below 25 mg/ml.

Figure 5:
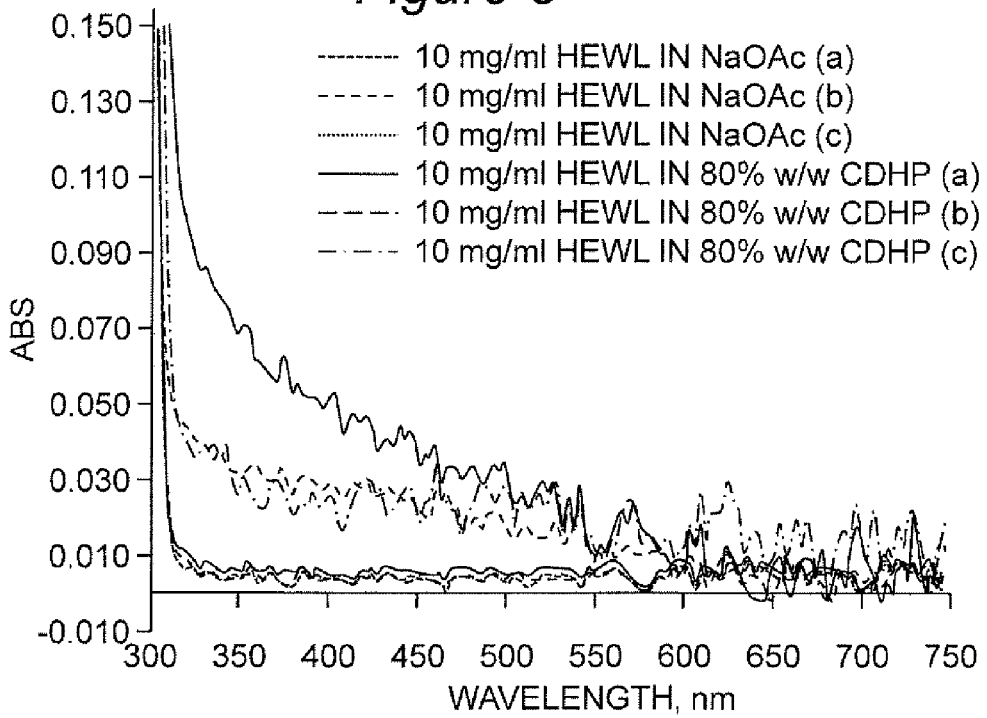
FIG. 5. Absorbance at various wavelengths in 10 mg/ml HEWL formulated in 80% w/w CDHP or 0.1M NaOAc.

FIG. 5 shows the Nano Drop results for 10 mg/ml HEWL formulations prepared in triplicate in 80% w/w CDHP or 0.1M NaOAc. The triplicates prepared in CDHP are shown in solid medium or light grey lines, and the triplicates prepared in a control buffer are shown in black dashed or dotted lines. There is an absorbance increase in the 10 mg/ml samples formulated in 80% w/w CDHP, indicating aggregation. These results suggest the solubility limit of HEWL is below 10 mg/ml.

Figure 6:
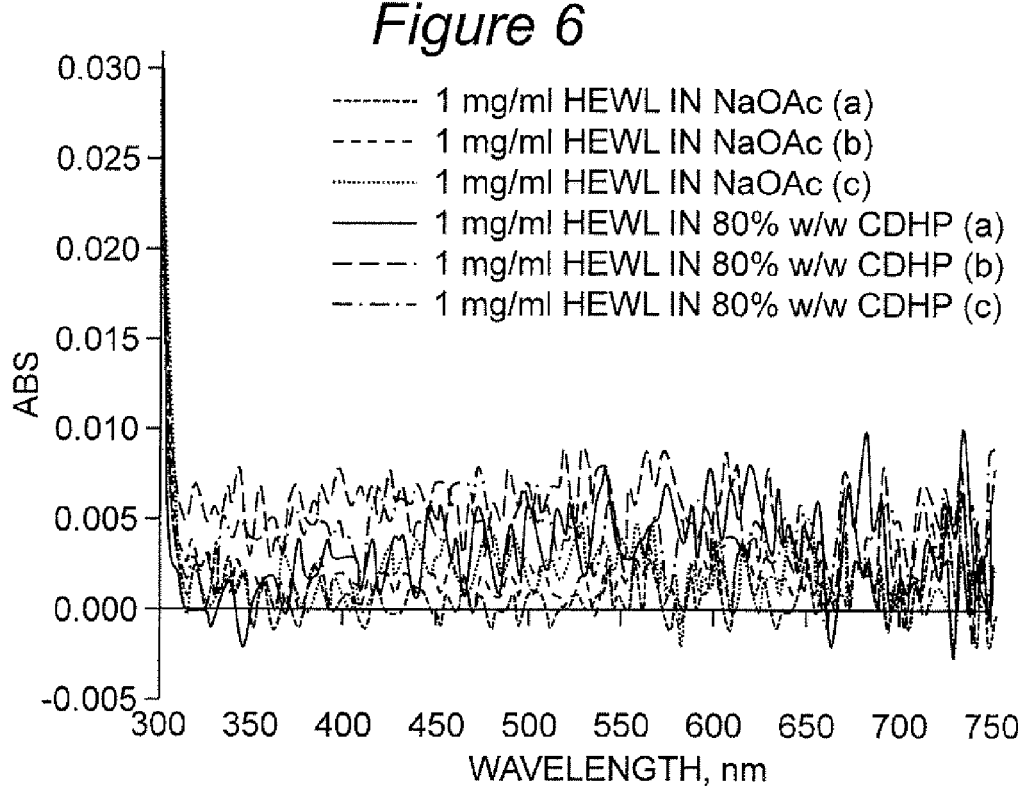
FIG. 6. Absorbance at various wavelengths in 1 mg/ml HEWL formulated in 80% w/w CDHP or 0.1M NaOAc.

FIG. 6 shows the Nano Drop results for 1 mg/ml HEWL formulations prepared in triplicate in 80% w/w CDHP (shown in solid medium or light grey lines) or 0.1M NaOAc (shown in black dashed or dotted lines). There appears to be a slight absorbance increase in the 1 mg/ml samples formulated in 80% w/w CDHP. Although excessive noise makes it difficult to confirm, this is indicative of a solubility limit of HEWL in 80% w/w CDHP less than 1 mg/ml. These results are all consistent with a low HEWL solubility in 80% w/w CDHP.

Because the solubility limit of HEWL in 80% CDHP was so low, two types of formulations were tested in this body of work. The first type was a dispersion of insoluble protein in which HEWL was formulated at 10 and 100 mg/ml in 80% w/w CDHP. The thermal and functional stability of these dispersions was evaluated monthly. The hydration level for the 80% w/w CDHP was chosen to mirror the storage formulations for the 37 mg/ml cyt C (Fujita, MacFarlane, & Forsyth, 2005) (Fujita, Forsyth, MacFarlane, Reid, & Elliott, 2006). A suitable stabilizing buffer had to be chosen to compare to 80% w/w CDHP. In a study comparing three buffers, an acetate buffer, pH 4.0, has shown the highest conformational stability, as evidenced by calorimetric measurements, when tested against glycine buffer, pH 2.5, and phosphate buffered saline (PBS), pH 7.4 (Jiang, 2002) Optimal lysozyme solubility in an acetate buffer, pH 4, has been found to lie between 0.1M to 0.3M buffer (Forsythe & Pusey, 1996). Thus, a 0.1M sodium acetate (NaOAc) buffer at pH 4 was chosen as a baseline comparison.

The nature of the dispersions was evaluated by two methods. Microscopic images were taken to evaluate the presence of HEWL crystals, Secondly, centrifugation of the protein dispersions was performed to achieve partial sedimentation. Complete sedimentation was not feasible because the densities of HEWL and 80% w/w CDHP are so close, but the presence of partial sedimentation confirms the solubility limit has been passed and indicates the presence of a dispersion. Protein concentration in the supernatant and pellet was evaluated to confirm that the dispersed phase was protein. The second formulation type tested was solutions of 1 mg/ml HEWL in aqueous 0.1M NaOAc solvents with 0-40% w/w CDHP acting as a co-solvent. A concentration of 40% w/w CDHP was chosen as a limit, because CDHP increases the viscosity of aqueous solvents and there was concern about damage to the microcalorimeter (to be discussed shortly). A formulation of 20% w/w choline chloride, a more traditional salt, was used as a control. Thermal stability was evaluated upon formulation. Microscopic images were used to confirm the absence of HEWL in the solutions.

Evaluation of Protein Stability

A. Thermal Stability Evaluation of Dispersions and Solutions.

Calorimetric measurement of protein unfolding is a well established means of evaluating protein stability and kinetics. Differential scanning calorimetry, or DSC, is a method of measuring the heat energy released or absorbed from a sample over a range of increasing or decreasing temperatures. If the sample is a protein solution, the protein undergoes a thermal unfolding event, releasing energy as it unfolds. A typical differential scanning calorimeter heats a sample (in this case a dilute protein solution) in a sample cell at a constant rate and at a constant pressure. A reference cell containing only the solvent undergoes the same treatment. Differences in how much heat energy is required to be added to the sample verses the reference cell in order to maintain them at the same temperature is measured. These differences can be related to the constant pressure heat capacity of the protein in solution.

A DSC thermogram plots the excess heat capacity as a function of temperature. The raw endotherm is the heat signature from the protein unfolding event, and in the case of an unfolding protein includes a pre-transitional baseline (before the unfolding event), endothermic unfolding event, and post-transitional baseline (after the protein is thermally denatured). The raw data is be normalized to a buffer baseline as well as the protein concentration in the sample. Several parameters can be obtained from this information. The temperature at the peak of the endothermic unfolding event is the thermal transition midpoint temperature. A higher thermal transition midpoint temperature is indicative of higher thermal stability. The change in enthalpy is calculated from the area under the peak. A larger enthalpy change indicates a protein with more intact chemical bonds being broken. From these parameters, the entropic change during unfolding and the Gibbs free energy can be calculated.

Microcalorimetry is a special kind of DSC, and refers to the ability to measure very small heat flows such as those that occur in very dilute protein suspensions (<1 mg/ml). Using this technique we were able to evaluate the protein dispersions after they were diluted to the working range of the microcalorimeter, which will be addressed shortly. This protocol mimics the conditions a therapeutic protein stored in a dispersion would encounter when diluted in vivo thus providing information on the condition of the protein following storage and dilution back to physiologic osmolality levels. Microcalorimetry was also used to directly evaluate the thermal stability of dilute HEWL aqueous solutions formulations with increasing amounts of CDHP, and therefore provide specific thermodynamic information on the nature of the stabilization effects. Because the solutions required no dilution, thermal stability due to the presence of CDHP could be directly evaluated.

B. Functional Stability Evaluation of Dispersions.

Structural stability does not by itself guarantee that a protein will still function as it should. Therefore, an assessment of enzyme activity of HEWL must be used to fully characterize stability. Recall that HEWL preferentially hydrolyzes β-1,4 glucosidic linkages between NAM and NAG of bacterial cell walls. *Micrococcus lysodeikticus* has these types of bonds in its cell walls, the breaking down of which is manifested as a decreased turbidity in such a bacterial solution. The rate at which this occurs can be monitored as a change in absorbance, and can easily be correlated to enzyme activity. This makes it an ideal assay for quantifying HEWL activity.

Evaluation of Sterility in Dispersions.

Because the dispersion formulations are tested over a long period of time, the risk for bacterial and fungal growth must be minimized as an extraneous variable. The storage containers must be sterilized by exposure to UV light for at least 24 hours, and the CDHP and buffer must be autoclaved for 45 minutes at least 248 F. Furthermore, there must be a way of evaluating the presence of foreign contaminant growth. An enriched test broth specific for bacteria and fungi as described by Parrow and coworkers can be used to eliminate the possibility that the protein is being denatured by bacterial or fungal growth (Parrow, Burkholder, Deamer, & Ramsdell, 2005).

Confirming Sample Protein Concentration.

There was some concern regarding the homogeneity of the dispersion formulations due to insolubility and the ability to accurately pipette such viscous solutions. Uncertainty in the ability to precisely weigh out very small amounts of protein raised concerns in both the dispersions and solutions. Therefore, the concentration in all evaluated samples had to be verified. The bicinchoninic acid protein assay is a spectrophotometric method for determining protein concentration and will be used here.

Experimental Design and Statistical Analysis.

The long term stability evaluation of 10 and 100 mg/ml HEWL dispersion in 80% w/w CDHP is a between subjects factorial design with two factors, concentration and solvent. The levels of each factor are 10 and 100 mg/ml and CDHP and NaOAc, respectively. This experimental design is easily analyzed with a two way ANOVA using the rate of decrease of the calorimetric or activity data over time as the dependent variable. The evaluation of HEWL as a function of CDHP concentration can be evaluated using one way ANOVA (t-test). Here there is one factor, the solvent, with 7 levels (0% w/w CDHP, 5% w/w CDHP, 10% w/w CDHP, 20% w/w CDHP, 30% w/w CDHP, 40% w/w CDHP, 20% w/w choline chloride. Statistical analysis was performed with SPSS statistical software. Statistical significance was assessed on the $\alpha=0.05$ level.

Material.

HEWL and *micrococcus lysodeikticus* bacteria were purchased from Worthington Biochem (Lakewood, N.J.). CDHP was prepared by the Monash group by standard methods (Fraser, Izgorodina, Forsyth, Scott, & MacFarlane, 2007) (Fujita, Forsyth, MacFarlane, Reid, & Elliott, 2006). All other chemicals were purchased from Sigma Aldrich. The 2 ml silanized glass vials with cap and septa were purchased from National Scientific Company (Rockwood, Tenn.).

Methods.

Because HEWL solubility was found to be low in 80% w/w CDHP, two types of were tested. The first was a dispersion of HEWL in 80% w/w CDHP. The second was solutions of HEWL in aqueous buffer with increasing amounts of CDHP.

A. HEWL Dispersion Formulation.

To evaluate the long term stability of dispersions of HEWL in a mildly hydrated CDHP solution, HEWL was formulated in triplicates in 80% w/w CDHP (aq) 10 and 100 mg/ml, by adding the hydrated CDHP directly to lyophilized protein. The samples were formulated in 2 ml silanized glass vials to reduce protein-surface interactions, covered with cap and septa, wrapped with parafilm to ensure no drying out of the sample, and stored away from sunlight. They were stirred for at least 24 hours until a homogeneous distribution of protein was obtained. To assure no bacteria growth in the samples, both buffer and CDHP were autoclaved for 45 minutes at 248° F. before formulation. The 35 silanized vials were exposed to UV light for 24 hours to ensure sterility. Control samples at equivalent concentrations were also prepared in triplicates in 0.1M NaOAc buffer (pH 4). Samples were tested for thermal stability via microcalorimetry and functional activity via the *micrococcus lysodeikticus* assay at monthly intervals.

B. HEWL Solution Formulation.

HEWL was dissolved at 1 mg/ml in 0, 5, 10, 20, 30, and 40% w/w CDHP in 0.1M NaOAc. Using a CDHP molecular weight of 201 g/mol, this is 0, 248.76, 497.52, 995.02, 1492.54, and 1990.05 mM CDHP. A 1 mg/ml HEWL control solution was formulated similarly in 20% choline chloride. All samples were prepared in triplicate.

C. Confirmation of the Nature of Dispersion and Solution Formulations.

Solubility of HEWL in both formulation types was evaluated to confirm the presence of a dispersion or a solution. The nature of the HEWL dispersions in 80% w/w CDHP was evaluated by microscopy and sedimentation analysis. The nature of the HEWL solutions was evaluated by microscopy. HEWL formulated at 1, 10, and 100 mg/ml in 80% w/w CDHP and 0.1M NaOAc were observed using Bright field microscopy, and the appearance of any crystals observed and noted. The presence of any CDHP crystals was also noted. Lyophilized HEWL and non-hydrated CDHP crystals were also observed under similar conditions to help with morphological identification. Images were taken using SlideBook. Sedimentation analysis was also used to evaluate the protein dispersions. HEWL was formulated at 10 and 100 mg/ml in 80% w/w CDHP in triplicate. Samples were centrifuged at 15000 RPM for at least 75 minutes. BCA was performed on the formulations before centrifugation to establish the exact concentration in each triplicate. After centrifugation, the supernatant was removed and its protein concentration assessed with a BCA assay. The pellet was re-suspended in an equal amount of 0.1M NaOAc buffer, protein concentration assessed, and a mass balance was performed to confirm the results. Because of similarly matched protein and CDHP densities, complete sedimentation of HEWL particles was not the goal here. However, results did provide confirming evidence that a dispersion was present.

D. Evaluation of Thermal Stability Using Microcalorimetry.

A MicroCal VP-DSC microcalorimeter was used to assess thermal structural stability of all samples. Baseline repeatability was established with a minimum of 5 buffer-buffer scans. HEWL dispersions were diluted with 0.1 M NaOAc buffer (pH 4) so that the concentration fell close to 0.2 mg/ml, degassed for 6 minutes with a ThermoVac, loaded into the cells, and scanned from 10° C. to 90° C./hour with a 15 minute pre-scan wait to allow for equilibration of the DSC. HEWL solutions were tested similarly with no dilution of the samples. Between samples, during the filling period of 15° C. to 25° C., the sample cell of the DSC was flushed with at least 25 ml distilled $H_2O$, then at least 15 ml NaOAc to ensure no sample residue remained behind. Thermal profiles, enthalpy changes, and transition temperatures were obtained with Origin software.

E. *Micrococcus Lysodeikticus* Turbidimetric Assay.

Functional integrity of lysozyme was determined according to Shugar, which is based on the decrease in turbidity of the substrate, *micrococcus lysodeikticus*, suspension (Sugar, 1952). The *micrococcus lysodeikticus* turbidimetric assay takes advantage of the ability of HEWL to preferentially hydrolyze $\beta$-1,4 glucosidic linkages between NAM and NAG of bacterial cell walls, A 0.3 mg/ml suspension of the bacteria in 0.1M phosphate buffer (pH 7) was prepared. Serial dilutions of stored proteins were prepared so that the absorbance decay fell between −0.015 and −0.04 $\Delta A450$/min. At time zero, 10 µL of the bacteria suspension were added to 290 µL of sample in a 96 well plate. Kinetic absorbance measurements were taken every 6-10 seconds for 2 minutes at 450 nm, and a slope was determined. Only those slopes with a linear regression coefficient of at least 0.98 were accepted. The $\Delta A450$/min was used to determine enzyme units (EU) of activity per mg protein.

F. Test for Sterility Using Culture Broth Specific for Fungi and Bacteria.

Each storage sample formulation was tested at 4 months for bacteria and fungi contaminants as described by Parrow et al. An aliquot of each sample formulation was inoculated with an enriched test broth (0.5 g/L bactopeptone, 0.5 g/L yeast extract, 0.5 g/L glucose) in 20 ml broth tubes. Positive and negative controls were also prepared. Samples were observed after 7-10 days incubated in darkness at room temperature for obvious signs of contamination, manifested as extreme broth cloudiness. (Parrow, Burkholder, Deamer, & Ramsdell, 2005)

G. Protein Concentration Determination with Bicinchoninic Acid Assay.

Protein concentration for each tested aliquot was validated with a bicinchoninic acid (BCA) protein assay kit was purchased from Sigma Aldrich. A standard curve generated by preparing a serial protein dilution series from freshly reconstituted 2 mg/ml HEWL standards formulated in triplicate in 0.1M NaOAc buffer (pH4). Because different proteins may exhibit slightly different behavior in the BCA assay, the bovine serum albumin (BSA) protein concentration standard was not used to calculate the serial dilution series as prescribed by Peirce.

20 µl aliquot samples of each concentration were added to 280 µl of the working reagent in a 96 well plate, incubated at 60° C. for 30 minutes, and cooled to room temperature. Absorbance measurements were made at 570 nm on a microplate reader. The working range of this assay is 5-2000 µg/ml.

Data and Analysis

Solubility of HEWL in CDHP.

Based on the solubility data acquired previously in our lab, two types of formulations were prepared: a) Protein (HEWL) dispersions prepared in 80% w/w CDHP, with CDHP as the predominant co-solvent and b) solutions of protein (HEWL) in 0.1M sodium acetate, with various amounts of CDHP as a solute. Experiments were performed to verify the nature of these compositions.

A. Dispersions of HEWL in 80% CDHP

Based on data acquired on lysozyme solubility in 80% w/w CDHP, it was observed that the solubility limit of HEWL was less than 1 mg/ml in these formulations. Therefore, higher HEWL concentrations were expected to form a dispersed solid phase in 80% w/w CDHP. To verify that CDHP was not precipitating out of solution and replacing the protein as the dispersed phase, two methods were used to assess the samples. Samples were photographed at high magnification under a microscope, and the morphology of the crystals observed were compared to pure crystals (not shown).

The similarities of HEWL crystals are apparent when observed under bright field microscopy in 1, 10, and 100 mg/ml HEWL in 80% w/w CDHP formulations. No crystals were seen in similar formulations in 0.1M NaOAc, showing that the solubility limit of HEWL is above 100 mg/ml in 0.1M NaOAc.

The second approach to verify these sample compositions was to determine the amount of protein in the dispersed phase after separation of the solid and liquid components by centrifugation. To achieve separation of these components, solutions were centrifuged for 75 minutes at 15000 RPM, about 10% remained in the supernatant. Both the decanted supernatant and the pellet, which was re-suspended in buffer, were analyzed for protein content. It was observed that ~90% of the formulated protein was contained in the pellet. The remaining about 10% of the formulated protein was found in the supernatant. Because the densities of 80% w/w CDHP and HEWL are so similar, the centrifugation time and rate was probably not adequate enough to completely sediment the protein. Although the supernatants appeared clear it is possible that there are sub-visible particles of lysozyme in the supernatant that resist sedimentation at this rate. Although this approach is not useful for establishing solubility limits, it does confirm that the solid phase is predominantly HEWL, as expected.

B. Solutions of HEWL (1 mg/ml) with Increasing Concentrations of CDHP.

All samples of HEWL prepared at 1 mg/ml in 0.1M NaOAc containing 0 to 40% w/w CDHP were clear by eye. Bright field microscopy also revealed no crystal formation in any sample, indicating that HEWL is in solution at this concentration in these formulations.

Stability of HEWL in CDHP. Dispersions of HEWL in 80% CDHP

A. Thermal Stability of HEWL Dispersions in 80% CDHP.

Figure 7:
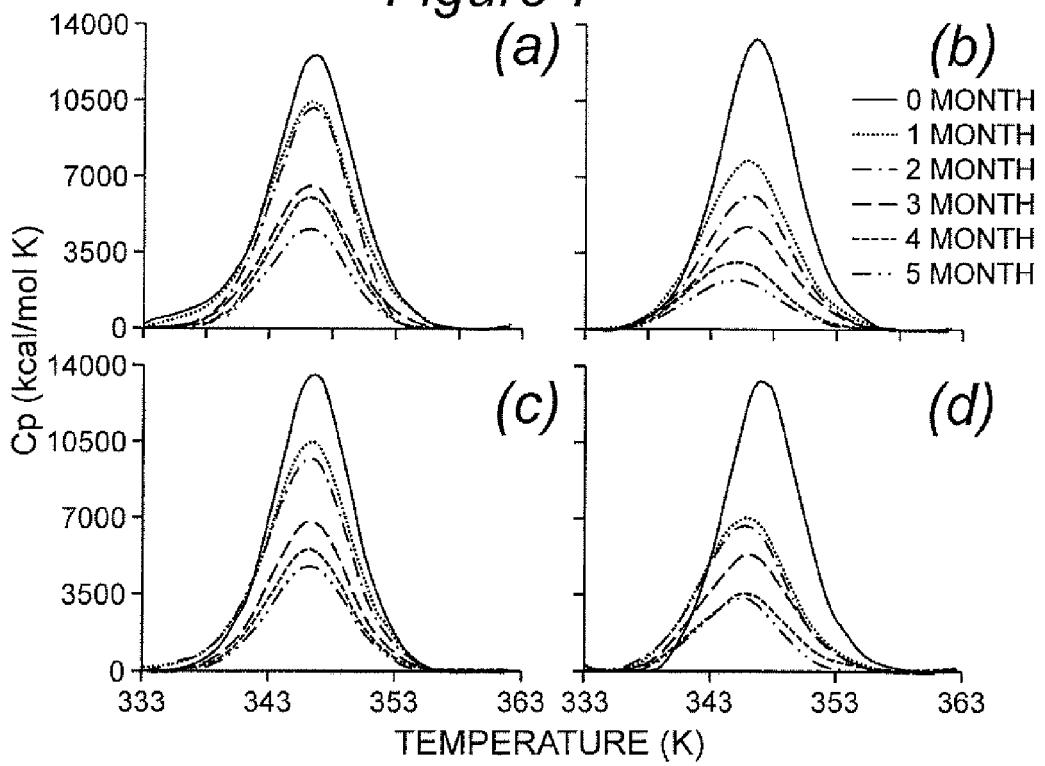
FIG. 7. DSC scans of HEWL formulated at (A) 10 mg/ml and stored in 80% w/w CDHP, (B) 10 mg/ml and stored in 0.1M NaOAc, (C) 100 mg/ml and stored in 80% w/w CDHP, (D) 100 mg/ml and stored in 0.1M NaOAc at 0, 1, 2, 3, 4, and 5 months.

Microcalorimetry was used to evaluate the structural integrity and thermal stability of HEWL after storage as dispersion at 10 and 100 mg/ml in 80% w/w CDHP. All formulations were diluted to 0.1-0.5 mg/ml for testing. This allows one to observe how well protein thermal stability and structural integrity is maintained following storage and then dilution into a solution of similar composition as the environment of the body. FIG. 7 show the averaged DSC traces for the HEWL stored over a period of 5 months at 10 and 100 mg/ml in either 80% w/w CDHP or 0.1M NaOAc. At the time of formulation, there was no apparent immediate denaturation in the CDHP formulations as evidenced by similar peaks between the control and CDHP. All peaks at time zero are sharp and well defined, suggesting a highly cooperative, two state reversible unfolding process. Not surprisingly, there is a significant loss of thermal stability in both control samples over the first month as shown by a decreased area under the peak (i.e. a decrease in enthalpy change of unfolding). The area under the peak of the HEWL formulated in CDHP decreases only slightly over the first month, then begins to mirror that of the control samples in the third and following months. The HEWL formulated in 80% w/w CDHP appears to maintain a superior shelf life over the first two months compared to the buffered counterparts.

TABLE 2

Enthalpy of unfolding of HEWL (cal/mol) stored at 10 and 100 mg/ml in CDHP or 0.1M NaOAc over a period of 5 months.

| | Triplicate | Choline dhp Time (months) | | | | | | NaOAc Time (months) | | | | | |
|---|---|---|---|---|---|---|---|---|---|---|---|---|---|
| mg/ml | Number | 0 | 1 | 2 | 3 | 4 | 5 | 0 | 1 | 2 | 3 | 4 | 5 |
| 10 | 1 | 101700 | 90855 | 79236 | 55227 | 47358 | 36900 | 102530 | 67320 | 52812 | 40734 | 36931.6 | 20900 |
| | 2 | 108300 | 89610 | 79113 | 63418 | 51147 | 43000 | 105480 | 58770 | 56880 | 40690 | 26956.8 | 22400 |
| | 3 | 102000 | 90932 | 80771 | 56640 | 46720.8 | 36900 | 99490 | 71640 | 53856 | 39168 | 24870.6 | 18400 |
| 100 | 1 | 107100 | 89970 | 75132 | 55235 | 45229.5 | 38900 | 101140 | 62010 | 58311 | 46606 | 30888.9 | 26800 |
| | 2 | 100700 | 89606 | 76824 | 57272 | 45580.5 | 36400 | 105200 | 56610 | 60858 | 46506 | 32071.77 | 29100 |
| | 3 | 108300 | 87876 | 77544 | 54900 | 49716 | 39300 | 108200 | 71973 | 54729 | 46224 | 29802.6 | 23900 |

Figure 8:
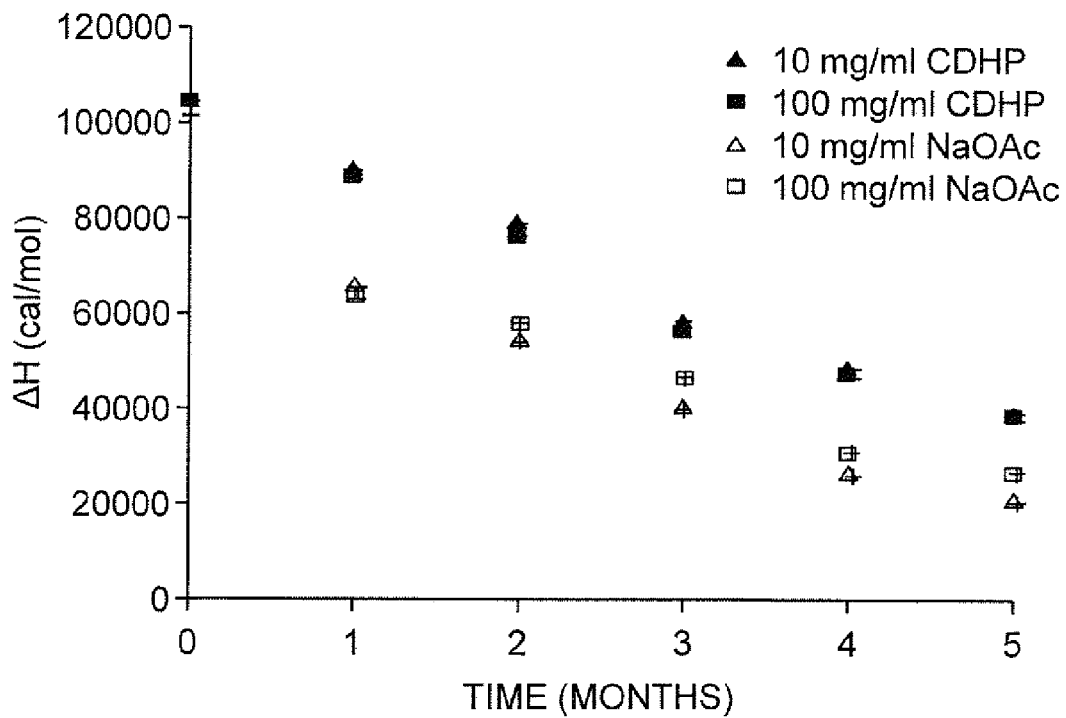
FIG. 8. Enthalpy change of unfolding of HEWL stored at 10 and 100 mg/ml in 80% w/w CDHP or 0.1M NaOAc.

The enthalpy of unfolding is found by integrating the curve generated by plotting the surplus heat capacity at constant pressure of the sample protein solution against the temperature. FIG. 8 shows the trend of this enthalpy change over time and Table 2 shows the enthalpy data for the 10 and 100 mg/ml formulations.

At 1 month, enthalpic change during unfolding decreases on average to 64 and 60% of the maximum, respectively, in the 10 and 100 mg/ml HEWL control formulations, while only decreasing to 87 and 85% if the maximum in the 80% w/w CDHP formulations. This indicates that more of the HEWL is kept structurally intact in the 80% w/w CDHP formulations, leading to a greater release of heat energy when thermally denatured. Using an exponential curve fit in Origin by OriginLab Corporation, an average enthalpic half life of 3.76 months and 3.59 months was calculated for the 10 and 100 mg/ml HEWL in 80% w/w CDHP, as opposed to only 1.99 and 2.1 months for the 10 and 100 mg/ml HEWL in 0.1M NaOAc. A two way ANOVA comparing the decrease in enthalpy over time revealed no significant difference between formulation concentrations for each solvent. However, a significant statistical difference (P=0.002) was found between lysozyme formulated in hydrated CDHP verses NaOAc, with the ionic liquid having a higher stabilizing effect on the protein.

Figure 9:
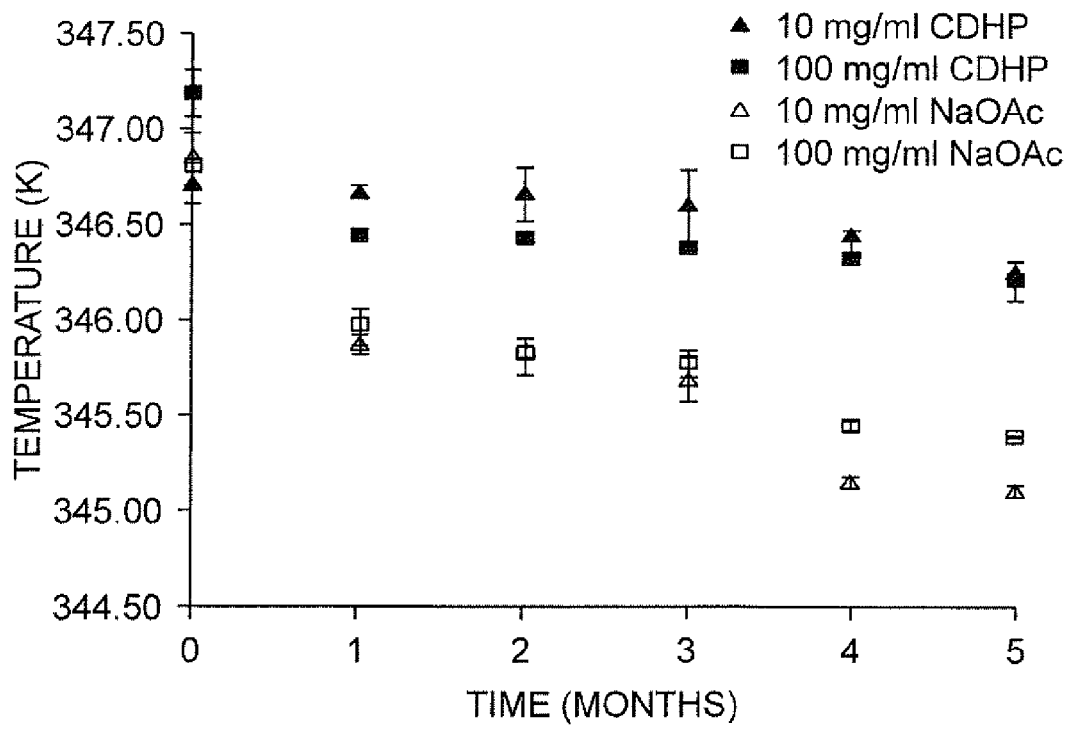
FIG. 9. Thermal transition midpoint temperature of HEWL stored at 10 and 100 mg/ml in 80% w/w CDHP or 0.1M NaOAc.
Figure 11:
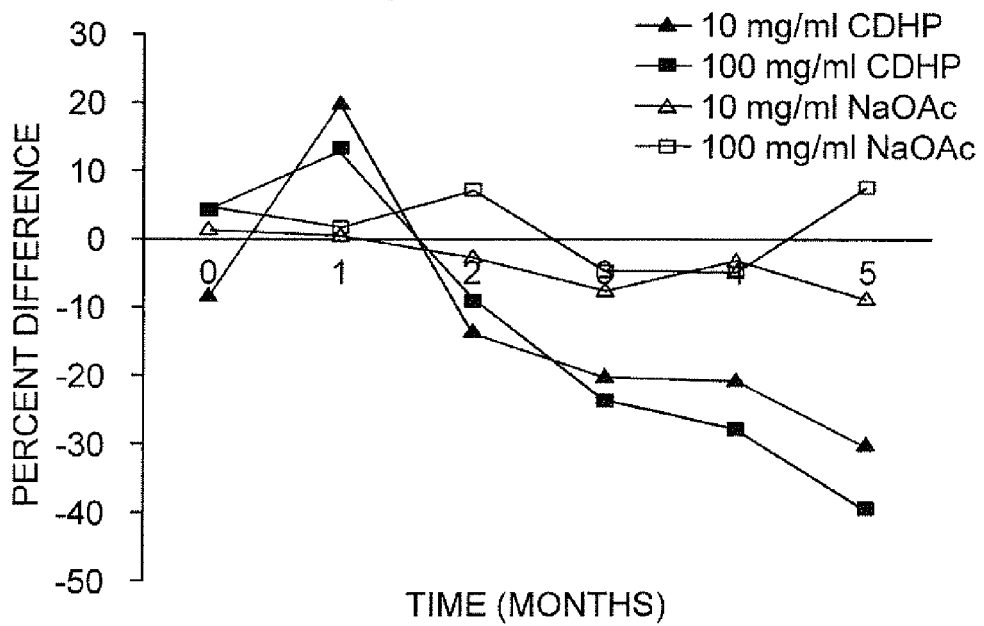
FIG. 11. Average percent difference of measured vs. assumed aliquot protein concentration over time.

FIG. 9 shows the thermal transition midpoint temperature change over time. If the protein is not irreversibly changed as a result of storage and dilution, one would expect to see no change in $T_m$. A decreased $T_m$ would suggest that the protein has decreased in thermal stability as a result of the storage and processing. At the time of formulation, the $T_m$ of all formulations are the same, indicating no irreversible change in both 80% w/w CDHP and 0.1M NaOAc formulations upon formulation and dilution. The thermal transition midpoint temperatures, $T_m$, of all samples progressively decreased over time as seen in FIG. 9, with the largest decrease in the control formulations. The $T_m$ of HEWL formulated in 80% w/w CDHP does not change appreciably, dropping less than a degree, while the $T_m$ of the control formulations drops between one and two degrees over 5 months. A two way ANOVA comparing the 10 and 100 mg/ml transition temperature data revealed a significant difference between solvents (P<0.001, P=0.001, P<0.001 at 1, 3, and 4 months, respectively). The thermal transition data for these dispersed formulations can be found in Table 3.

formulations, but remained fairly constant in the control formulations as seen in FIG. 11. Because HEWL is in a dispersed phase in the 80% w/w CDHP formulations, the sample variability is inevitably higher. Beyond 3 months there appears to be a trend towards less total protein in the extracted samples. While it is possible that this could be due to progressive adherence of the solid phase to the vial, there is some possibility that the protein has chemically degraded to the extent that it is not measurable by standard BCA methods. Because of this net loss of protein at extended storage times, the estimated half-life in CDHP is over-estimated. Further work would be necessary to achieve an appropriate correction. Independent of the reason for the protein loss, the BCA results indicate that storage beyond 2 months in 80 wt % CDHP is not recommended.

D. Sterility Results.

Figure 12:
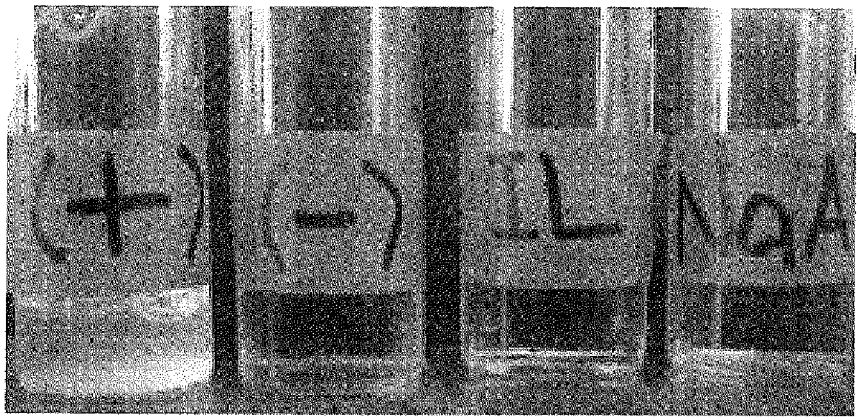
FIG. 12. Contamination vials from left to right: positive control, negative control, sample CDHP formulation, sample NaOAc formulation.

About 100 of each sample formulation was used to inoculate an enriched culture broth and observed after several days. As seen in FIG. 12 no contamination was present in any formulation. The positively marked vial is the positive control, the negatively marked vial is the negative control, the vial marked IL is one of the CDHP formulations, and the vial marked NaA is one of the control formulations. The positive control is clearly cloudy, indicating bacterial or fungal growth. The negative control was identical to all other formulations. Therefore, bacterial or fungal contamination can be ruled out as a variable in the structural and functional stability of the stored formulations.

Solutions of HEWL (1 mg/ml) in 0-40% w/w CDHP Solutions

TABLE 3

Thermal transition midpoint temperature of HEWL stored at 10 and 100 mg/ml in CDHP or 1.0M NaOAc over a period of 5 months.

| | | Choline dhp Time (months) | | | | | | NaOAc Time (months) | | | | | |
|---|---|---|---|---|---|---|---|---|---|---|---|---|---|
| mg/ml | Triplicate Number | 0 | 1 | 2 | 3 | 4 | 5 | 0 | 1 | 2 | 3 | 4 | 5 |
| 10 | 1 | 346.74 | 346.62 | 346.81 | 346.52 | 346.43 | 346.37 | 346.77 | 345.93 | 345.9 | 345.9 | 345.1 | 345.05 |
| | 2 | 346.71 | 346.75 | 346.39 | 346.35 | 346.5 | 346.21 | 347.14 | 345.94 | 345.8 | 345.48 | 345.21 | 345.15 |
| | 3 | 346.71 | 346.7 | 346.84 | 346.98 | 346.47 | 346.27 | 346.68 | 345.79 | 345.85 | 345.72 | 345.17 | 345.13 |
| 100 | 1 | 347.45 | 346.41 | 346.42 | 346.39 | 346.3 | 346.29 | 346.92 | 345.92 | 345.78 | 345.79 | 345.47 | 345.39 |
| | 2 | 347.05 | 346.54 | 346.43 | 346.39 | 346.35 | 346.02 | 346.45 | 346.17 | 346 | 345.9 | 345.41 | 345.39 |
| | 3 | 347.11 | 346.44 | 346.47 | 346.37 | 346.37 | 346.35 | 347.06 | 345.84 | 345.69 | 345.66 | 345.51 | 345.41 |

B. Functional Stability of HEWL Dispersions in 80% CDHP.

Figure 10:
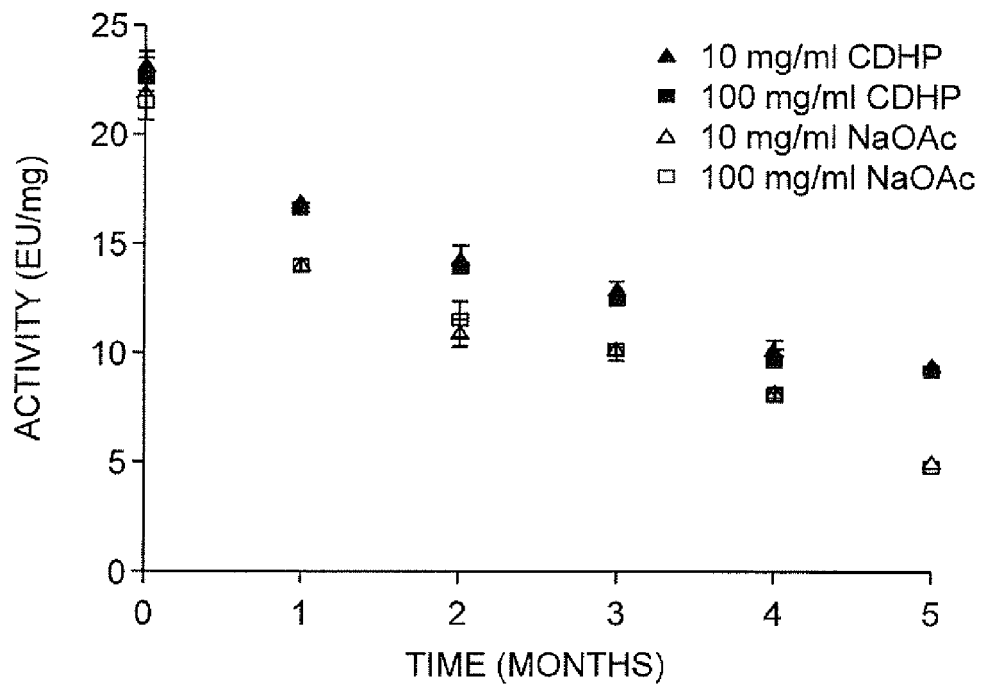
FIG. 10. Enzyme activity of HEWL formulated at 10 and 100 mg/ml in 80% w/w CDHP or 0.1M NaOAc.

Functional integrity of the protein was measured by a turbidimetric assay. As indicated in FIG. 10, lysozyme formulated in NaOAc degrades faster at all concentrations. This assay requires dilution of samples to about 0.03-0.05 mg/ml, which, as for the microcalorimetric experiments, will reveal more about if 80% w/w CDHP stabilizes HEWL during storage and less about if CDHP plays a direct role in enzyme activity changes. A two way ANOVA shows that the decrease in enzyme activity over time difference between solvents is statistically significant (P=0.001). The enzyme activity reflects the functional stability, and appears to mirror the functional stability results from the calorimetric experiments. There is not a statistical difference in enzymatic activity between different protein concentrations in the same solvent.

C. BCA Assay.

The BCA assay was used to ensure that the calorimetric and activity measurements were correctly normalized to the exact protein content within each aliquot. Over time, the expected concentration in the aliquots decreased in the CDHP A. Thermal stability of HEWL Solutions.

Figure 13:
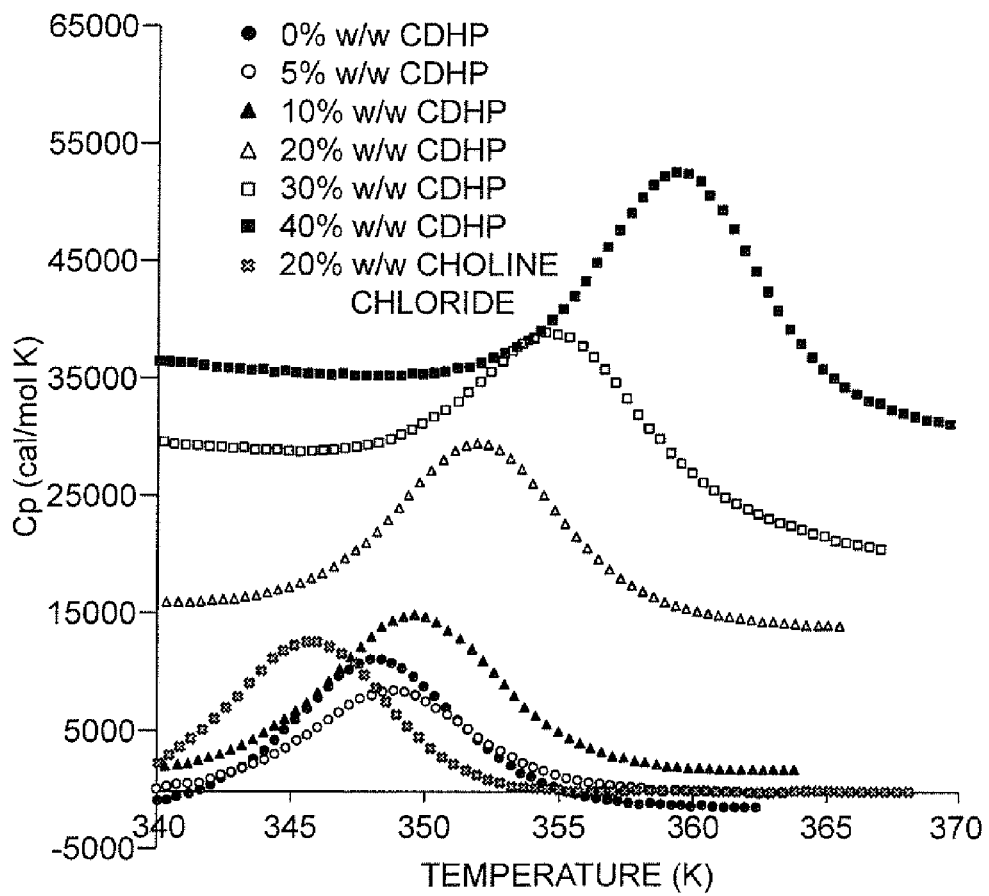
FIG. 13. DSC scans of HEWL formulated at 1 mg/ml in 0, 5, 10, 20, 30, and 40% w/w CDHP in 0.1M NaOAc or 20% w/w choline chloride in 0.1M NaOAc.

FIG. 13 shows the DSC scans of HEWL formulated in increasing concentrations of CDHP with a 20% w/w choline chloride solution used as a control. The thermal transition midpoint temperature clearly increases with an increasing amount of CDHP, but the choline chloride formulation does not have the same stabilizing effect on the HEWL as the corresponding 20% w/w CDHP formulation. These results indicate that the CDHP interacts with the protein or the co-solvent in such a way as to stabilize the protein structure, an effect which is not due to the choline ion alone. Also, the specific heat capacity of the formulations increases with an increasing amount of CDHP. This suggests that the CDHP interacts with the protein or the protein co-solvent relationship in such a way as to highly organize the protein structure so as to better absorb heat energy. This would furthermore yield a higher enthalpy of unfolding in solutions with a higher concentration of CDHP, which is seen.

Figure 14:
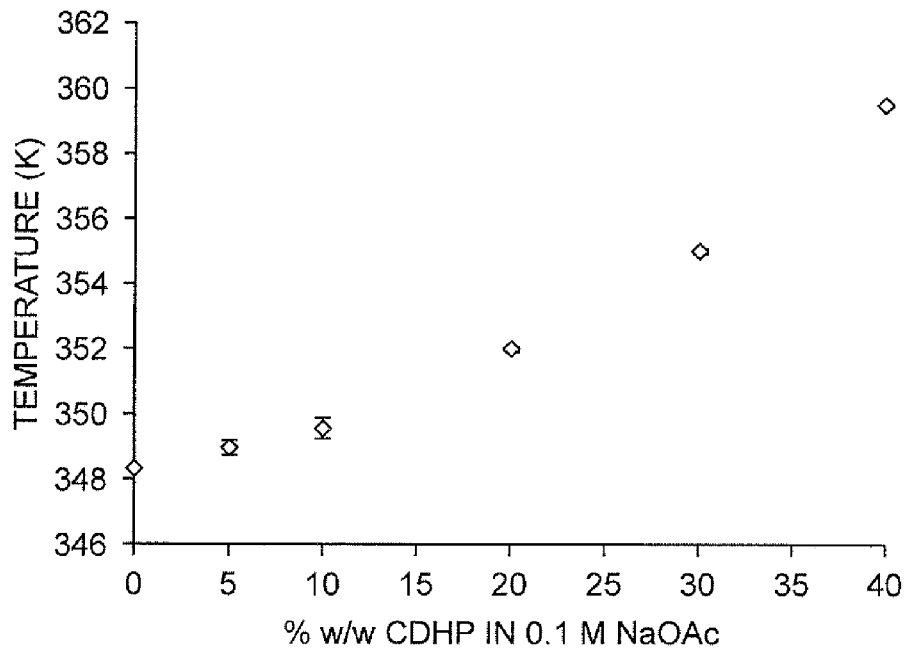
FIG. 14. Thermal transition midpoint temperature of HEWL formulated at 1 mg/ml in 0, 5, 10, 20, 30, and 40% CDHP in 0.1M NaOAc.

FIG. 14 shows that increasing amounts of CDHP in the formulation results in a higher thermal transition midpoint temperature. Unlike the storage formulations, these samples were formulated at 1 mg/ml, a concentration that requires no further dilution for microcalorimetry. Therefore, one may conclude CDHP appears to enable HEWL to resist to thermal denaturation. This data was fit in Origin 8.4 with the following exponential growth fit: $y=344.95+3.33e^{27.12x}$, where y is the thermal transition midpoint temperature in Kelvin and x is the weight percent of CDHP.

Figure 15:
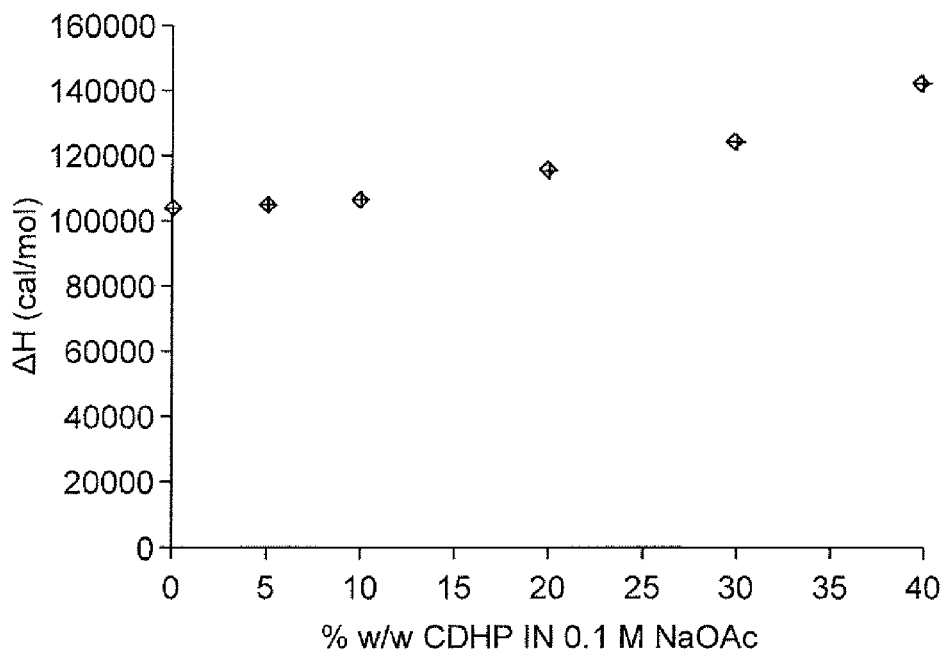
FIG. 15. Enthalpy change of unfolding of HEWL formulated at 1 mg/ml in 0, 5, 10, 20, 30, and 40% w/w CDHP in 0.1M NaOAc.

FIG. 15 indicates that there is a small increase in enthalpy of unfolding as the concentration of CDHP is increased in the solution. More energy is being released as the protein unfolds, which indicates an increase in the ability of the protein to store heat energy. This may suggest direct interaction with the CDHP. Ligand binding could aid in structural stabilization by creating more bonds within the protein. It could also organize water molecules in such a way as to create a more stable hydrogen bond network with the protein. According to Robinson, et al, more polar groups on a protein surface forming hydrogen bonds with water molecules gives rise to higher enthalpic change (Robinson & Cho, 1999). This correlates with the theory that CDHP acts as a kosmotrope to favorably affect protein hydration. Enthalpic data was fit with an adjusted correlation coefficient of 0.9906 with the following exponential growth fit: $y=96031.95+7507.06e^{21.82x}$, where y is the enthalpy change of unfolding in cal/mol and x is the weight percent of CDHP.

Figure 16:
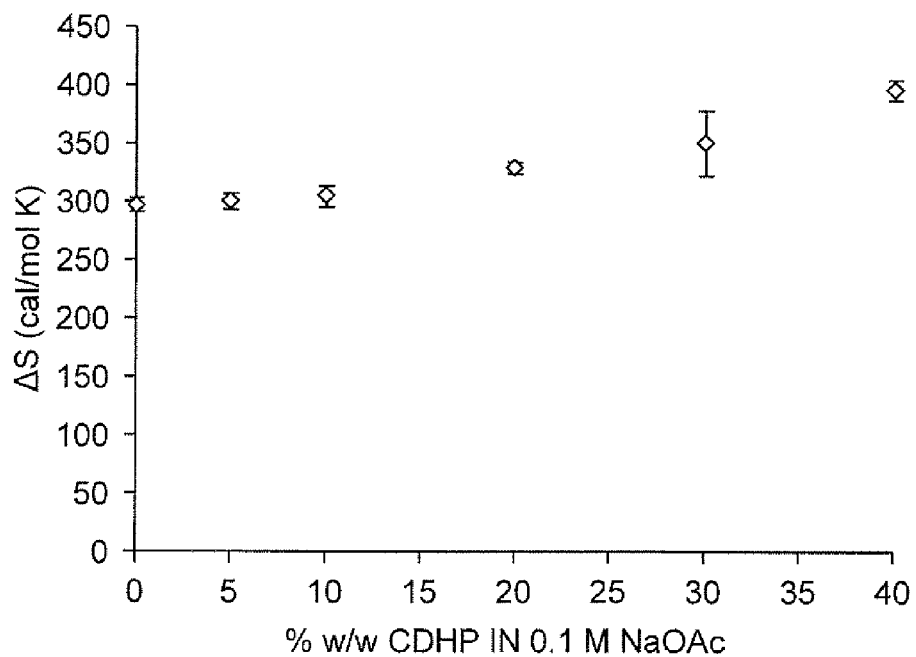
FIG. 16. Entropy change of unfolding of HEWL formulated at 1 mg/ml in 0, 5, 10, 20, 30, and 40% CDHP in 0.1M NaOAc.
Figure 17:
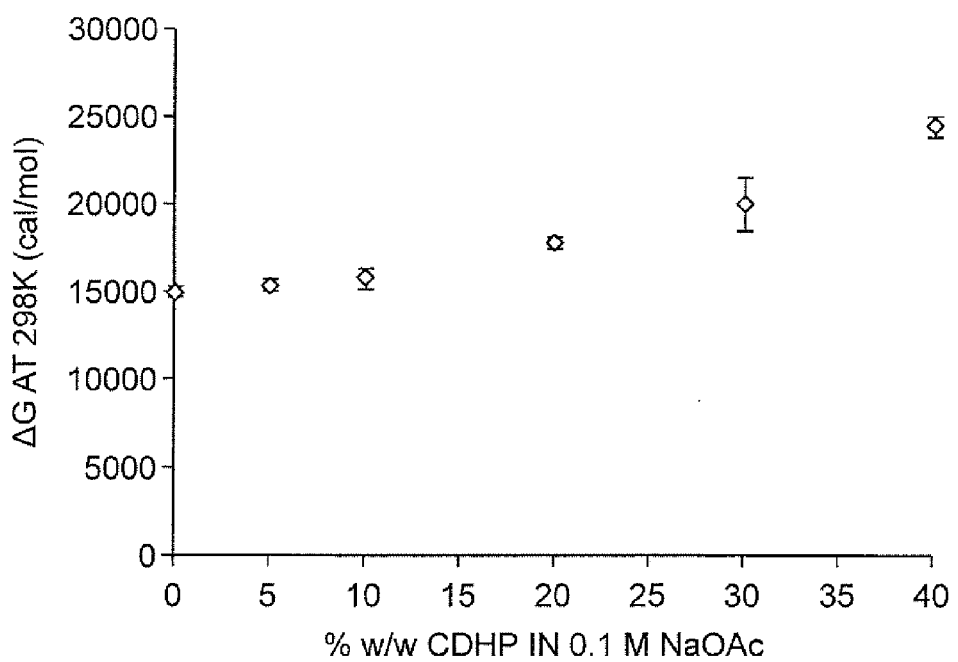
FIG. 17. Gibbs free energy of unfolding at room temperature for HEWL (1 mg/ml) solutions in increasing amounts of CDHP.

FIG. 16 shows an increase in the entropic change as the protein unfolds, following a similar exponential trend as a function of % w/w CDHP in 0.1M NaOAc as the enthalpy change and transition temperature. Average entropic data was fit in Origin 8.4 with the following exponential growth fit: $y=277.43+19.81e^{22.17x}$, where y is the entropy change of unfolding in cal/mol and x is the weight percent of CDHP.

Typically, the unfolded protein has much higher conformational entropy than the folded conformation. In the solutions with a higher concentration of CDHP, this difference is more exaggerated. While this is not a stabilizing entropic effect, the enthalpic change of unfolding is large enough to counteract this, as shown in the increasingly unfavorable Gibbs free energy change of unfolding with higher concentrations of CDHP, as will be shown next.

Figure 18:
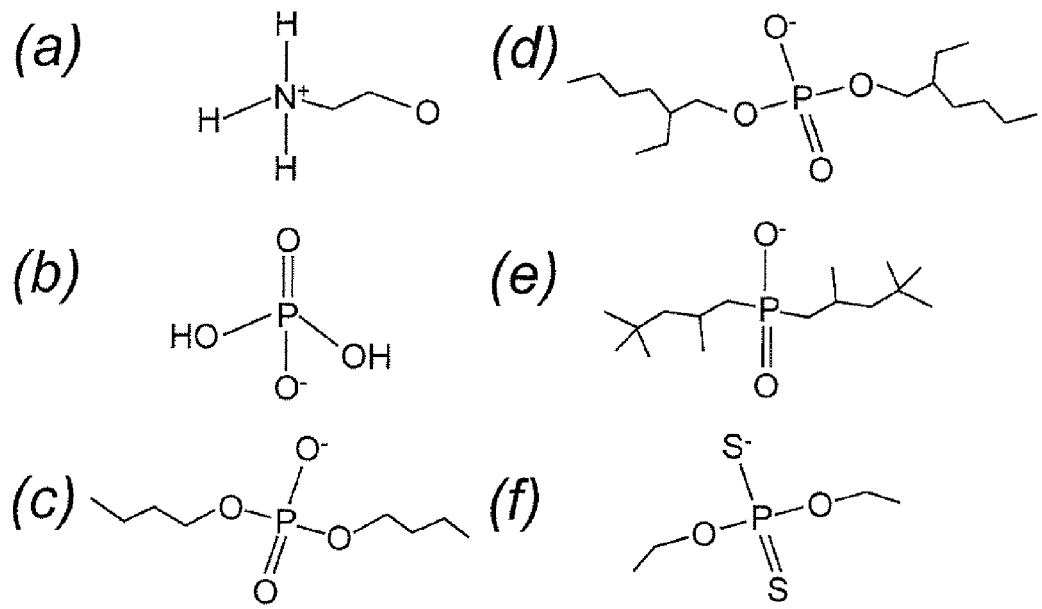
FIG. 18. Structures and names of compounds examined. (a) choline, (b) dihydrogen phosphate, (c) dibutyl phosphate, (d) bis(2-ethylhexyl)phosphate, (e) bis(2,4,4-trimethylpentyl)phosphinate, (f) O,O'-diethyl dithiophosphate.

FIG. 18 shows the Gibbs free energy of unfolding at room temperature of HEWL (1 mg/ml) solutions in 0, 5, 10, 20, 30, and 40% w/w CDHP in 0.1M NaOAc. The free energy change for an unfolding process becomes more unfavorable with higher concentrations of CDHP, thus stabilizing the folded protein. The relationship between Gibbs free energy change of unfolding at room temperature was fit in Origin 8.4 with the following exponential growth fit: $y=13340.678+1618.283e^{20.75x}$, where y is the Gibbs free energy change of unfolding in cal/mol and x is the weight percent of CDHP.

Gibbs free energy of unfolding becomes more positive with increasing concentrations of CDHP, indicating that the folded conformation becomes more energetically favorable at room temperature. All thermodynamic parameters for the HEWL solutions are found in Tables 4 and 5.

TABLE 4

Thermodynamic parameters for 1 mg/ml HEWL formulated in triplicate in increasing % CDHP in 0.1M NaOAc and 20% choline chloride in 0.1M NaOAc.

| Triplicate Number | 0% w/w CDHP | | | 5% w/w CDHP | | | 10% w/w CDHP | | |
|---|---|---|---|---|---|---|---|---|---|
| | Tm (K) | ΔH (cal/mol) | ΔS (cal/mol K) | Tm (K) | ΔH (cal/mol) | ΔS (cal/mol K) | Tm (K) | ΔH (cal/mol) | ΔS (cal/mol K) |
| 1 | 348.328 | 104019 | 298.62 | 349.2292 | 100408 | 287.51 | 349.2334 | 104260 | 298.54 |
| 2 | 348.341 | 107800 | 309.47 | 349.2177 | 108540 | 310.81 | 349.25 | 102581 | 293.72 |
| 3 | 348.397 | 100216 | 287.65 | 348.5 | 106838 | 306.57 | 350.238 | 113549 | 324.21 |

| Triplicate Number | 20% w/w CDHP | | | 30% w/w CDHP | | | 40% w/w CDHP | | | 20% w/w Choline Chloride | | |
|---|---|---|---|---|---|---|---|---|---|---|---|---|
| | Tm (K) | ΔH (cal/mol) | ΔS (cal/mol K) | Tm (K) | ΔH (cal/mol) | ΔS (cal/mol K) | Tm (K) | ΔH (cal/mol) | ΔS (cal/mol K) | Tm (K) | ΔH (cal/mol) | ΔS (cal/mol K) |
| 1 | 351.97 | 115791 | 328.98 | 355.0065 | 139533 | 393.04 | 359.42 | 140490 | 390.9 | 345.617 | 92354 | 267.21 |
| 2 | 352.09 | 119528 | 339.48 | 355.1455 | 128741 | 362.5 | 359.543 | 149751 | 416.5 | 345.77 | 96972 | 280.45 |
| 3 | 351.9444 | 113549 | 322.63 | 354.9535 | 106557 | 300.2 | 359.515 | 139216 | 307.2 | 345.511 | 91615 | 265.16 |

TABLE 5

Gibbs free energy change at 25 C. of triplicates of 1 mg/ml HEWL in increasing amounts of CDHP and 20% w/w choline chloride. Units are in cal/mol.

| | Formulation | | | | | | |
|---|---|---|---|---|---|---|---|
| Triplicate | 0% w/w CDHP | 5% w/w CDHP | 10% w/w CDHP | 20% w/w CDHP | 30% tw/w CDHP | 40% w/w CDHP | 20% w/w Choline Chloride |
| 1 | 15030.24 | 14730.02 | 15295.08 | 17754.96 | 22407.08 | 24001.8 | 12725.42 |
| 2 | 15577.94 | 15918.62 | 15052.44 | 18362.96 | 20716 | 25634 | 13397.9 |
| 3 | 14496.3 | 15480.14 | 16934.42 | 17405.26 | 17097.4 | 23830.4 | 12597.32 |

B. BCA Concentration Verification Assay.

Verification of sample concentration using the BCA was on all solutions of HEWL (1 mg/ml) in 0-40% w/w CDHP. Sample variability was minimal.

Discussion

Two types of formulations were investigated in this work: high concentration protein dispersions and low concentration protein solutions. In the case of the dispersion formulations, HEWL was prepared at 10 and 100 mg/ml in 80% w/w CDHP. This particular concentration of CDHP was shown to be optimal for achieving a multi-year shelf life of cyt C at protein concentrations up to 37 mg/ml (Fujita, Forsyth, MacFarlane, Reid, & Elliott, 2006). Because HEWL was relatively insoluble in 80% w/w CDHP, dispersed protein solutions were prepared instead of protein solutions. Dispersions are readily soluble compared to bulk lyophilized formulations (Krasnyuk Jr., 2009). This can positively impact the time required to prepare solutions at point-of-use, which is very important for emergency therapeutics such as Factor VIII used for hemorrhaging (Chuansumrit, et al., 2000). In the case of the low concentration solutions, HEWL was dissolved at 1 mg/ml in increasing ratios of 0.1M NaOAc to CDHP. In the range of 0-40% w/w CDHP, HEWL was fully soluble at this concentration.

A. Protein Dispersions.

HEWL dispersions stored in 80% w/w CDHP remained more stable over time as indicated by a higher thermal transition midpoint temperature, enthalpy change of unfolding, and enzyme activity compared to control at all points over time. One can equate this to an increased shelf life of HEWL in comparison to the control. Without being bound to a particular theory, the 80% w/w formulations are most likely stabilized due to insolubility at this hydration level or due to the extremely viscous nature of the formulation.

The dispersed nature of these formulations was supported by the presence of HEWL crystals in the 80% CDHP formulations at 20× and a high protein content in the sedimented phase. These results are consistent with the work performed in our biostability lab by Dr. Katherine Weaver using the NanoDrop 1000 to probe solubility of 1, 10, and 25 mg/ml HEWL formulations in 80% w/w CDHP and 0.1M NaOAc. The buffered solutions appeared to be in solution, while the 10 and 25 mg/ml formulations in 80% w/w CDHP displayed aggregation. (The solubility of the HEWL at 1 mg/ml in 80% CDHP were inconclusive due to excessive noise in baseline readings, but the results suggest that the solubility limit may be less than 1 mg/ml).

Insoluble protein may be stabilized because it is trapped in a semi-lyophillized form. In other words, rather than a solution, CDHP arranges crystallized lysozyme in a heterogeneous dispersion or suspension. The removal of water from the lyophilized protein limits its flexibility, thus dramatically decreasing the entropy of the system and effectively stabilizing the protein. Therefore, lysozyme may be indirectly stabilized by CDHP purely because solvent accessibility is decreased at these concentrations.

There may also be a solvent viscosity effect on protein conformational stability in these solutions. Ansari, et al characterized myoglobin conformational change as a function of solvent viscosity. They defined an exponential decay function relating the rate constant of conformational change with solvent viscosity. Between 0.1 and 1 cP, only internal protein-protein friction predominated the rate constant value. Between 1 (the viscosity of water at room temperature) and 10 (the viscosity of kerosene at room temperature), internal protein-protein and friction exerted by the solvent on the protein surface caused a large decrease in the rate constant to 80% (at 1 cP) and 12% (at 10 cP) of the original. At higher solvent viscosities from 10 to 1000 cP (the viscosity of castor oil at room temperature) where friction between the solvent and protein surface predominated, the rate constant decreased exponentially to nearly 1% (at 1000 cP) of the original rate constant (Ansari, Jones, Henry, Hofrichter, & Eaton, 1992). 80% w/w/CDHP has a room temperature viscosity of 440 cP (similar to motor oil) (Fujita, Nakamura, Igarashi, Samejima, & Ohno, 2009) and is therefore well in the range of solvent viscosity dominating effects on protein kinetics. The viscosity of the protein formulations is undoubtedly higher than 80% w/w/CDHP alone. It stands to reason, without being bound to a particular theory, that viscosity as well as HEWL insolubility contributes to the enhanced shelf life seen in the stored dispersed formulations. This is likely true in the case of the previously reported stabilization effects of cyt C as evidenced by a shift in the thermal transition midpoint temperature from 80 C.° to 120 C.° (Fujita, Forsyth, MacFarlane, Reid, & Elliott, 2006) (Fujita K., et al., 2007).

B. HEWL Solutions.

The solutions of 1 mg/ml HEWL in 0, 5, 10, 20, 30, and 40% w/w CDHP revealed an increase in thermal stability as evidenced by an increase in the $T_m$. Viscosity may play a role here as well, Ansari, et al has shown an exponential decrease in protein conformational dynamics as solvent viscosity increases from only 1 to 10 cP (Ansari, Jones, Henry, Hofrichter, & Eaton, 1992). The thermal transition midpoint temperature of HEWL in this study has also been shown to follow an exponential trend with the increase in CDHP. This exponential relationship suggests the thermal stability imparted by the CDHP may be due to the increased solvent viscosity.

The thermal stability of 1 mg/ml HEWL formulated in increasing concentrations of CDHP may also be due in part to direct protein-CDHP interaction, but it seems more likely to be due to an ability of CDHP to organize the hydration water in a favorable manner for the folded protein. Robinson, et al summarizes the effect of water molecules of the hydration shell around proteins and unfolding and the thermodynamic contribution, and the increased enthalpic change of unfolding with increasing amounts of CDHP may be due to an ability of CDHP to favorably impact protein hydration, as indicated previously.

Conclusions.

The stability of a model protein, lysozyme, in hydrated CDHP has been quantified. The thermal stability of HEWL formulated at 10 and 100 mg/ml in 80% w/w CDHP was evaluated by microcalorimetric methods. These formulations were shown to have a longer shelf life than control samples in buffer. The structural and functional half integrity of the protein in 80% w/w was significantly superior to the control formulations over the first two months of storage as evidenced by a higher thermal transition midpoint temperature, enthalpy change of unfolding, and enzyme units per mg. Activity measurements were consistent with the thermal analysis. Because these concentrated protein formulations had to be diluted with a control buffer by factors on the order of at least 100 and 1000, respectively, for testing, these results mirror what would happen to the protein upon dilution and in vitro administration. It is possible that the increased shelf life of HEWL dispersions in 80% w/w CDHP may not be due to specific interaction with the protein, but rather maintenance of the protein in the very stable suspended crystalline form. Because there appears to be a net loss of protein when sampling from the same vial after 2 months of storage, possibly due to adhesion to the vial and/or chemical degradation, storage beyond 2 months would not be recommended in 80 wt % CDHP solution.

Although results with cyt C have suggested that high concentrations of CDHP are needed to achieve increased protein stability, the present invention and data presented herein with HEWL formulated in aqueous solutions of CDHP up to 40% w/w show that thermal stability can be enhanced at low CDHP concentrations which is an unexpected result. When solutions of HEWL were formulated at 1 mg/ml in increasing concentrations of CDHP and analyzed (without no dilution), an exponential relationship between the thermal transition midpoint temperature and CDHP concentration was seen. Also, the enthalpy change of unfolding and the entropy change of unfolding increased. The result was an increase in the thermal stability of the protein and a preference for the folded state as the concentration of CDHP is increased, possibly due to kosmotropic effects. The stabilizing effect was prominent as low as 20% w/w CDHP (1.243 M). Although the osmolality of such a formulation is somewhat high for direct injection, this formulation could be useful in an osmotic pump or other delivery device vehicle such as nanoparticles. Many therapeutic proteins maintain suitable functional and structural integrity for only a few hours in liquid formulation. Even a small increase in protein stability could have a large economic impact as well as substantially better patient outcomes.

REFERENCES

1. Abbott, A., & Davies, D. (2005). Salty Solvents—Ionic Really. Royal Society of Chemistry.
2. Ansari, A., Jones, C. M., Henry, E. R., Hofrichter, J., & Eaton, W. A. (1992). The role of solvent viscosity in the dynamics of protein conformational changes. Science, 256 (5065), 1796-1798.
3. Baker, S. N., & McCleskey, M. T. (2004). Fluorescence studies of protein thermostability in ionic liquids. ChemComm, 8, 940-941.
4. Branchu, S. (1999). A central composite design to investigate the thermal stabilization of lysozyme. Pharmaceutical Research, 702-708.
5. Byrne, N., Wang, L.-M., Belieres, J.-P., & Angell, C. A. (2007). Reversible foldingunfolding, aggregation protection, and multi-year stabilization, in high concentration solutions, using ionic liquids. ChemComm, 2714-2716.
6. Chaplin, M. (2008, Sep. 26). Protein Hydration. Retrieved Oct. 2, 2008, from Water structure and science: http://www.lsbu.ac.uk/water/sitemap.html
7. Chuansumrit, A., Isarangkura, P., Angchaisuksiri, P., Sriudomporn, N., Tanpowpong, K., Hathirat, P., et al. (2000). Controlling acute bleeding episodes with recombinant factor VIIa in haemophiliacs with inhibitor: continuous infusion and bolus injection. Haemophilia, 6 (2), 61-65.
8. Cooper, A. (2000). Heat Capacity of hydrogen-bonded networks: an alternative view of protein folding thermodynamics. Biophysical Chemistry, 85, 25-39.
9. Cooper, A., Nutley, M. A., & Wadood, A. (2001). Protein-ligand interactions: hydrodynamics and calorimetry (Vol. 1). New York, N.Y.: Oxford University Press.
10. Forsythe, E. L., & Pusey, M. L. (1996). The effects of acetate buffer concentration on lysozyme solubility. Journal of Crystal Growth, 6, 112-117.
11. Fraser, K. J., Izgorodina, E. I., Forsyth, M., Scott, J. L., & MacFarlane, D. R. (2007). Applications of ionic liquids in the chemical industry. Chem Commun, 3817-3819.
12. Fujita, F., MacFarlane, D. R., & Forsyth, M. (2005). Protein solubilising and stabilizing ionic liquids. Chemical Communications, 4804-4806.
13. Fujita, K., Forsyth, M., MacFarlane, D. R., Reid, R. W., & Elliott, a D. (2006). Unexpected improvement in stability and utility of cytochrome c by solution in biocompatible ionic Liquids. Biotechnology and Bioengineering, 1209-1213.
14. Fujita, K., MacFarlane, D. R., Forsyth, M., Yoshizawa-Fujita, M., Murata, K., Nakamura, N., et al. (2007). Solubility and stability of cytochrome c in hydrated ionic liquids: effect of oxo acid residues and kosmotropicity. Biomacromolecules, 8, 2080-2086.
15. Fujita, K., Nakamura, N., Igarashi, K., Samejima, M., & Ohno, H. (2009). Biocatalytic oxidation of cellobiose in an hydrated ionic liquid. Green Chemistry, 11 (3), 351-354.
16. Hedoux, A., Willart, J. F., Ionov, R., Affouard, F., Guinet, Y., Paccou, L., et al. (2006). Analysis of Sugar Bioprotective Mechanisms on the Thermal Denaturation of Lysozyme from Raman Scattering and Differential Scanning calorimetry Investigations. Journal of Physical Chemistry, 110 (45), 22886-22893.
17. Hirano, A., Hamada, H., Okubo, T., Noguchi, T., Higashibata, H., & Shiraki, K. (2007, September). Correlation between thermal aggregation and stability of lysozyme with salts described by molar surface tension increment: an exceptional propensity of ammonium salts as aggregation suppressor. The Protein Journal, 423-433.
18. Jiang, G. W. (2002). Assessment of protein release kinetics, stability and protein polymer interaction of lysozyme encapsulated poly(d,l-lactide-co-glycolide) microspheres. Journal of Controlled Release, 137-145.
19. Kolarama Information. (2006). The protein therapeutics market: the science and business of a growing sector. New York City, N.Y.: Kolarama Information.
20. Kragl, U., Eckstein, M., & Kaftzik, N. (2002). Enzyme catalysis in ionic liquids. Current Opinion in Biotechnology, 13 (6), 565-571.
21. Krasnyuk Jr., I. I. (2009). Effects of solid dispersions on the solubility of antibiotics. Pharmaceutical Chemistry Journal, 43 (4), 226-229.

22. MacNally, E. J., & Park, J. Y. (1990). Encyclopedia of Pharmaceutical Technology 2$^{nd}$ edition (Vol, 3). (J. Swarbrick, & J, C. Boylan, Eds.) NY, N.Y.C: Informa Health Care.
23. Mathews, C. K., van Holde, K. E., & Ahern, K. G. (2000). Biochemistry (3rd. ed.). San Francisco, Calif.: Addison Wesley Longman, Inc.
24. Merck Chemicals. (2004, June). Chemistry with a future: white gold. (M. KGaA, Editor) Rtrvd 6/07 from www.merk.de/servlet/PB/show/1359290/IL%20white%20gold.pdf
25. Micaelo, N. M., & Soares, C. M. (2008). Protein structure and dynamics in ionic liquids: insights from molecular dynamics simulation studies, Journal of Physical Chemistry, 112, 2566-2572.
26. Millero, F. J., Ward, G. K., & Chemrkin, P. (1976), Partial specific volume, expansibility, compressibility, and heat capacity of aqueous lysozyme solutions. The Journal of Biological Chemistry, 251 (4), 4001-4004.
27. Parrow, M. W., Burkholder, J. M., Deamer, N. J., & Ramsdell, J. S. (2005). Contaminantfree cultivation of Pfiesteria shumwayae (dinophyceae) on a fish line. Aquatic Microbial Ecology, 39, 97-105.
28. Powroznik, B. (2004). Enhancement of lysozyme stability and activity by polyamines. Biochimie, 651-656.
29. Robinson, G. W., & Cho, C. H. (1999). Role of hydration water in protein folding. Biophysical Journal, 77, 3311-3318.
30. Shiu, Y.-J., Jeng, U.-S., Huang, Y.-S., Lai, Y.-H., Lu, H.-F., Liang, C.-T., et al. (2008, Jul. 15). Global and local structural changes of cytochrome c and lysozyme characterized by a multi-group unfolding process. (T. B. Society, Ed.) Biophysical Journal, 4828-4836.
31. Singh, S., & Singh, J. (2003). Effect of Polyols on the Conformational Stability and Biological Activity of a Model Protein Lysozyme. AAPS PharmSciTech, 101-109.
32. Stevenson, C. L. (2000). Charactorization of protein and peptide stability and solubility in non-aqueous solvents. Current Pharmaceutical Biotechnology, 1, 165-182.
33. Sugar, D. (1952). Measurement of lysozyme activity and the ultraviolet deactivation of lysozyme. Biochim Biophys Acta, 8, 302.
34. Ugwu, S. O., & Apte, S. P. (2004, Mar. 1). The effect of buffers on protein conformational stability. Pharmaceutical Technology, 86-113.
35. Uversky, V. N., & Permyakov, E. A. (2007). Methods in protein structure and stability analysis: conformational stability, size, shape and surface of protein molecules. Hauppauge, N.Y.: Nova Publishers.
36. Wade, L. (2003). Organic chemistry. Upper City River, N.J.: Prentice Hall. Wetlaufer, D. (1973). Nucleation, rapid folding, and globular interchain regions in protins. Proceedings of the National Academy of Sciences of the United States of America, 70 (3), 697-701.
37. White, E. T., Tan, W. H., Ang, J. M., Tait, S., & Litster, J. D. (2007). The density of a protein crystal. Powder Technology, 179 (1-2), 55-58.
38. Worthington Biochemical Coorporation. Lysozyme. Retrieved Aug. 1, 2008, from www.worthington-biochem.com/LY/default.html
39. Yoshizawa-Fujita, M., Fujita, K., MacFarlane, D. R., & Forsyth, M. (2007). A new class of proton-conducting ionic plastic crystals based on organic cations and dihydrogen phosphate. (E. B. V., Ed.) Electrochemistry Communications, 9, 1202-1205.

Example 3

Cyto-Toxicity and Biocompatibility of a Family of Choline Phosphate Ionic Liquids Designed for Pharmaceutical Applications CDHP was demonstrated to improve the thermostability and shelf life of several model proteins, thus exhibiting potential as a stabilizing excipient or solvent for protein therapeutics. Before novel compounds and ionic liquids (Ils) can be used for biomedical applications, comprehensive data is required to establish biocompatibility, including cytotoxicity effects and solution behavior. In this study, five phosphate based anion moieties were analyzed: $H_2PO_4^-$(DHP), dibutyl phosphate (DBP), bis(2-ethylhexyl) phosphate (BEH), bis(2,4,4-trimethylpentyl) phosphinate (TMP), and O,O'-diethyl dithiophosphate (DEP), all paired with the cation choline ©. Toxicity levels for these compounds and Ils and common sugars and salts, were established using a J774 murine macrophage cell line. The sugar trehalose, and the simple salts sodium chloride and choline chloride yielded $EC_{50}$ values of >100, 63 and 34 mM, respectively. The $EC_{50}$ values (mM) of CDHP (20), choline dibutyl phosphate (CDBP) (9.1), and choline O,O'-diethyl dithiophosphate (CDEP) (8.2) are lower than, but within the range of simple salts NaCl (62.8) and choline Cl (33.7). The $EC_{50}$ values of CTMP and CBEH were considerably lower, 0.25 and 0.3 mM, respectively. CDHP and CBEH displayed a 4ollicle response. Osmolality measurements indicated that CDHP, CDBP, and CDEP exhibit nearly complete dissociation in aqueous solution, with osmotic coefficients of 1.0, 0.9, and 0.8, whereas CTMP and CBEH have coefficients of 0.5 and 0.3 and are more molecular in character. A high correlation between the $EC_{50}$ value and the anion mass fraction indicated that anion size and the presence of moderately long and/or branched alkyl chains may affect viability.

CDHP has been shown to dramatically improve the shelf life of cytochrome c when used as the major co-solvent with water, and in solution the protein was shown to retain both structure and activity.[3,8] The ability of proteins to retain a properly folded structure is paramount to their function in vivo and efficacy in therapeutic application. The potential benefit of affording storage and delivery in a liquid vehicle makes formulation in CDHP an alternative to costlier lyophilized products. The aim of this study was to evaluate the cytotoxicity of a panel of choline based solutions and ILs in order to identify the least toxic for continued development as potential components in pharmaceutical formulations. Ionic liquids studied involve choline as a cation and a series of phosphate and phosphinate anions to investigate the possible roles of structural modifications, compared to choline dihydrogen phosphate itself, in the cytotoxicity of this family of compounds. The choline salts of: dihydrogen phosphate (DHP), dibutyl phosphate (DBP), bis(2-ethylhexyl) phosphate (BEH), bis(2,4,4,-trimethylpentyl) phosphinate (TMP), and O,O'-diethyl dithiophosphate (DEP) were investigated. Simple salts and sugars were included for comparison.

Another important consideration in the development of ILs for biological formulation is that the osmotic strength of IL containing solutions must be well-defined. Recent work has shown that many of the ionic liquids that are of interest in bio-applications are not fully ionic; instead they exist as ion pairs in the neat liquid.[9] This observation indicates that an intermediate level of dissociation is occurring for these ILs where the solution behavior is between that of a fully ionic liquid and a molecular solvent such as water. Since the osmolality of the IL could potentially be much lower than one would expect for a simple salt, we have acquired osmolality measurements using a vapor pressure osmometer for the currently investigated family of choline salts.

Results and Discussion.

The structures of the phosphate based solutions including ILs included in this study are shown in FIG. 18. To establish the relative toxicity of these compounds, mouse macrophage cells (J774) were used as a model cell type. The J774 macrophage cell line was chosen due to proven applicability in particulate toxicity and intracellular drug effectiveness studies.[10, 11] Cell viability following exposure to ILs was measured using a resazurin-based fluorometric assay to estimate the number of metabolically active cells in 96-well plates. Viable cells reduce resazurin to fluorescent resorufin whereas nonviable cells do not generate a significant fluorescent signal.

Stock solutions of ionic liquids were prepared in culture medium composed of Dulbecco's modification of Eagle's medium (DMEM) with L-glutamine, 4.5 g/L glucose and sodium pyruvate complemented with 10% fetal bovine serum and 1% penicillin/streptomycin. Cells were exposed to 1:1 serial dilutions of each IL compound in 96-well plates for 48 hours. Each plate contained a media and an untreated cells control. Concentrations ranged from 0.2 to 113 mM, and were optimized for complete concentration-response curves including hormetic effects.

The simple sugar (trehalose) showed incomplete inhibition in the concentration range tested and is reported with an $EC_{50}$>100 mM, while the simple salts (sodium chloride, and choline chloride) had $EC_{50}$ values of 63 and 34 mM respectively (Table 6).

effects as compared to the four-carbon side chains on CDBP (FIGS. 18 and 19); however, these two compounds were approximately twofold more toxic than CDHP (Table 6).

Figure 20:
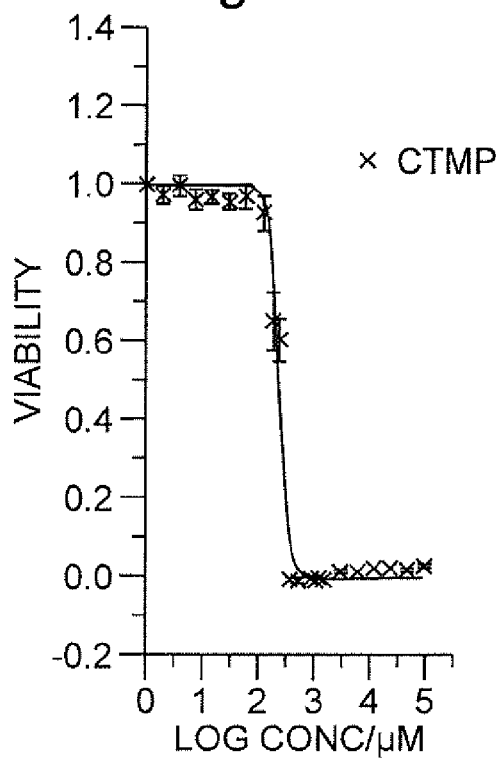
FIG. 20. Dose response curves for J774 indicating toxicity effect of ionic liquid choline bis(2,4,4-trimethylpentyl) phosphate (CTMP). Raw data and fitted concentration curves (dose response model, Equation 1).

The compounds CTMP and CBEH gave $EC_{50}$ values of <0.25 and 0.30 mM, respectively, lower than all the other compounds tested (Table 6). Media based solutions prepared with CTMP appeared to form emulsions or micellar solutions that may have trapped, or even precipitated media nutrients. Due to these low solubility and solution characteristics, the $EC_{50}$ value for CTMP can only be estimated, and is assumed to be lower than 0.25 mM (FIG. 20). Since the $EC_{50}$ of choline chloride did not display toxicity at the lower concentration level where the CTMP and CBEH $EC_{50}$ values occur, it can be concluded that there is not an intrinsic cation effect on cytotoxicity. Thus, the toxicity of CTMP and CBEH can be attributed to the anion and in the case of CTMP and CBEH, the longer and branched alkyl chain substituents.

Figure 21:
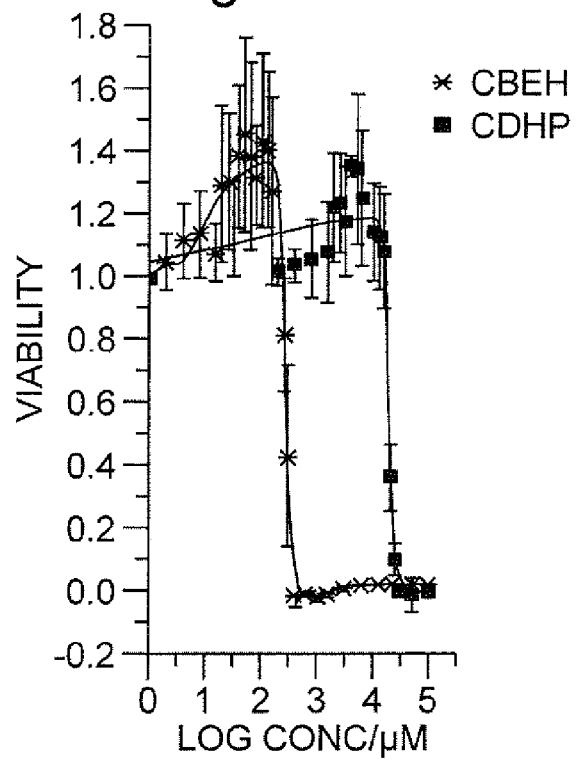
FIG. 21. Dose response curves for J774 indicating 3ollicle effects. Raw data and fitted concentration curves (modified logistic model, Equation 2) for choline bis(2-ethylhexyl phosphate (CBEH) and CDHP.

In the case of both CDHP and CBEH, cell viability increased with increasing concentration before passing through a maximum and eventually falling away with additional increasing ionic liquid concentration, i.e., both compounds induced a subtoxic stimulus or hormetic response (FIG. 21). The inverted U-shaped dose response curves for both data sets were fit with a dose-response model (Statistical analyses, Equation 1) and a modified logistic model that includes a parameter that describes hormesis (Statistical analyses, Equation 2), The $EC_{50}$ values obtained from the two models were within error of one another, and the hormetic model appears to describe the toxicity behavior of CBEH reasonably well. However, the hormetic effect of CDHP showed considerable variability. The significant changes in the character of the hormetic trend for CDHP, especially the

TABLE 6

List of compounds, MWs, mol fractions, Log EC50s, and osmotic coefficients.

| Compound (abbreviation) | MW, g/mol | Anion mass fraction, $\chi^a$ | Log $EC_{50}$, μM (Dose Response Model)[b] | Log $EC_{50}$, μM (Logistic Model)[c] | Osmotic Coef., φ in $H_2O^d$ |
|---|---|---|---|---|---|
| Choline chloride (ChCl) | 139.625 | 0.3 | 4.53 (4) | n/a | 0.86 |
| Sodium chloride (NaCl) | 58.443 | 0.6 | 4.8 (1) | n/a | 0.91 |
| Trehalose (Tre) | 378.33 | n/a | 5.1 (5) | n/a | 1.01 |
| Choline dihydrogen phosphate (CDHP) | 201.158 | 0.5 | 4.31 (4) | 4.28 (6) | 0.98 |
| Choline dibutyl phosphate (CDBP) | 313.366 | 0.7 | 3.96 (3) | n/a | 0.90 |
| Choline bis(2,ethyl hexyl) phosphate (CBEH) | 425.574 | 0.8 | 2.47 (3) | 2.43 (3) | 0.31 |
| Choline bis(2,4,4-trimethyl pentyl) phosphinate (CTMP) | 393.574 | 0.7 | 2.39 (2) | n/a | 0.48 |
| Choline O,O'-diethyl dithiophosphate (CDEP) | 289.382 | 0.6 | 3.91 (2) | n/a | 0.76 |

[a]Anion mass fraction, $\chi = m_i/m$, where $m_i$ = mass of anion, m = total mass of substance in system.
[b]Dose response model as defined in equation 1. Error of last digit in Log $EC_{50}$ value denoted in parentheses.
[c]Modified dose response model as defined in equation 2. Error of last digit in Log $EC_{50}$ value denoted in parentheses.
[d]Osmotic coefficient φ = (osmol/L)/[n x C], where n = number of particles, C = molar concentration of solute, osmol/L = osmolarity. Measured for 100 mM solutions prepared in deionized water.

Figure 19:
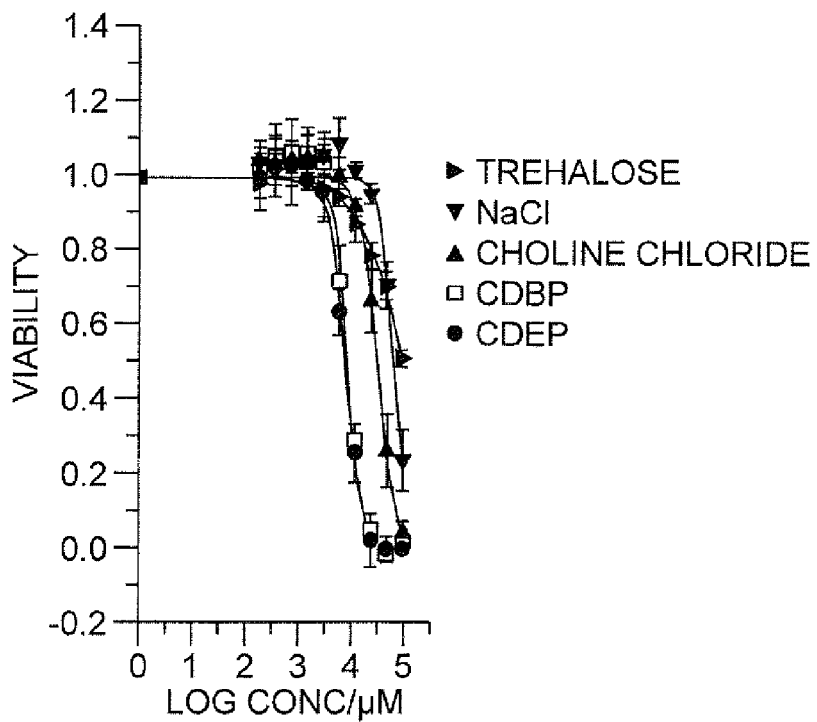
FIG. 19. Dose response curves for J774 indicating toxicity effect of ionic liquids. Raw data and fitted concentration curves (dose response model, Equation 1) are shown.

The $EC_{50}$ values (mM) of CDHP (20), CDBP (9.1), and CDEP (8.2) listed in Table 6 were lower than simple salts, suggesting that they were slightly more toxic, but still within the range of typical physiologic salts as shown in FIG. 19. The $EC_{50}$ value for CDHP is consistent with toxicity trends observed previously (Table 6).[12] The short sulfanyl and sulfanylidene groups on CDEP appear to yield similar toxicity range of hormesis, were not accommodated well by the current model indicating the need for improved hormesis model development, which will be addressed further elsewhere.

In addition, CDHP was observed to exceed the buffer capacity of the complemented media at high concentrations (≥50 mM) as indicated by a color change in the pH indicator. At 100 and 50 mM CDHP, the pH was 6.48 and 6.77 (±0.01)

respectively. After dilution with media to 25 mM, the solution had a pH of 7.52, close to that of the media alone. This concentration is higher than the $EC_{50}$ value for CDHP. Although during the cell based assay subtle changes in pH near the $EC_{50}$ value cannot be ruled out, it is not clearly apparent whether toxicity can be attributed to pH effects where viability decreases as the buffer capacity is approached.

Choline is an essential nutrient, and serves many physiological roles due to its incorporation in membrane components, signaling molecules, and neurotransmitters.[13] It is reported that choline does not permeate cell membranes, but must be transported by a carrier-mediated system.[13] Inverted U-shaped dose-response curves have been reported for choline in cholinergic drug studies, and for high-affinity choline transporters.[13, 14] Brock suggests that the biphasic effect of the dose-response curves indicates that more than one intracellular process is involved.[13] Biphasic dose-response curves indicate complex physiological action, and gave rise to the concept of hormesis described as low-dose stimulation followed by high-dose inhibition.[13, 15, 16] The fact that these effects were not observed with choline chloride or with the other choline-based ionic liquids included in this study raises an interesting question with respect to what exactly is occurring that manifests as the hormetic effect.

To improve the biocompatibility of injected therapeutics the osmolality of such solutions are ideally formulated to be near that of extra- and intracellular fluids. Otherwise the imbalance in the chemical potential of water inside and outside the cells near the injection site will result in a rapid transport of water to/from the cells. This can cause cell injury, resulting in pain at the injection site. Because ionic liquids can exhibit solution behavior ranging from molecular in nature to that of a fully dissociated ionic solution, it is important to understand this behavior in order to predict final solution osmolalities in formulations.[9, 17] Osmolality measurements of ILs formulated at 100 mM in water were determined using a vapor pressure osmometer. From these measurements, osmotic coefficients ($\phi$) in water, which account for the degree of non-ideality of a solution, were calculated so that the degree of dissociation of each ionic liquid could be assessed. CDHP, CDBP, and CDEP have osmotic coefficients of $\phi$=1.0, 0.9, and 0.8 respectively at 100 mM (Table 6), where a value of 1 indicates 100% dissociation. CTMP ($\phi$=0.5) and CBEH ($\phi$=0.3) have very low coefficients (Table 6), and although these ionic liquids are composed of ionic salts, it appears that they may have not dissociated completely. While electrostatic effects can also cause depression in osmotic coefficients, osmotic coefficients at or below 0.5 for CTMP and CBEH seem to indicate more molecular versus ionic solution character.

Although the other compounds were completely miscible with water and complemented media at all concentrations investigated, CTMP formulated at 10 and 100 mM appeared to precipitate at 4° C., and form an emulsion or dispersion at 25° C. and 37° C. The 1 mM CTMP used as the stock solution for the cell based assays did not exhibit the same insolubility profile i.e., CTMP appears to be miscible with water at 1 mM concentrations. Still, the characteristics of the CTMP emulsions remain to be elucidated since potential particle formation in the solutions containing higher levels of CTMP might involve nutrient sequestration which would adversely affect cell viability in addition to lowering the osmolality.

Figure 22:
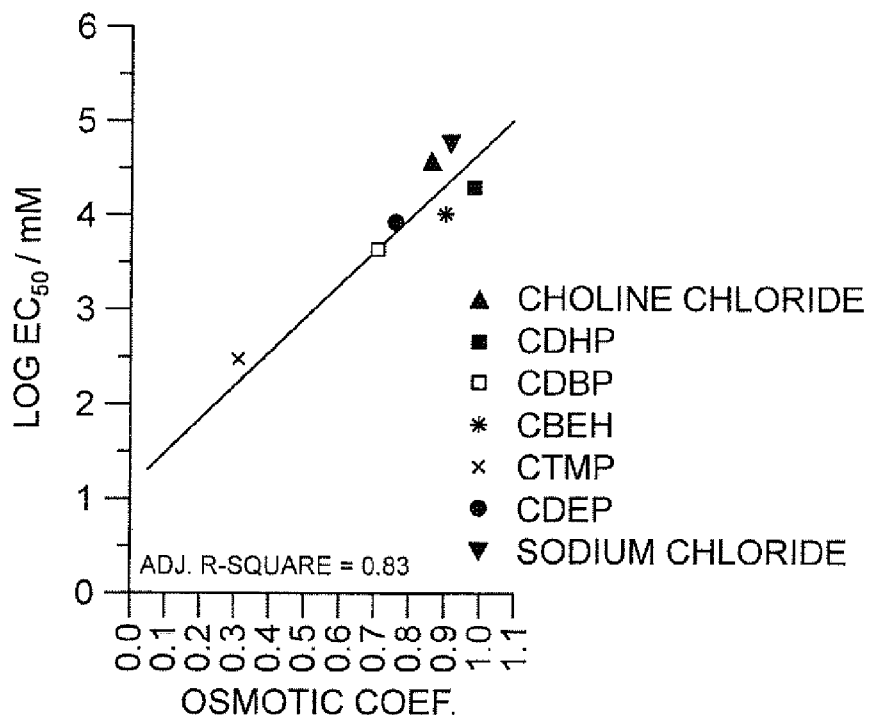
FIG. 22. Effect of osmotic coefficient and anion mass fraction on viability. (a) The osmotic coefficient of each anion is plotted against the Log $EC_{50}$. Adj. R-square=0.83. (b) The anion mass fraction versus $EC_{50}$, mM. The mass fraction ($\chi$) of each anion is expressed as in the equation ($\chi = m_i/m$), where the mass of each component i is defined as its amount $m_i$ divided by the total amount of substance in the system, m. Adj. R-square=0.98. Data analyzed with OriginPro 8, error of last digit in parenthesis.
Figure 22:
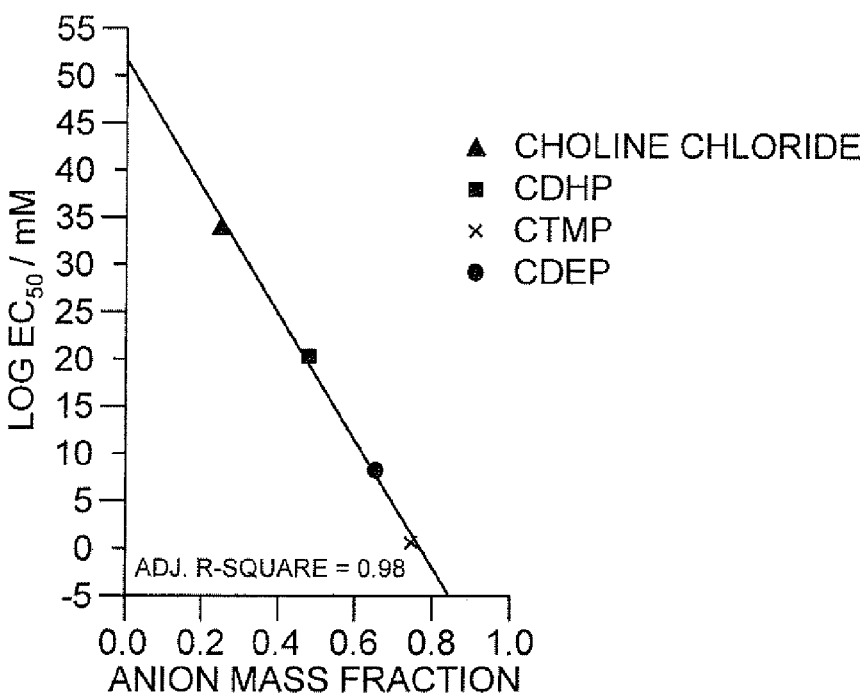

It has been shown for a series of acetate based ILs that higher anion molar concentrations enhanced the dissolution of substrates in the pure IL, but lowered enzyme activity indicating that an optimum ion size is required to satisfy both sufficient substrate solution and enzyme activity conditions.[18, 19] To determine if a similar anion size effect for toxicity could be occurring, the $EC_{50}$/mM value was compared to both the osmotic coefficient and an approximate measure of anion size for this series of choline based ILs (FIG. 22). The anion size is inferred from the calculated mass fraction of anion in the ionic liquid. Since the cation is common to all the salts studied and assuming that their densities are approximately the same, the mass fraction anion is a reflection of anion size. Looking at the $EC_{50}$ values versus the osmotic coefficients for the choline salts, it appears that there is clustering of the more toxic and molecular-like salts (FIG. 22A). Comparison of $EC_{50}$ to the anion-mass-fraction shows that apparent anion size and toxicity are closely correlated (FIG. 22B), with a correlation coefficient of (Adj. R-Square=0.98, OriginPro 8). The trend observed for $EC_{50}$/mM versus anion mass fraction suggests that higher anion mass fractions correlate with higher J774 toxicity (FIG. 22B). This indicates that changes in anion size due to the incorporation of moderately long and or branched alkyl chains, or substitution with sulfur groups may affect viability such as that seen for ILs CTMP, CBEH, and CDEP. The reason for this correlation is not clear, but could be related to interactions with lipid membranes, or possible electronic effects due to the differences in charge distribution of potential ion pairs within the solvent.

The anion effect was also examined through comparison of the ratio of the $EC_{50}$ values of the chloride containing choline reference salt and the $EC_{50}$ for each of the choline based IL compounds tested. The anion effect ratio (AR) (Equation 3) was first used by Stoke to classify the toxicity of anions in ionic liquids, where AR values <5 were considered non-cytotoxic or marginally cytotoxic, and values >5 were described as significantly influencing cytotoxicity, $$AR = \frac{EC_{50}(CCl)}{EC_{50}(CY)}, \quad (3)$$

where CCl stands for choline chloride and CY stands for choline paired with anion, Y.[6] CDHP has the lowest cytotoxicity with AR=1.7, followed by CDBP=3.7. The CDEP AR=4.1 is approaching a borderline value of 5 and could be considered marginally cytotoxic. The AR values for CTMP (137) and CBEH (113) are over an order of magnitude greater than 5, and so these two anions (TMP and BEH) are considered to significantly influence the toxicity of these two ionic liquids, and therefore are not ideal for further exploration as excipients for pharmaceutical application. While the actual mode of CTMP and CBEH anion toxicity has yet to be determined, it appears to be consistent with toxic effects observed for cations with longer alkyl chains.[20, 21] Longer alkyl chains impart the anion with a hydrophobic tail that is lipophilic, and in an effort to escape contact with the aqueous environment it will associate and possible intercalate with cell membranes. Still, the molecular nature of the ion pairs suggested by their osmotic coefficients may impart a mixed cytotoxicity in that an uncharged species introduced to the membrane may enable membrane interactions and increase cytotoxicity.[22]

Materials.

Sodium chloride was purchased from VWR International, $\alpha$-$\alpha$-trehalose dehydrate was purchased from Ferro Pfanstiehl Laboratories. Choline chloride, choline hydroxide, methanol, dihydrogen phosphate, dibutyl phosphate, bis(2-ethylhexyl) phosphate, and O,O'-diethyl dithiophosphate were obtained from Sigma-Aldrich. Bis(2,4,4-trimethylpentyl) phosphinate was obtained from Cytec. All chemicals were used as received, except as otherwise specified. ELGA Purelab Ultra water (18.2 MΩ.cm) was used in the preparation of all water based solutions.

Ionic Liquids.

Choline dihydrogen phosphate (CDHP) was synthesized at Monash University according to previous methods.[3, 23] Choline salts of dibutyl phosphate (CDBP), bis(2-ethylhexyl) phosphate (CBEH), bis(2,4,4-trimethylpentyl) phosphinate (CTMP), and O,O'-diethyl dithiophosphate (CDEP) were synthesized at Monash University as described below. Choline dibutyl phosphate (CDBP) was synthesized via a neutralization reaction as shown in Scheme 2.

Scheme 2: Synthesis of CDBP via a neutralization reaction.

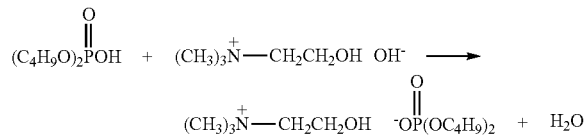

A typical procedure for the synthesis of CDBP is as follows: 3.342 g (0.0159 mol) dibutyl phosphate was dissolved in 4 g of ethanol, a choline hydroxide-methanol solution containing 0.0159 mol of choline hydroxide was added dropwise, and the mixture was stirred at room temperature for more than 4 hrs; the solvent was removed by distillation, and the product was dried under vacuum at 70° C. for at least 2 days. The other three choline ILs were synthesized via the same procedure as that of CDBP, using bis(2-ethylhexyl) phosphate instead of dibutyl phosphate for CBEH, using bis(2,4,4-trimethylpentyl) phosphinate for CTMP, and using O,O'-diethyl dithiophosphate for CDEP.

The resultant salts were characterized using electrospray mass spectrometry and thermogravimetric analysis. Electrospray mass spectroscopy (cone ±35V), m/z (relative intensity, %) for CDBP: ES$^+$, 103.9 ([CH$_3$]$_3$[C$_2$H$_4$OH]N$^+$, 100), 417.4 (M-[CH$_3$]$_3$[C$_2$H$_4$OH]N$^+$, 10); ES$^-$, 153.0 ([C$_4$H$_9$O]OPO$^-$, 7); 209.2 ([C$_4$H$_9$O]OPO$^-$, 100). CBEH: ES$^+$, 103.9 ([CH$_3$]$_3$[C$_2$H$_4$OH]N$^+$, 100); ES$^-$, 321.3 ([C$_8$H$_{17}$O]OPO$^-$, 100). CTMP: ES$^+$, 103.9 ([CH$_3$]$_3$[C$_2$H$_4$OH]N$^+$, 100), 497.5 (M-[CH$_3$]$_3$[C$_2$H$_4$OH]N$^+$, 7); ES$^-$, 289.4 ([C$_8$H$_{17}$]$_2$OPO$^-$, 100); 579.4 ([C$_8$H$_{17}$]$_2$OPOH—[C$_8$H$_{17}$]$_2$OPO$^-$, 10). CDEP: ES$^+$, 103.8 ([CH$_3$]$_3$[C$_2$H$_4$OH]N$^+$, 100); ES$^-$, 156.8 ([C$_2$H$_5$O]SPS$^-$, 18), 184.8 ([C$_2$H$_5$O]$_2$SPS$^-$, 100).

Figure 23:
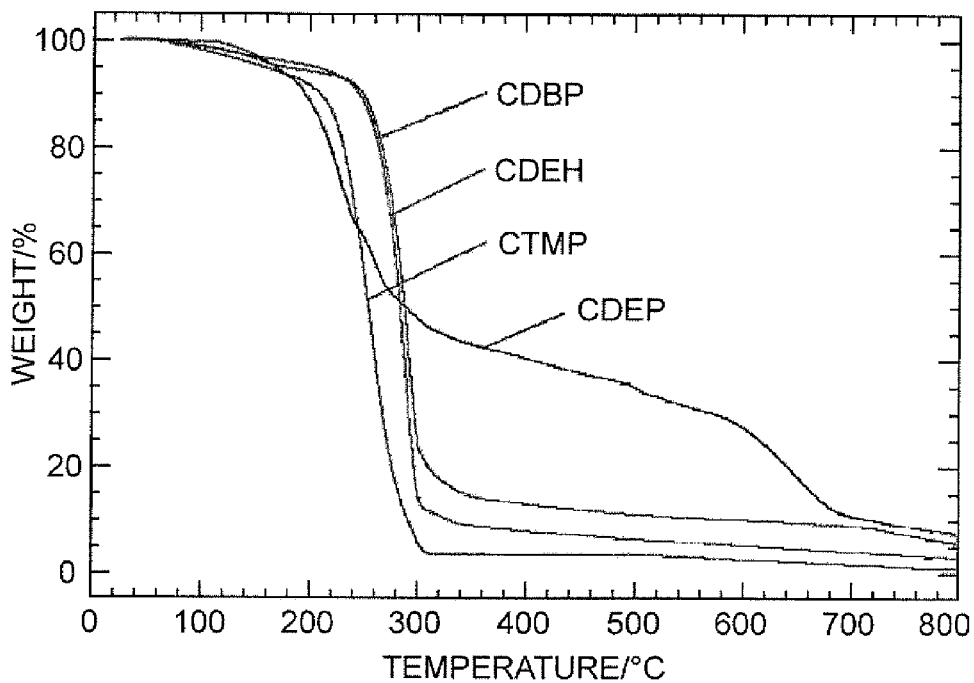
FIG. 23. Thermogravimetric Analysis (PerkinElmer) of choline ILs. Scan rate was 10.0° C./min from room temperature to 800° C. under a nitrogen atmosphere.

A PerkinElmer Thermogravimetric Analyzer (TGA) was used to test thermal stability of the choline ILs. Scan rate was 10.0° C./min from room temperature to 800° C. under a nitrogen atmosphere. See FIG. 23 for thermal traces.

Alkyl chain length and substituent composition were altered for the anions to test the influence of variation in the anion. The chemical structures of the compounds are given in FIG. 18.

Cell Line.

Mouse macrophage cells (J774A.1) were obtained from American Type Culture Collection (ATCC$_R$ Number TIB-67™), Manassas, Va. Cultures of J774A.1 were grown at 37° C. in a humidified atmosphere in a total volume of 10 mL of Dulbecco's modification of Eagle's medium (DMEM, with phenol red) with L-glutamine, 4.5 g/L glucose and sodium pyruvate (Mediatech, 10-013-CM) supplemented with 10% fetal bovine serum (FBS) (Atlanta Biologicals, S11150), 1% 5000 IU penicillin 5000 μg/mL streptomycin (P/S) solution (Mediatech, 30-001-CI), pH 7.53±0.01 under 5% CO$_2$ in 250 mL CellstarR tissue culture flasks (Greiner bio-one). The cells were incubated for up to one week in order to obtain a population between 1×10$^5$ and 1×10$^6$ cells/mL. The cells were scraped, centrifuged, and transferred to 20 mL spinner flasks where they were maintained at a density less than 1×10$^6$ cells/mL. Under these culture conditions, the generation time of the cell line was about 24 h.

Resazurin Metabolism Assay.

All assays were conducted in 96-well Costar cell culture plates (Fisher) at 37° C. The viability of J774 cells exposed to ionic liquids was measured using a fluorometric assay based on the reduction of resazurin (Sigma-Aldrich).24 Resazurin was prepared as a stock solution of 0.437 mM in phosphate buffered saline (PBS, 1×) without calcium and magnesium (Cellgro, Mediatech), and was stored in the dark at 4° C. The stock resazurin solution was diluted to 0.0437 mM in DMEM containing 10% FBS and 1% P/S (full complement media). Stock solutions of ionic liquids (ILs) (1-100 mM) were prepared in full complement media. For comparison of toxicity, solutions of sodium chloride, choline chloride, and trehalose were included in the same concentration range. Each plate contained a negative (no-cells) control, a vehicle (untreated cells) control, and two IL dilution series with three replicates each. Cells in full complement media were plated at a density of 1×10$^4$ cells per well, and were incubated 2 h at 37° C. to allow attachment. After 2 h, the supernatant was removed, and IL supplemented media was added. The cell viability assays were carried out using a 1:1 dilution series in the range of 100 to 0.2 mM (CDHP, CDBP, and CDEP) or 1 to 0.002 mM (CTMP and CBEH). The cells were incubated for 48 h. After 44 h, the IL supplemented media was removed, 0.0437 mM resazurin was added, and the cells were incubated an additional 4 h. Assays were repeated in parallel on cells obtained from 3-5 different dates to allow for variability between cultures. Cell viability was measured at $\lambda_{emis}$=590 nm ($\lambda_{excit}$=560 nm) in a Synergy HT multi-detection microplate reader (Bio-Tek Instruments).

Osmolality.

In order to assess tonicity effects of the ILs, the osmolality of IL solutions (100 mM) prepared in water was measured using a Vapro™ vapor pressure osmometer (Wescor). The osmometer was calibrated against a set of 290, 1000, and 100 mmol/kg osmometry standards prior to each sample.

Statistical Analyses.

Background fluorescence was determined on wells containing resazurin but no cells (negative control), and this value was subtracted from all control and treated wells. Nonlinear regression was used to fit the relationship between cell viability (fluorescence) and the decadic logarithm of the tested concentrations. The general equation for a sigmoidal dose-response with variable slope (four-parameter logistic equation) was used to generate LogEC$_{50}$ values for each compound (OriginPro 8.4) (Equation 1)

$$y = A1 + \frac{(A2 - A1)}{1 + 10^{(\log x_0 - x)p}}, \qquad (1)$$

where x is the concentration of the substance to which the cells are exposed, y is the physiological response normalized for the interval from 1 to 0, A2 is the maximum y value at the top plateau (1, x=0), A1 is the minimum y value at the bottom plateau (O). Log$_{x0}$ (Log EC$_{50}$) is the x value when the response is halfway between the minimum and the maximum. The p value (HillSlope) or slope factor describes the steepness of the curve and is negative, i.e., the curve decrease as x increases (inhibitory response to growth).

In the case of compounds CDHP and CBEH, cell viability appeared to increase with increasing concentration until being reduced with increasing concentration, i.e., these compounds induced a subtoxic stimulus or hormetic effect. The concentration-response curves were fit with both a dose response (four-parameter logistic) model and a modification of the four-parameter logistic model (Equation 2)[25], $$y = A1 + \frac{A2 - A1 + f\exp(-1/x^a)}{1 + \exp\{p[\ln(x) - \ln(x_0)]\}},\quad (2)$$

where f describes the hormetic effect and a governs the rate of hormetic manifestation. A1 and A2 carry the same meaning as in Eqn, 1, however p no longer accurately describes the Hill Slope, and $x_0$ provides a lower bound on the $EC_{50}$ level. The Log $EC_{50}$ values derived from each model are within overlapping confidence intervals. The ability of the modified-four-parameter logistic model to describe the hormetic responses and the level of hormesis for CDHP and CBEH are the subject of a separate body of work.

Conclusion.

This family of choline phosphate salts exhibit a range of toxicities from low (CDHP) and within the range of basic physiologic salts, to high (CTMP and CBEH) based on the anion effect ratio described by Stolte.[6] If a high IL concentration is required to achieve a stabilization effect these ILs might be best implemented as co-formulation stabilizers within slow-release nano- and micro-particles to maximize the biocompatibility. We have observed that the choice of anion can greatly affect the osmotic coefficient of the solution. For example CDHP dissociates completely at 100 mM, with an osmotic coefficient of 1.0, whereas CBEH has an osmotic coefficient of 0.3, and would be considered to have behavior more consistent with a molecular solvent. This would minimize the contribution to osmolality compared to traditional salts.

REFERENCES

1. J. P. Mann, A. McCluskey and R. Atkin, Green Chemistry, 2009, 11, 785-792.
2. N. Byrne and C. A. Angell, Journal of molecular biology, 2008, 378, 707-714.
3. K. Fujita, D. R. MacFarlane, M. Forsyth, M. Yoshizawa-Fujita, K. Murata, N. Nakamura and H. Ohno, Biomacromolecules, 2007, 8, 2080-2086.
4. S, N. Baker, T. M. McCleskey, S. Pandey and G. A. Baker, Chemical communications (Cambridge, England), 2004, 940-941.
5. B. Jastorff, R. Stormann, J. Ranke, K. Molter, F. Stock, B. Oberheitmann, W. Hoffmann, J. Hoffmann, M. Nuchter, B. Ondruschka and J. Filser, Green Chemistry, 2003, 5, 136-142.
6. S. Stolte, J. Arning, U. Bottin-Weber, M. Matzke, F. Stock, K. Thiele, M. Uerdingen, U. Welz-Biermann, B. Jastorff and J. Ranke, Green Chemistry, 2006, 8, 621-629.
7. M. Matzke, S. Stolte, K. Thiele, T. Juffernholz, J. Arning, J. Ranke, U. Welz-Biermannd and B. Jastorff, Green Chemistry, 2007, 9, 1198-1207.
8. K. Fujita, M. Forsyth, D. R. MacFarlane, R. W. Reid and G. D. Elliott, Biotechnology and bioengineering, 2006, 94, 1209-1213.
9. K. J. Fraser, E. I. Izgorodina, M. Forsyth, J. L. Scott and D. R. MacFarlane, Chemical communications (Cambridge, England), 2007, 3817-3819.
10. D. M. Brown, K. Donaldson and V. Stone, Respiratory research, 2004, 5, 1-12.
11. E. L, Wright, D. C. Quenelle, W. J. Suling and W. W. Barrow, Antimicrobial agents and chemotherapy, 1996, 40, 2206-2208.
12. R. M. Vrikkis, K. J. Fraser, K. Fujita, D. R. Macfarlane and G. D. Elliott, Journal of biomechanical engineering, 2009, 131, 074514.
13. M. Brock, A. C. Nickel, B. Madziar, J. K. Blusztajn and B. Berse, Brain research, 2007, 1145, 1-10.
14. J. F. Flood, D. W. Landry and M. E. Jarvik, Brain research, 1981, 215, 177-185.
15. E. J. Calabrese and L. A. Baldwin, Trends in pharmacological sciences, 2002, 23, 331-337.
16. E. J. Calabrese and L. A. Baldwin, Critical reviews in toxicology, 2001, 31, 353-424.
17. G. D. Elliott, R. Kemp and D. R. MacFarlane, in Ionic Liquids: Industrial Applications for Green Chemistry, eds. N. Plechkova, K. Seddon and R. Rogers, ACS, 2009, pp. 1-13.
18. H. Zhao, G. A. Baker, Z. Song, O. Olubajo, T. Crittle and D. Peters, Green Chemistry, 2008, 10, 696-705.
19. H. Zhao, C. L. Jones, G. A. Baker and J. V. Cowins, Green Chemistry, 2009, 11, 1128-1138.
20. S. Stolte, M. Matzke, J. Arning, A. Boschen, W.-R. Pitner, U. Welz-Biermann, B. Jastorff and J. Ranke, Green Chemistry, 2007, 9, 1170-1179.
21. R. A. Kumar, N. Papaiconomou, J. M. Lee, J. Salminen, D. S. Clark and J. M. Prausnitz, Environmental toxicology, 2009, 24, 388-395.
22. E. Fulladosa, J. C. Murat, J. C. Bollinger and I. Villaescusa, The Science of the total environment, 2007, 377, 207-213.
23. K. Fujita, D. R. MacFarlane and M. Forsyth, Chemical communications (Cambridge, England), 2005, 4804-4806.
24. B. Page, M. Page and C. Noel, International Journal of Oncology, 1993, 3, 473-476.
25. N. Cedergreen, C. Ritz and J. C. Streibig, Environmental toxicology and chemistry/SETAC, 2005, 24, 3166-3172.

Example 4

High-dose Interleukin-2 (IL-2) is an FDA approved therapy for the treatment of malignant melanoma and renal cancers. IL-2 is administered systemically (i.v.) and leads to disease regression in 15-20% of stage IV metastatic melanoma patients. However, IL-2 is associated with grade 3 and 4 side effects and this significantly impacts its therapeutic use. The development of alternative administration strategies is limited by IL-2 instability in solution. In recent years a family of low-melting point salts, termed 'ionic liquids', have gained attention for their ability to increase protein stabilization in solution.

The aim of the current study was to determine if choline dihydrogen phosphate (C-DHP) could function as a stabilizing excipient for IL-2 in liquid formulation.

Methods.

The effect of C-DHP on IL-2 thermal stability was measured between 15° C. and 75° C. by circular dichroism at 222 nm. The cytotoxicity of increasing concentrations of C-DHP was measured in mouse splenocytes and B16-F10 melanoma cells by trypan blue exclusion and resazurin reduction assay. The biological activity of IL-2 and C-DHP-IL2 was determined by flow cytometry using HT-2 T cells, a cell line that requires IL-2 to survive and proliferate.

Results.

Figure 24:
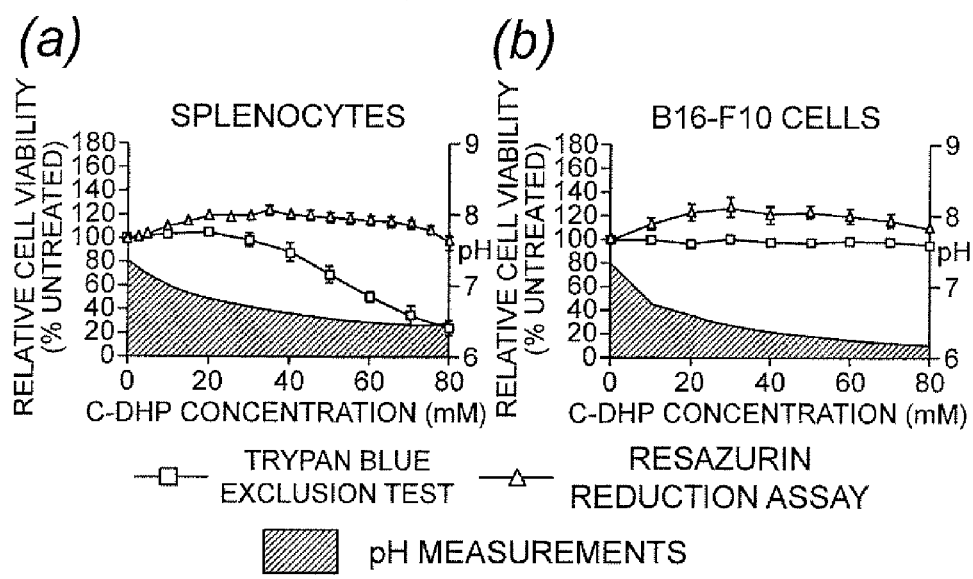
FIG. 24. C-DHP cytotoxic concentration (40 mM) correlates with pH changes. Freshly isolated spleen leucocytes or B16-F10 cells, were cultured in RMPI 1640 or DMEM F12 complete medium respectively, supplemented with up to 80 mM C-DHP. At T0, culture medium pH was measured and at T+24$^h$ cell viability was measured by trypan blue exclusion (black line) or resazurin reduction assay (grey line). A) Up to 40 mM, C-DHP has no significant cytotoxicity toward primary cell cultures of splenocytes. However, at >40 mM C-DHP, culture medium pH is <6.5 and cell viability diminishes. B) Despite a dramatic reduction of pH, C-DHP doesn't demonstrate any significant cytotoxic activity against B16-F10 cells, n=18 from 6 independent experiments (right chart, grey line=resazurin reduction assay, black line=trypan blue exclusion).
Figure 25:
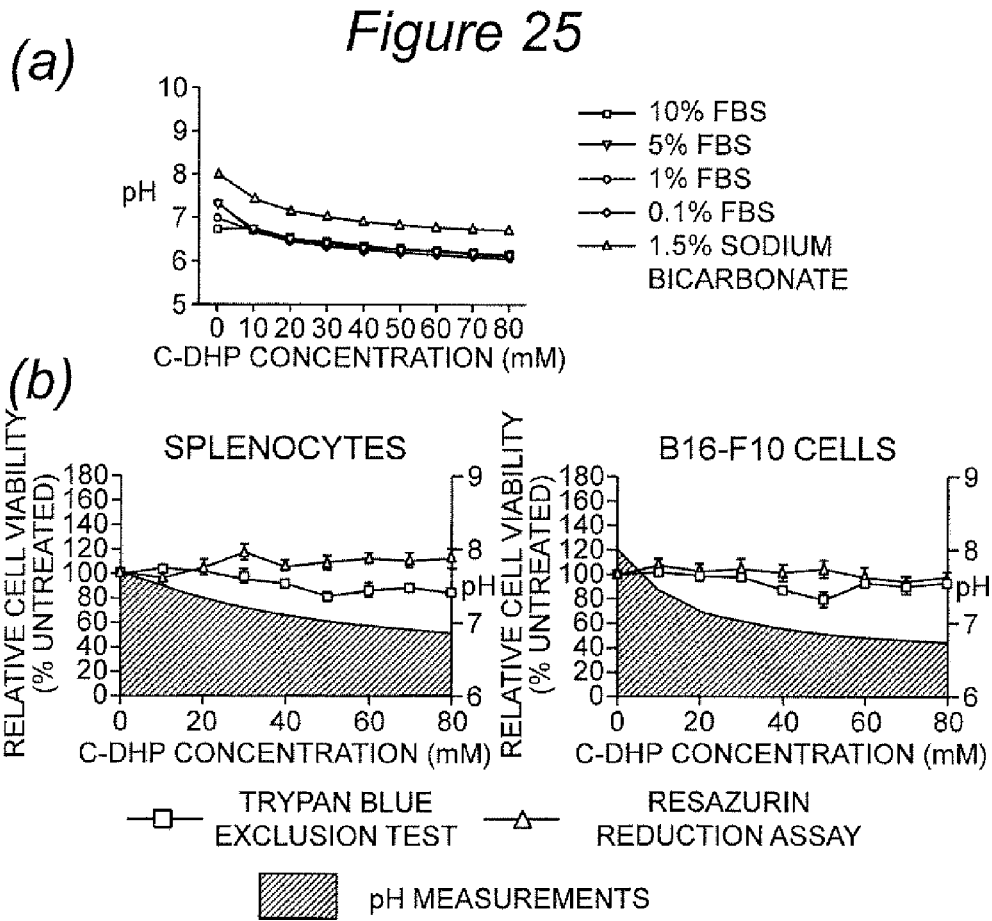
FIG. 25. C-DHP biocompatibility in vitro increases under buffered conditions. A) Effect of fetal bovine serum (FBS) content or sodium bicarbonate addition on complete RPMI 1640 medium pH was measured. While FBS content had no significant effect on C-DHP culture medium acidification, 1.5% (w/v) sodium bicarbonate maintained pH within physiological range. B) Freshly isolated mouse spleen leucocytes or B16-F10 cells were cultured in buffered (1.5% (w/v) sodium bicarbonate) RMPI 1640 or DMEM F12 complete medium supplemented with ≤80 mM C-DHP. At T0, culture media pH was measured and at $T+24^h$ cell viability was measured using trypan blue exclusion (black line) or resazurin reduction assays (grey line). Under buffered culture medium conditions, no cytotoxic activity was detected toward either cell type within a 0-80 mM C-DHP range. N=15 from 6 independent experiments.
Figure 26:
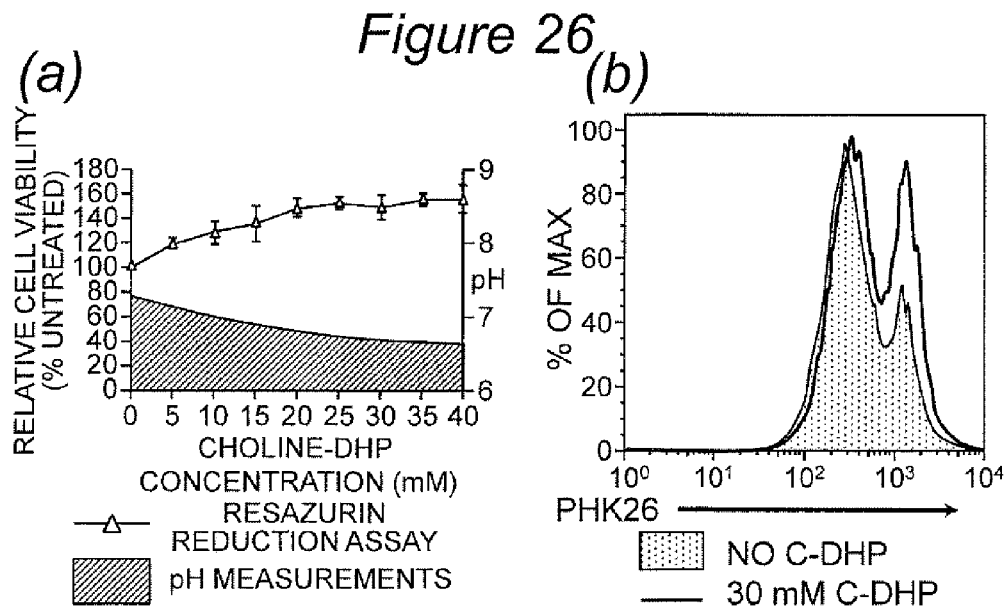
FIG. 26. C-DHP inhibits IL-2 activity in vitro in the absence of pH control. A) HT-2 cells were grown in complete RPMI 1640 medium supplemented with 100 U IL-2 and ≤40 mM C-DHP. Cell viability at $T+24^h$ was measured by resazurin reduction assay. B) HT-2 cells were stained with PKH26 and incubated with 100 U IL-2 in complete RPMI 1640 medium containing 0 or 30 mM C-DHP. At $T+24^h$, cell proliferation was quantified by flow cytometry. While C-DHP has no immediate cytotoxic effect toward HT-2 lymphocytes, a low concentration of the ionic liquid dramatically reduced IL-2 induced cell proliferation in vitro. N=9 from 3 independent experiments.
Figure 27:
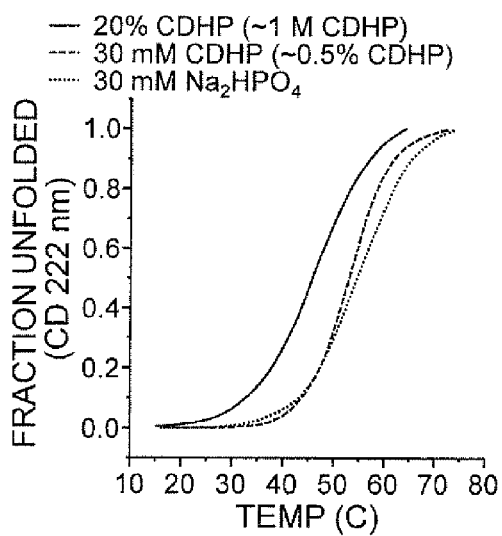
FIG. 27. C-DHP does not impact IL-2 thermo-stability but increases IL-2-dependent HT-2 cell viability under buffered conditions in vitro. A) IL-2 thermal stability was measured between 15-75° C. by circular dichroism at 222 nm. In the presence of 30 mM C-DHP, the melting point of IL-2 was not modified. B) and C) HT-2 cells were stained with PKH26 and incubated with IL-2 (100 U) in complete RPMI 1640 buffered medium containing 0 or 30 mM C-DHP. At $T+72^h$, cell proliferation was quantified by flow cytometry and cell viability measured based on morphological criteria. C-DHP did not significantly affect IL-2-induced HT-2 lymphocyte proliferation under buffered conditions but significantly improved cell viability. n=9 from 3 independent experiments.
Figure 27:
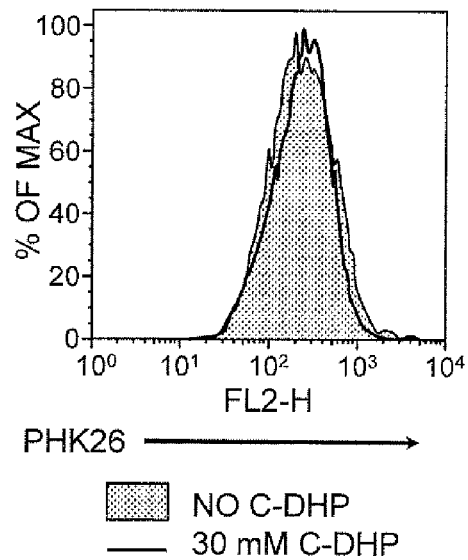
Figure 27:
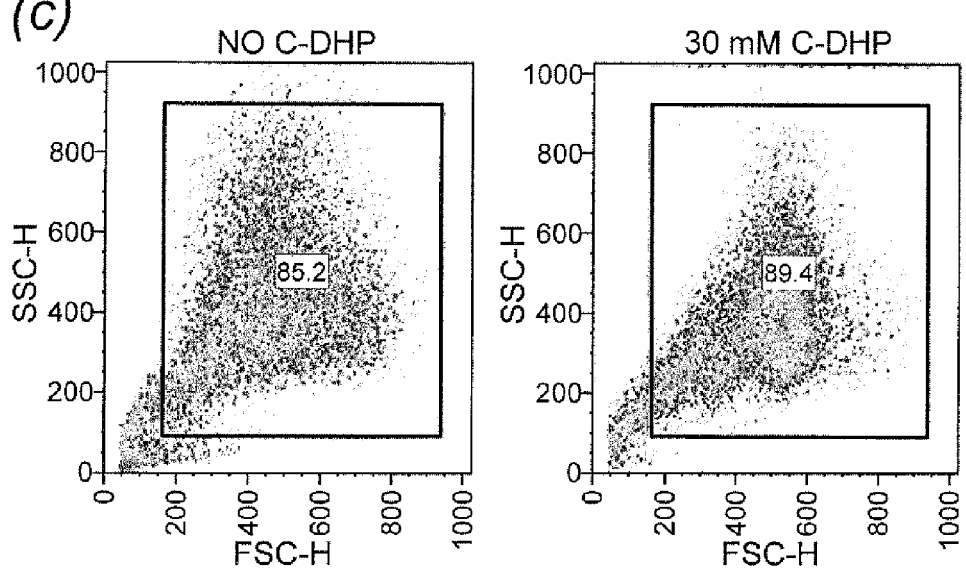

C-DHP at final culture medium concentrations of 1-30 mM was not cytotoxic to splenocytes or B16-F10 melanoma cells (FIG. 24). However at C-DHP concentrations of >35 mM, C-DHP caused significant culture medium acidification and cell cytotoxicity, effects that were abrogated by the addition of sodium bicarbonate (FIG. 25). Under pH-buffered conditions (final culture medium pH7.2-4), 30 mM C-DHP did not significantly modify the IL-2 melting (unfolding) temperature (without C-DHP Tm=53.9° C.; with CDHP Tm=52.3° C.) or IL-2-dependant HT-2 cell proliferation. However, when HT-2 cells were stimulated to undergo proliferation (FBS; 5% or 10% (v/v)), 30 mM C-DHP-IL-2 significantly improved HT-2 cell viability as compared to cells treated with IL-2 alone (FIGS. 26 and 27).

Conclusions.

IL-2 is readily soluble in a C-DHP ionic liquid, pH buffering is required when [C-DHP]>30 mM and, when used in a buffered solution, C-DHP significantly improves IL-2 activity in vitro.

Example 5

Evidence for Choline Dihydrogen Phosphate Enhanced Thermal Stability for Interleukin-2

Materials.

Choline dihydrogen phosphate (CDHP) was prepared by the Monash group by standard methods (Fujita, 2005; Fujita, 2007). CDHP has a melting temperature just over 100° C., and can be rendered liquid with the addition of a small amount of water.

Solution Formulation.

Lyophilized IL-2, human (GenScript) was reconstituted to 1 mg/mL with sterile water and allowed to hydrate for 4 hours at 4° C. prior to preparing working protein solutions, All working protein solutions were allowed to equilibrate at 4° C. overnight before using. IL-2 samples for CD measurements were prepared at a concentration of 0.03 mg/mL for use in the 1.0 cm cuvet and at 0.38 mg/mL for use in the 0.1 cm cuvet by combining appropriate volumes of (1) reconstituted 1 mg/mL IL-2 with (2) a stock solution of CDHP at pH 7.40 or (3) $NaH_2PO_4$ solution at pH 7.40. The final concentration of salts in the test solutions were (1) 30 mM $NaH_2PO_4$, (2) 30 mM CDHP, (3) 185 mM CDHP, or (4) 680 mM CDHP. For comparison, 680 mM CDHP is ~12% (w/w). These solutions are distinctly different from the choline "buffer" solutions recently described which exhibit a buffering action around pH 7.2 (MacFarlane, 2010).

Circular Dichroism.

Far ultraviolet CD spectra were obtained on a JASCO J-715/J-720 spectropolarimeter calibrated with (1S)-(+)-10-camporsulfonic acid, ammonium salt. Spectra were obtained in 1.0 and 0.1 cm path length quartz cuvets depending on concentration of IL-2 in solution. Spectra (five accumulations for each sample) were acquired using a scanning speed of 10 nm/min, data pitch of 0.5 nm, response of 1 sec and bandwidth equal to 1.0 nm. Variable temperature scans were run at 30° C./hour with a data pitch of 0.5° C., response of 1 sec and bandwidth of 1.0 nm while monitoring ellipticity at 222 nm. Variable temperature data was normalized such that the lowest and highest signals correspond to 0 and 1 respectively. Protein concentrations were determined on stock solutions prior to transfer to the cuvets and on aliquots taken from the cuvets after experimental runs were complete using a Bicinchoninic acid (BCA) protein assay kit (Pierce) with reconstituted IL-2 and bovine serum albumin (BSA) as standards.

Spectral deconvolution was done using the Dichroweb online server, http://dichroweb.cryst.bbk.ac.uk accessed on Nov. 10, 2010. Secondary structure analyses of IL-2 in the absence and presence of CDHP were determined by fitting far-UV CD data using the published analysis algorithms CDSSTR (reference set 4, 7 and SP175), CONTIN (reference set 4, 7 and SP175), SELCON 3 (reference set 4, 7 and SP175), and K2d using the online server DICHROWEB (Sreerama, 2000; Whitmore, 2004). The results from the different algorithms and databases were compared to assess which was the most appropriate method for IL-2 at the conditions studied. The normalized root mean square standard deviation (NRMSD), and correspondence of the calculated and experimental secondary structure were used to select the best deconvolution (Whitmore, 2004).

Results

Circular Dichroism.

The NRMSD values were above 0.1 using the CONTIN and SELCON algorithms, the reported error was high for the Kd2 algorithm for the highest concentration of CDHP used, and the correlation between experimental and calculated spectra were poorer when using CONTIN, SELCON, or K2d algorithms (Whitmore, 2004). With NRMSD values all below 0.1, and excellent correspondence of the calculated and experimental secondary structure, the CDSSTR algorithm using reference sets 4, 7, and SP175 proved to be the best method for assessing secondary structure for IL-2. Out of the three databases used, reference set 7 yielded the lowest NRMSD values and the closest spectral fits, and the fit parameters from this method are reported in Table 7. The reported secondary assignments from CDSSTR are split into six classes: regular α-helix, distorted α-helix, regular β-sheet, distorted β-sheet, turns, and unordered (Sreerama, 2000). The regular and distorted α-helix, and β-sheet content have been combined for this report (Table 7).

Figure 28:
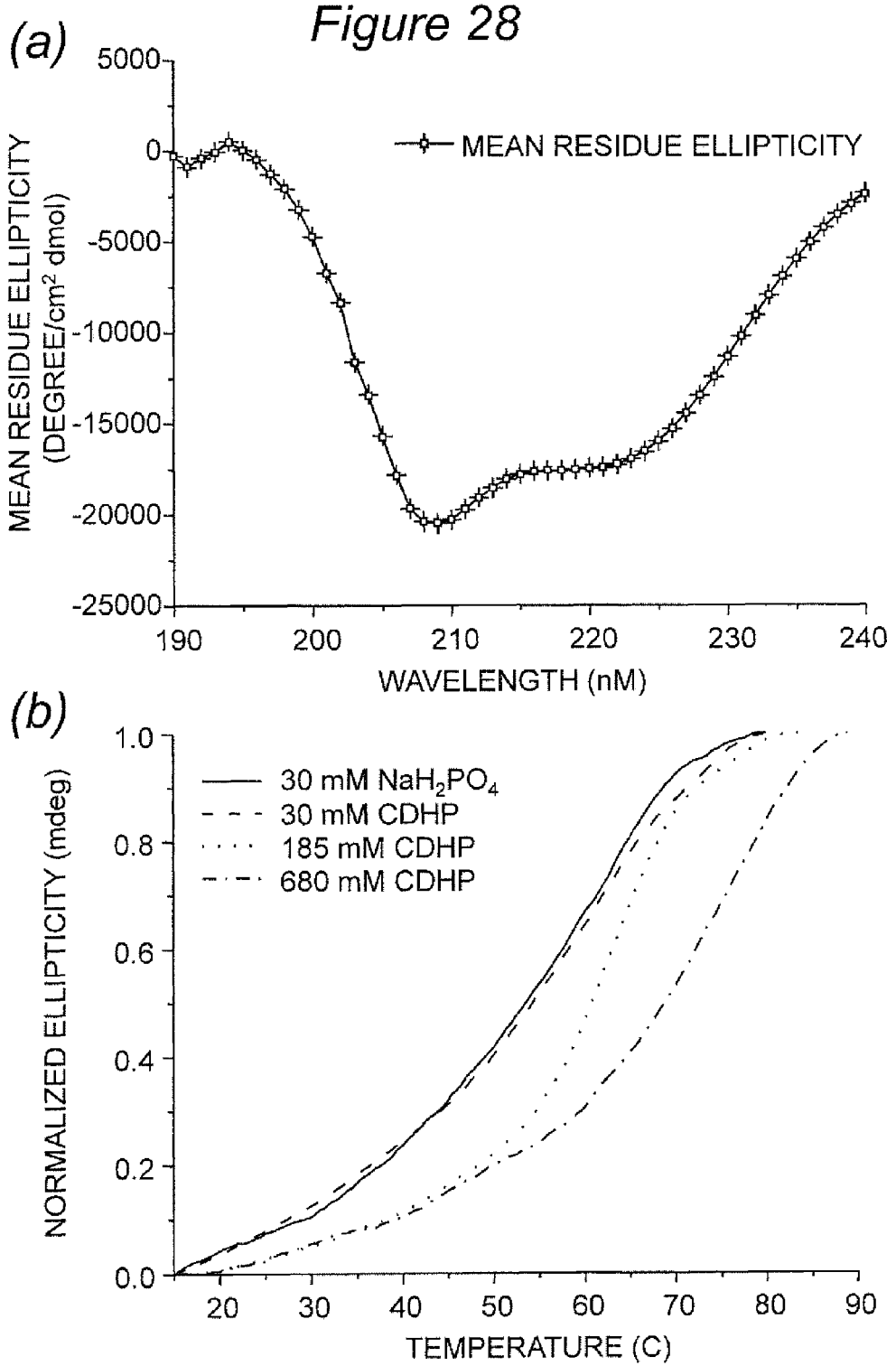
FIG. 28. (A) Representative Dichroweb circular dichroism spectral output. IL-2 in 680 mM CDHP, pH 7.40. Experimental (input) data plotted with crosses, the calculated spectrum derived from the calculated output secondary structure plotted with open boxes. (B) Circular dichroism temperature denaturation curves for IL-2 in (straight) 30 mM $NaH_2PO_4$, (dash) 30 mM CDHP, (dot) 185 mM CDHP, and (dash-dot) 680 mM CDHP, all at pH 7.40. The CD signal was monitored at 222 nm, adjusted by the mean-residue-weight, and normalized so that the lowest and highest signal in each scan was set to 0 and 1 respectively.

In the absence (30 mM $NaH_2PO_4$) or presence of 30 mM CDHP, the α-helix and turn content of IL-2 were found to be comparable, and a slight increase of β-sheet with decrease in unordered content seen in the presence of 30 mM CDHP (Table 7). As the CDHP content was increased to 185 mM, the β-sheet content stabilized, and α-helix content increased with a further decrease in unordered content (Table 7). With 680 mM CDHP, the α-helix content increased more, with turn and unordered content decreasing further (Table 7). A representative graph of the experimental spectra superimposed with the calculated spectra is shown in FIG. 28A.

TABLE 7

Secondary structure analyses of IL-2 in the absence and presence of CDHP

| | Secondary Structure Content[1] | | | | Rescan, % Change[2] | | | |
|---|---|---|---|---|---|---|---|---|
| | 30 mM NaH$_2$PO$_4$ | 30 mM CDHP | 185 mM CDHP | 680 mM CDHP | 30 mM NaH$_2$PO$_4$ | 30 mM CDHP | 185 mM CDHP | 680 mM CDHP |
| α-Helix | 0.40 | 0.42 | 0.47 | 0.53 | −40 | −43 | −66 | −68 |
| β-Sheet | 0.13 | 0.18 | 0.19 | 0.17 | 54 | 11 | 32 | 24 |
| Turns | 0.17 | 0.17 | 0.17 | 0.13 | 6 | 6 | 18 | 38 |
| Unordered | 0.30 | 0.23 | 0.19 | 0.16 | 23 | 70 | 116 | 181 |
| NRMSD | 0.016 | 0.018 | 0.013 | 0.002 | | | | |
| T$_m$, C[3] | 61.7[4] | 60.2[4] | 63.0[5] | 74.2[5] | | | | |

[1]CD spectra were measure at 25° C. prior to running variable temperature profile. All IL-2 solutions were at pH 7.40. Low point analyzed was 190 nm for each set. The secondary structure contents were determined as outlined in Materials and Methods using the CDSSTR algorithm and reference set 7.
[2]Sample rescanned from 260 to 178 nm after cooling and thermastatting at 25° C. for 15 minutes. Percent change was then calculated for before and after temperature scanning to estimate loss in ordered secondary structure as an assessment of reversibility.
[3]Melting temperature (Tm) calculated by taking the first derivative of the temperature scan. The error in the reported values is less than 3.3%.
[4]n = 3.
[5]n = 2.

The melting temperature (T$_m$) of IL-2 was measured at 222 nm in 30 mM NaH$_2$PO$_4$, 30 mM CDHP, 185 mM CDHP, and 680 mM CDHP all at pH 7.40. At the end of the initial thermal scan, the samples were allowed to cool and were thermostated 15 minutes at 25° C. before rescanning to assess reversibility of the unfolding reaction. The normalized CD thermal denaturation scans appear to indicate cooperative transition behavior (FIG. 28B). The protein at 85° C. still had significant CD signal (data not shown) indicating that thermally unfolded IL-2 retains some secondary structure. The high tension voltage (data not shown) reveals an increased absorbance upon melting indicating that unfolded IL-2 aggregates sufficiently to scatter light. The IL-2 solutions made with 185 and 680 mM CDHP contained macroscopically observable precipitates upon removal from the instrument. Spectral rescans confirmed the losses of α-helix content with increases in unordered content and β-sheet structure (Table 7). The T$_m$ for IL-2 in 30 mM NaH$_2$PO$_4$ was 61.7° C. (Table 1). The T$_m$ was slightly changed in the presence of 30 mM CDHP (T$_m$=60.2° C.) or 185 mM CDHP (T$_m$=63.0° C.) (Table 7). However, at 680 mM CDHP [~12.3% (w/w)], the T$_m$ increased up to 74.2° C., an increase of 12.5° C. indicating an increased structural stability and resistance towards thermal unfolding (FIG. 28B, Table 7). These values compare well to those determined calorimetrically where the T$_m$ was 66° C. for 1 mg/mL IL-2 in 20 mM sodium phosphate, 150 mM NaCl, pH 7.5 (Wang, 2008), Discussion The investigation of the temperature dependence of the unfolding of proteins is often utilized as a method to provide accelerated stability studies. Although an increase in T$_m$ is often interpreted as an indication of increased protein stability which sometimes correlates with an increased shelf life, the fact that IL-2 melting was not fully reversible means that a direct correlation between the melting temperature and conformational stability cannot be firmly established. The shape of the unfolding transition does appear to indicate a cooperative transition, but the plateau for pre-transition region is less defined than normally seen for a pure protein and may indicate a heterogeneous population of folded structures. An increase in T$_m$ indicates a possibility to thermodynamically stabilize IL-2 using CDHP as a formulation excipient, but the results also show that IL-2 is kinetically unstable in that it readily aggregates upon unfolding/refolding similar to that seen previously for IL-2 in 5% glucose, 10 mM NaOAc, pH 4.0 (Arakawa, 2001).

IL-2 contains one disulfide bond, and the possible presence of reduced IL-2 in these solutions has not been ruled out (Brandhuber, 1987). Previously, it was observed that the far-UV CD spectra of the native and reduced forms of IL-2 show that both forms have ordered structures compared to IL-2 denatured in guanidine HCl, although the reduced form does have less α-helix content than native IL-2 (Yamada, 1987). However, near-UV CD revealed that the reduced form appears to not have a rigid tertiary structure and is quite similar to IL-2 denatured in the presence of guanidine HCl (Yamada, 1987). Further investigation into the influence of the thiol-disulfide couple on IL-2 stability in the presence of CDHP, or additives intended to reduce aggregation remain to be carried out. Still the increases observed in IL-2 ordered structure as the concentration of CDHP is increased do tend support positive effects on conformational stability and as such shows that CDHP holds promise as a stabilizing excipient.

REFERENCES

T. Arakawa, J. S. Philo, Y. Kita, Kinetic and thermodynamic analysis of thermal unfolding of recombinant erythropoietin, *Biosci. Biotechnol. Biochem.* 2001, 65(6), 1321-1327.
S. Branchu, R. T. Forbes, P. York, H. Nyqvist, A central composite design to investigate the thermal stabilization of lysozyme, *Pharm. Res.* 1999, 16(5), 702-708.
B. J. Brandhuber, T. Boone, W. C. Kenny, D. B. McKay, Three-dimensional structure of interleukin-2, *Science*, 1987, 238(4834), 1707-1709.
N. Byrne, L.-M. Wang, J.-P. Belieres, C. A. Angell, Reversible folding-unfolding, aggregation protection, and multi-year stabilization, in high concentration protein solutions, using ionic liquids. *Chem. Commun.* 2007, 2714-2716.
D. Constantinescu, C. Herrmann, H. Weingartner. Patterns of protein unfolding and protein aggregation in ionic liquids. *Phys. Chem. Chem. Phys.* 2010, 12, 1756-1763.
K. Fujita, D. R. MacFarlane, M. Forsyth, M. Yoshizawa-Fujita, K. Murata, N. Nakamura, H. Ohno, Solubility and stability of cytochrome c in hydrated ionic liquids: Effect of oxo acid residues and kosmotropicity, *Biomacromolecules* 2007, 8, 2080-2086,
K. Fujita, M. Forsyth, D. R. MacFarlane, R. W. Reid, G. D. Elliott, Unexpected improvement in stability and utility of cytochrome c by solution in biocompatible ionic liquids, *Biotechnology and Bioengineering* 2006, 94(6), 1209-1213.

K, Fujita, D. R. MacFarlane, M. Forsyth, Protein Solubilising and Stabilising Ionic Liquids, *Chem. Commun.* 2005, 4804-4806.

J. Geigert, N. Solli, P. Woehleke, S. Vemuri, Development and shelf-life determination of recombinant interleukin-2 (Proleukin), in Stability and Characterization of Protein and Peptide Drugs Case Histories, Y. J. Wang, R. Pearlman, Eds., Plenum Press: New York, 1993, pp. 249-263.

A. Hédoux, F. Affouard, M. Descamps, Y. Guinet, L. Paccou, Microscopic description of protein thermostabilization mechanisms with disaccharides from Raman spectroscopy investigations, *J. Phys.: Condens. Matter* 2007, 19, 205142.

D. Hekmat, D. Hebei, S. Joswig, M. Schmidt, D. Weuster-Botz, Advanced protein crystallization using water-soluble ionic liquids as crystallization additives, *Biotechnol. Lett.* 2007, 29, 1703-1711.

B. Landgraf, F. E. Cohen, K. A. Smith, R. Gadski, T. L. Ciardelli, Structural significance of the C-terminal amphiphilic helix of interlekin-2, *J. Biol. Chem.* 1989, 264(2), 816-822.

D. R. MacFarlane, R. Vijayaraghavan, H. N. Ha, A. Izgorodin, K. D. Weaver, G. D. Elliott, Ionic liquid "buffers"—pH control in ionic liquid systems, *Chem. Comm.* 2010, 46, 7703-7705.

D. S. Maclean, Q. Qian, C. R. Middaugh, Stabilization of proteins by low molecular weight multi-ions, *J. Pharm. Sci.* 2002, 91(10), 2220-2229.

S. B. Petersen, V. Jonson, P. Fojan, R. Wimmer, S. Pedersen, Sorbitol prevents the self-aggregation of unfolded lysozyme leading to an up to 13° C. stabilization of the folded form, *J. Biotechnol.* 2004, 114, 269-278.

S. Singh, J. Singh, Effect of Polyols on the conformational stability and biological activity of a model protein lysozyme, *AAPS PharmSciTech.* 2003, 4(3), Article 42.

N. Sreerama, R. W. Woody, Estimation of protein secondary structure from circular dichroism spectra: comparison of CONTIN, SLECON, and CDSSTR methods with an expanded reference set, *Anal. Biochem.* 2000, 287, 252-260.

R. Vijayaraghavan, A. Izgorodin, V. Ganesh, M. Surianarayanan, D. R. MacFarlane, Long-term structural and chemical stability of DNA in hydrated ionic liquids, *Angew. Chem. Int. Ed.* 2010, 49, 1631-1633.

R. M. Vrikkis, K. J. Fraser, K. Fujita, D. R. MacFarlane, G. D. Elliott, Biocompatible ionic liquids: A new approach for stabilizing proteins in liquid formulation, *J. Biomech. Eng.* 2009, 131, 074514.

W. Wang, K. Antonsen, Y. J. Wang, D. Q. Wang, pH dependent effect of glycosylation on protein stability, *Eur. J. Pharm. Sci.* 2008, 22, 120-127.

L. Whitmore, B. A. Wallace, DICHROWEB, an online server for protein secondary structure analyses from circular spectroscopic data, *Nucl. Acids Res.* 2004, 32, W668-W673.

T. Yamada, A. Fujishima, K. Kawahara, K. Kato, O, Nishimura, Importance of disulfide linkage for constructing the biologically active human interleukin-2, *Arch. Biochem. Biophys.* 1987, 257(1), 194-199.

The foregoing is illustrative of the present invention, and is not to be construed as limiting thereof. The invention is defined by the following claims, with equivalents of the claims to be included therein. All publications, patent applications, patents, patent publications, and other references cited herein are incorporated by reference in their entireties for the teachings relevant to the sentence and/or paragraph in which the reference is presented.

That which is claimed is:

1. A parenterally injectable pharmaceutical composition comprising:
   (a) from 0.01 to 40 weight percent choline dihydrogen phosphate;
   (b) an added base included in an amount not greater than 40 weight percent, wherein said added base is choline hydroxide;
   (c) at least 60 weight percent water; and
   (d) from 0.01 to 10 weight percent active compound selected from the group consisting of Interleukin-2, gelsolin, antibodies, erythropoietin, interferon, human growth hormone, follicle stimulating hormone, and granulocyte colony stimulating factor;
   said composition having a pH of from 6 up to 8;
   said composition packaged in a sterile container.

2. The composition of claim 1, wherein said active compound is included in an amount of not more than 5 weight percent.

3. The composition of claim 1, wherein said water is included in an amount up to 99 weight percent.

4. The composition of claim 1, wherein said choline dihydrogen phosphate is included in an amount of not more than 40 weight percent.

5. The composition of claim 1, wherein said base and said choline dihydrogen phosphate are included together in a combined amount not more than 50 weight percent.

6. The composition of claim 1, wherein said composition is a single phase liquid solution.

7. The composition of claim 1, wherein said composition has an osmolality of 100 to 3,000 milliOsmoles per kilogram of water.

8. The composition of claim 1, wherein said active compound is Interleukin-2.

9. The composition of claim 8, wherein said Interleukin-2 is human Interleukin-2.

10. The composition of claim 8, wherein said Interleukin-2 is aldesleukin.

11. The composition of claim 1, wherein said active compound is gelsolin.

12. The composition of claim 11, wherein said gelsolin is human gelsolin.

13. The composition of claim 1, wherein said active compound is recombinant.

14. The composition of claim 1, wherein said active compound is non-glycosylated.

15. The composition of claim 1 having a shelf life of from 2 days to 2 years at 37° C.

16. The composition of claim 1, wherein said active compound is Interleukin-2 and said composition has a shelf life of 2 days to 2 months at 37° C.

17. A method comprising administering a composition of claim 1 to a subject in need thereof.

18. The composition of claim 1, wherein:
   said active compound is included in an amount of not more than 5 weight percent;
   said water is included in an amount up to 99 weight percent;
   said choline dihydrogen phosphate is included in an amount of not more than 40 weight percent;
   said base and said choline dihydrogen phosphate are included together in a combined amount not more than 50 weight percent;
   said composition is a single phase liquid solution;

said composition has an osmolality of 100 to 3,000 milliOsmoles per kilogram of water; and said active agent is Interleukin-2.

19. The composition of claim 1 having a shelf life of from 2 weeks to 2 years at 37° C.

20. The composition of claim 1 having a shelf life of at least 2 weeks at 37° C.

21. The composition of claim 1 having a shelf life of at least 1 month at 37° C.

22. The composition of claim 1 having a shelf life of at least 1 year at 37° C.

23. The composition of claim 1, further comprising from 0.01 to 50 weight percent of at least one osmolyte.

\* \* \* \* \*